(12) United States Patent
Polonelli et al.

(10) Patent No.: US 7,722,876 B2
(45) Date of Patent: May 25, 2010

(54) TOXIN-RELATED ANTIBODIES WITH ANTIMICROBIAL AND ANTIVIRAL ACTIVITY

(75) Inventors: Luciano Polonelli, Parma (IT); Antonio Cassone, Rome (IT); Luisa Bracci, Siena (IT); Neri Paolo, Siena (IT); Luisa Lozzi, Siena (IT)

(73) Assignee: Istituto Superiore di Sanita, Rome (IT)

( * ) Notice: Subject to any disclaimer, the term of this patent is extended or adjusted under 35 U.S.C. 154(b) by 407 days.

(21) Appl. No.: 10/514,781

(22) PCT Filed: May 9, 2003

(86) PCT No.: PCT/IB03/02348

§ 371 (c)(1),
(2), (4) Date: Mar. 2, 2005

(87) PCT Pub. No.: WO03/095493

PCT Pub. Date: Nov. 20, 2003

(65) Prior Publication Data

US 2006/0280750 A1    Dec. 14, 2006

(30) Foreign Application Priority Data

May 10, 2002   (GB) ................................ 0210783.7

(51) Int. Cl.
- *A61K 38/03* (2006.01)
- *A61K 38/08* (2006.01)
- *A61K 38/06* (2006.01)

(52) U.S. Cl. ............... 424/184.1; 424/185.1; 424/164.1; 424/135.1; 530/328; 530/331; 530/324; 530/326; 530/388.4

(58) Field of Classification Search ........................ None
See application file for complete search history.

(56) References Cited

U.S. PATENT DOCUMENTS 5,693,761 A     12/1997  Schneider
5,830,470 A  *  11/1998  Nakamura et al. ........ 424/133.1

FOREIGN PATENT DOCUMENTS

| DE | 100 19 967 A | | 10/2001 |
|---|---|---|---|
| EP | 1 130 032 | | 9/2001 |
| EP | 1 199 565 | | 4/2002 |
| WO | WO 97/10354 | * | 3/1997 |
| WO | WO 97/42329 | * | 11/1997 |
| WO | WO 98 08090 A | | 2/1998 |
| WO | WO 99/51743 | * | 10/1999 |
| WO | WO 00 26671 A | | 5/2000 |
| WO | WO 00 47625 A | | 8/2000 |
| WO | WO 01 54723 A | | 8/2001 |
| WO | WO 01/98361 | * | 12/2001 |

OTHER PUBLICATIONS

Stryer et al, in Biochemistry, Third edition, W H Freeman Company, New York, pp. 31-33, 1998.*
Ngo et al, The Protein Folding Problem and Tertiary Structure Prediction, pp. 491-495, 1994.*
Wu et al, J Mol Biol 294: 151-162, 1999.*
Barrios et al, J Molecular Recognition 17: 332-338, 2004.*
Kobrin et al, J Immunology 146: 2017-2020, Mar. 1991.*
PhD programmes l'Universita di Torino on line Sep. 10, 2009.*
Polonelli et al., "Monoclonal yeast killer toxin-like candidacidal anti-idiotypic antibodies", Clinical and Diagnostic Laboratory Immunology, vol. 4, No. 2, 1997 pp. 142-146.
Beninati Concetta et al., "Therapy of mucosal candidiasis by expression of an anti-idiotype in human commensal bacteria", Nature Biotechnology, vol. 18, No. 10, Oct. 2000, pp. 1060-1064.
Magliani W. et al, "Therapeutic potential of antiidiotypic single chain antibodies with yeast killer toxin activity", Nature Biotechnology, vol. 15, No. 2, 1997, pp. 155-158.
Vaccari Simona, "Tesi dottorale: Caratterizzazioen strutturale e funzionale di peptidi ad attività antibiotica", Feb. 24, 2003, Università degli studi di Parma, Online.
Magliani W. et al, "Biotechnological approaches to the production of idiotypic vaccines and antiidiotypic antibiotics", Current Pharmaceutical Biotechnology, Netherlands vol. 4 No. 2 Apr. 2003 pp. 91-97.
Polonelli et al., "The efficacy of acquired humoral and cellular immunity in the prevention and therapy of experimental fungal infections", Medical Mycology, vol. 38 No. Supplement 1 2000 pp. 281-292.
Polonelli et al., "Idiotypic vaccination: Immunoprotection mediated by anti-idiotypic antibodies with antibiotic activity", Scandinavian Journal of Immunology, vol. 37 (1) : 105-110, 1993.
Polonelli et al., "Idiotypic intravaginal vaccination to protect against candidal vaginitis by secretory, yeast killer toxin-like anti-idiotypic antibodies", Journal of Immunology vol. 152 No. 6 1994 pp. 3175-3182.
Cassone et al., "Antibodies, killer toxins and antifungal immunoprotection: a lesson from nature?", Immunology Today, Elsevier Publications, Cambridges GB, 18 (4) : 164-169, Apr. 1, 1997.
Savoia Daniela et al., In vitro leishmanicidal activity of a monoclonal antibody mimicking a yeast killer toxinŽjournal of Eucaryotic Microbiology, vol 49, 49(4): 319-323, Jul. 2002.
Polonelli et al., "Human natural yeast killer toxin-like candidacidal anitbodies", Journal of Immunology, vol. 156, No. 5, Apr. 1, 1997, pp. 1880-1885.
Polonelli et al., "Therapeutic activity of an engineered synthetic killer antiidiotypic antibody fragment against experimental mucosal and systemic candidiasis", Infection and Immunity, US, Nov. 2003, vol. 71, No. 11, pp. 6205-6212.

* cited by examiner

Primary Examiner—Phuong Huynh
(74) Attorney, Agent, or Firm—Law Offices of Albert Wai-Kit Chan, PLLC

(57) ABSTRACT

Anti-idiotypic antibodies which recognise the idiotope of an antibody specific for a yeast killer toxin possess microbicidal activity. Fragments (e.g. decapeptides) of these anti-idiotypic antibodies, particularly those comprising CDR residues, also show microbicidal activity, as do peptides having 5 the same sequence but composed of D-amino acids, or including amino acid substitutions. Peptidomimetics of these microbicidal polypeptides are also provided. Antiviral activity is also seen.

6 Claims, 12 Drawing Sheets

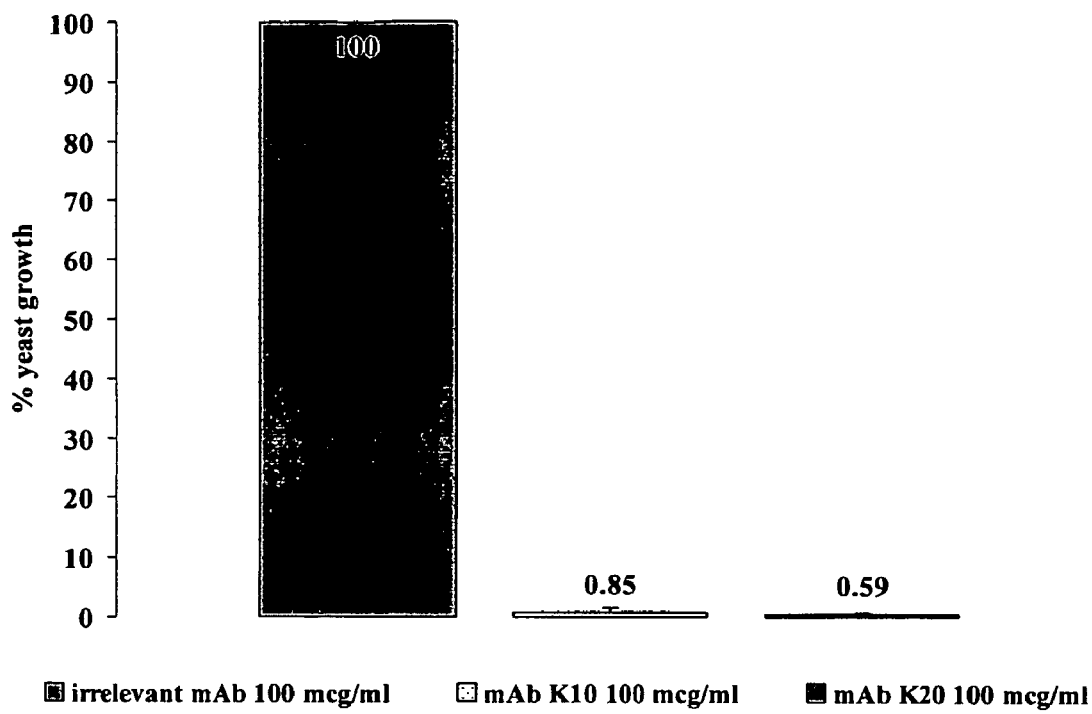
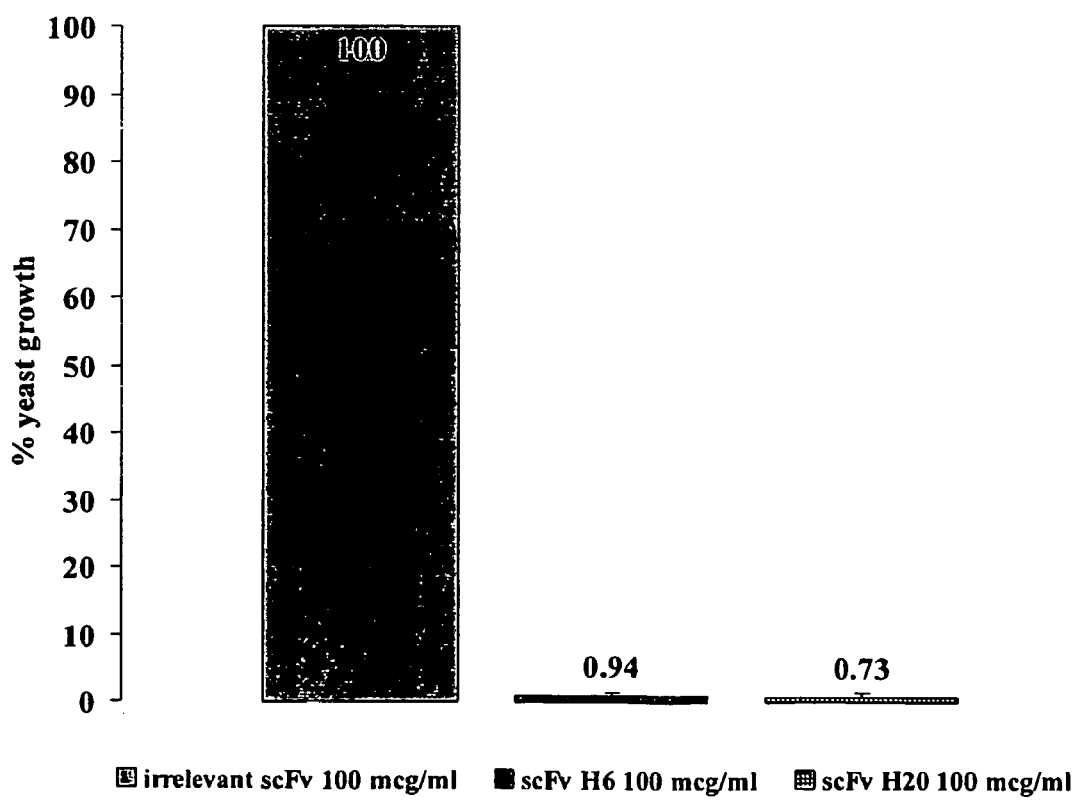

FIGURE 14
FIGURE 14A
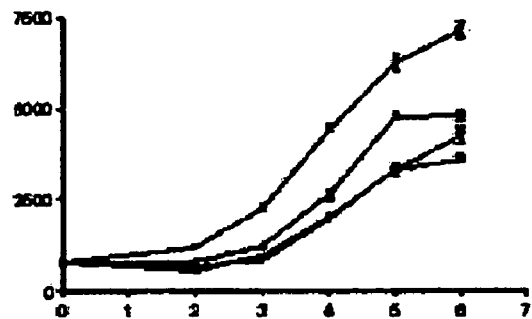
FIGURE 14B
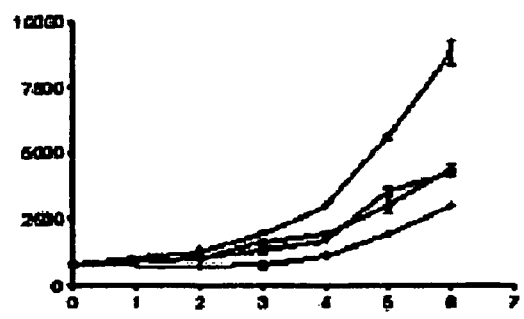
FIGURE 14C
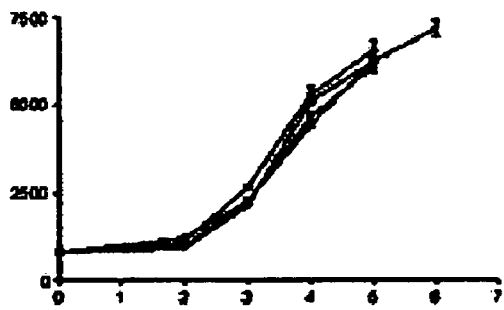
FIGURE 14D
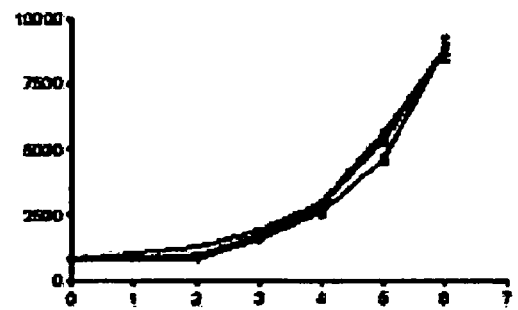
FIGURE 15
FIGURE 15A
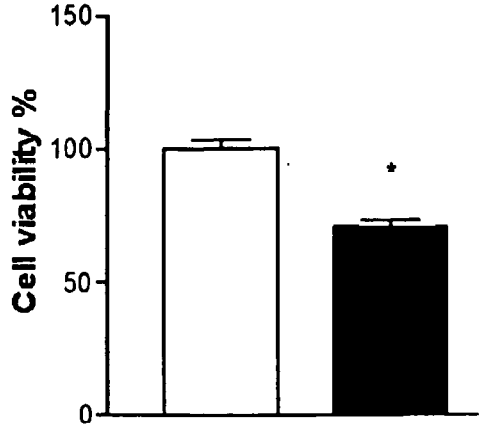
FIGURE 15B
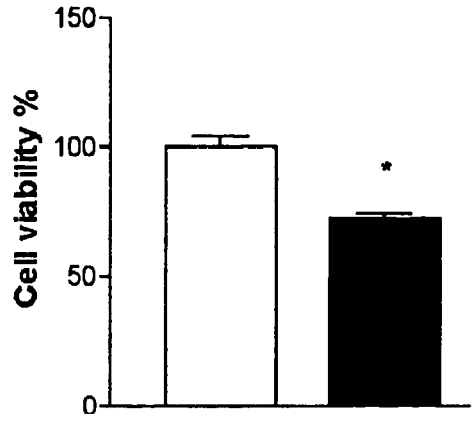

FIGURE 20
FIGURE 20A
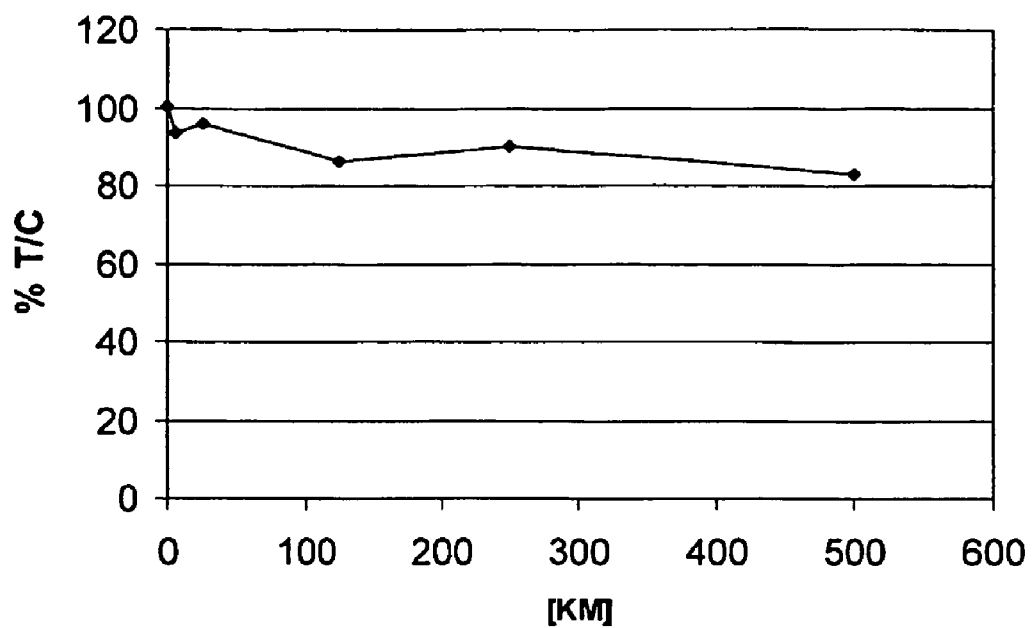
FIGURE 20B
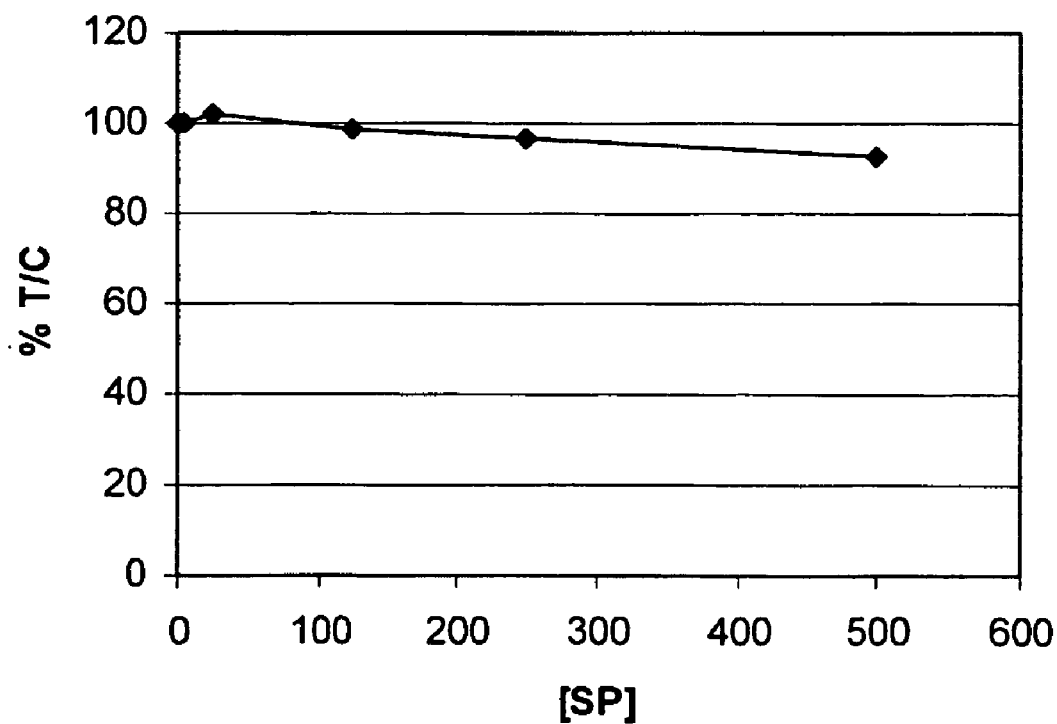

TOXIN-RELATED ANTIBODIES WITH ANTIMICROBIAL AND ANTIVIRAL ACTIVITY

This application is a National Stage Application of International Application No. PCT/IB03/002348, filed May 9, 2003, which claims priority to United Kingdom patent application No. 0210783.7, filed May 10, 2002, the contents of which are incorporated by reference into this application.

TECHNICAL FIELD

This invention is in the field of microbicides and antivirals, in particular those derived from yeast killer toxins.

BACKGROUND ART

Killer toxins (KTs) are proteins secreted by yeasts which are able to kill other yeasts or microorganisms which compete in nature for the same ecological niche [1]. Although they are attractive therapeutic tools, due to their wide spectrum of microbicidal activity, they are of no practical use because of their instability in the host physiological milieu as well as their antigenicity and toxicity. Instead, the use of anti-idiotypic antibodies which mimic KTs has been shown to be effective.

The killer toxin from Pichia anomala ('PaKT') has a wide spectrum of microbicidal activity against pathogens including *Candida albicans, Aspergillus fumigatus, Pneumocystis carinii, Mycobacterium tuberculosis, Pseudomonas aeruginosa,* and *Staphylococcus aureus* [2, 3, 4]. This observation has been exploited by the generation of a PaKT-neutralizing monoclonal antibody in mice (mAb KT4) [5] whose idiotype (Id) is able to induce the production of anti-idiotypic antibodies (antiIds) [6, 7, 8]. These antiIds represent the internal image of the active PaKT domain and as such exert its biological activities, including binding to the PaKT receptor (KTR) of susceptible microorganisms and broad spectrum microbicidal activity overlapping that of PaKT (FIG. 1).

Experimental animals in which these antibodies ('KTIdAb') are raised by idiotypic vaccination with mAb KT4 have repeatedly been shown to be protected against mucosal or systemic challenges by *C.albicans* [7, 8]. There is also ample evidence of susceptibility in vitro to KTIdAb by diverse microbial pathogens such as *M.tuberculosis* (including multidrug resistant strains), *P.carinii*, and others [4, 9].

Idiotypic theory (FIG. 1) also predicted that antibodies against PaKT receptors would mimic PaKT activity. This has been demonstrated in animals and humans during the course of experimental and natural infections caused by PaKT-sensitive microorganisms [10]. Human natural anti-KTR antibodies have been shown to have microbicidal activity in vitro against *C.albicans, M.tuberuclosis,* and *P.carinii*, to inhibit *P.carinii* infectivity of nude rats, and to be protective against passive transfer in vivo, in an experimental model of rat vaginal candidiasis [4, 10, 11].

Based on these results, and in order to obtain standard KTIdAb in sufficient amounts, rat monoclonal IgM (mAb K10) and mouse single-chain Fv (scFv H6) microbicidal antibodies have been obtained [12, 13]. These two antibodies have strong microbicidal effects in vitro against important pathogenic microorganisms including: *C.albicans* [12, 13]; *C.krusei* and *C.glabrata* (including fluconazole-resistant strains); *Cryptococcus neoformans; A. fumigalus* [14]; *M.tuberculosis* [4]; *S.aureus, Enterococcus faecalis, E.faecium,* and *Streptococcus pneumoniae* (including methicillin-, vancomycin- and penicillin-resistant strains) [15], *S.mutans,* *Leishmania major, L.infantum* and *Achantamoeba castellani*. Furthermore, they showed specific therapeutic activity in an experimental model of rat vaginal candidiasis by intravaginal administration [13]. In addition, K10 proved to be therapeutic against *P.carinii* pneumonia in rats infected by aerosol administration [16], and in mice transplanted with T cell depleted bone marrow against aspergillosis caused by nasal instillation [14].

Although the existence of scFv H6 has been reported, a method for its manufacture has not previously been disclosed, and nor has its amino acid sequence.

It is an object of the invention to provide further and improved antimicrobial and/or antiviral compounds.

DISCLOSURE OF THE INVENTION

Antibodies of the Invention

The invention provides an anti-idiotypic antibody which recognises the idiotope of an antibody specific for a yeast killer toxin, with the proviso that the anti-idiotypic antibody is not the K10 rat monoclonal antibody. The antibody preferably has microbicidal activity (e.g. it retains yeast killer toxin activity) and/or antiviral activity.

An anti-idiotypic antibody of the invention can be used to generate further anti-idiotypic antibodies (anti-anti-anti-idiotypic with respect to the original killer toxin). The anti-anti-anti-idiotypic antibody of the invention can in turn be used to generate further anti-idiotypic antibodies (anti-anti-anti-anti-idiotypic with respect to the original killer toxin). Thus the microbicidal activity of the killer toxin can be transferred through successive generations of anti-idiotypic antibodies, and these various generations are within the scope of the invention.

Thus the invention provides an antibody which recognises the idiotope of an anti-idiotypic antibody of the invention (i.e. it provides an anti-anti-anti-idiotypic antibody), an antibody which recognises the idiotope of such an anti-anti-anti-idiotypic antibody (i.e. an anti-anti-anti-anti-anti-idiotypic antibody) etc. In general, therefore, the invention provides an antibody which recognises the idiotope of an $(anti-)_n$-idiotypic antibody of the invention, wherein n is an odd number (e.g. 1, 3, 5, 7, 9 etc.). These antibodies will generally bind to the idiotope of an anti-toxin antibody such as KT4 and preferably have microbicidal and/or antiviral activity.

For production of these $(anti-)_n$-idiotypic antibodies, the invention provides $(anti-)_m$-idiotypic antibodies, wherein m is an even number (e.g. 2, 4, 6, 8 etc.). These antibodies will generally bind to a killer toxin.

The term 'antibody' includes any of the various natural and artificial antibodies and antibody-derived proteins which are available. Thus the term 'antibody' includes polyclonal antibodies, monoclonal antibodies, Fab fragments, $F(ab')_2$ fragments, Fv fragments, single-chain Fv (scFV) antibodies, oligobodies, etc.

To increase compatibility with the human immune system, it is preferred to use human antibodies. As an alternative, antibodies of the invention may be chimeric or humanized versions of non-human antibodies [e.g. refs. 17 & 18].

In chimeric antibodies, non-human constant regions are substituted by human constant regions but variable regions remain non-human.

Humanized antibodies may be achieved by a variety of methods including, for example: (1) grafting complementarity determining regions (CDRs) from the non-human variable region onto a human framework ("CDR-grafting"), with the optional additional transfer of one or more framework residues from the non-human antibody ("humanizing"); (2) transplanting entire non-human variable domains, but "cloaking" them with a human-like surface by replacement of surface residues ("veneering"). In the present invention, humanized antibodies include those obtained by CDR-grafting, humanizing, and veneering or variable regions. [e.g. refs. 19 to 25].

The constant regions of humanized antibodies are derived from human immunoglobulins. The heavy chain constant region can be selected from any of the five isotypes: α, δ, ε, γ or μ.

Humanized or fully-human antibodies can also be produced using transgenic animals that are engineered to contain human immunoglobulin loci. For example, ref. 26 discloses transgenic animals having a human Ig locus wherein the animals do not produce functional endogenous immunoglobulins due to the inactivation of endogenous heavy and light chain loci. Ref. 27 also discloses transgenic non-primate mammalian hosts capable of mounting an immune response to an immunogen, wherein the antibodies have primate constant and/or variable regions, and wherein the endogenous immunoglobulin-encoding loci are substituted or inactivated. Ref. 28 discloses the use of the Cre/Lox system to modify the immunoglobulin locus in a mammal, such as to replace all or a portion of the constant or variable region to form a modified antibody molecule. Ref. 29 discloses non-human mammalian hosts having inactivated endogenous Ig loci and functional human Ig loci. Ref. 30 discloses methods of making transgenic mice in which the mice lack endogenous heavy chains, and express an exogenous immunoglobulin locus comprising one or more xenogeneic constant regions.

Antibodies of the invention may include a label. The label may be detectable directly, such as a radioactive or fluorescent label. Alternatively, the label may be detectable indirectly, such as an enzyme whose products are detectable (e.g. luciferase, β-galactosidase, peroxidase etc.) or a binding partner such as biotin and avidin or streptavidin.

Antibodies of the invention may be attached to a solid support.

Antibodies of the invention may be produced by any suitable means (e.g. by recombinant expression).

Preferred antibodies of the invention are single chain Fv antibodies. These may be produced by joining heavy and light chain variable regions from a starting monoclonal antibody of interest, or may be identified by screening a scFv library (e.g. by phage display). Reference 31 discloses a phage display method for producing anti-idiotypic scFv antibodies.

Particularly preferred scFv antibodies of the invention are H6 (SEQ IDs 1 & 2) and H20 (SEQ IDs 21 & 22). Antibodies comprising one or more (e.g. 2, 3, 4, 5 or 6) of the CDRs from H6 and H20 are also preferred, as are derivatives of H6 and H20 in which: (a) one or more (e.g. 2, 3, 4, 5, 6, 7, 8, 9, 10, 11, 12, 13, 14, 15) framework residues are substituted with other amino acids; (b) the linker sequence (SEQ ID 30) is replaced with an alternative linker sequence; (c) the 'E-tag' sequence (SEQ ID 59) is omitted or replaced. Fusion proteins comprising H6 or H20, or derivatives (a) to (c), at the N- or C-terminus are also useful. The H6 and H20 CDRs may optionally contain 1, 2, 3 or 4 amino acid substitutions.

Other preferred antibodies of the invention are humanized antibodies. Particularly preferred humanized antibodies of the invention comprise one or more (e.g. 2, 3, 4, 5 or 6) CDRs from H6, H20 or K20.

Polypeptides and Antibody Fragments

It has surprisingly been found that short fragments (e.g. 10mer fragments) of the variable regions of anti-idiotypic antibodies of the invention can retain the antibodies' KT-like microbicidal activity. Even more surprisingly, L-amino acids in these fragments can be replaced with D-amino acids without removing microbicidal activity, and amino acids within the fragments can be substituted with other amino acids without removing microbicidal activity. In addition, the fragments have been found to possess anti-viral activity.

Thus the invention provides a polypeptide comprising: at least one amino acid sequence which is a fragment of at least x amino acids from the amino acid sequence of a variable region of an antibody of the invention, optionally with y amino acid(s) within said x amino acids being substituted by different amino acid(s). The polypeptide preferably has microbicidal and/or antiviral activity.

The polypeptide preferably consists of no more than 250 amino acids (e.g. no more than 225, 200, 190, 180, 170, 160, 150, 140, 130, 120, 110, 100, 95, 90, 80, 70, 60, 50, 45, 40, 35, 30, 25, 20, 19, 18, 17, 16, 15, 14, 13, 12, 11, 10, 9, 8, 7, 6 or even 5 amino acids). Polypeptides consisting of between 5 and 90 amino acids are preferred (e.g. consisting of between 5 and 80, 5 and 70, 5 and 60 amino acids etc.). Particularly preferred are polypeptides consisting of between 8 and 25 amino acids are preferred.

The polypeptide preferably consists of at least 3 amino acids (e.g. at least 4, 5, 6, 7, 8, 9, 10, 11, 12, 13, 14, 15, 16, 17, 18, 19, 20, 25, 30, 35, 40, 45, 50, 55, 60, 70, 80, 90, 100, 125, 150, 175, or at least 200 amino acids).

The value of x is preferably at least 3 (e.g. at least 4, 5, 6, 7, 8, 9, 10, 11, 12, 13, 14, 15, 16, 17, 18, 19, 20, 25, 30, 35, 40, 45, 50, 55, 60, 70, 80, 90, 100, 125, 150, 175, or at least 200).

The value of y will be less than x and, depending on the value of x, it may be x-1, x-2, x-3, x-4, x-5, x-6, x-7, x-8, x-9, x-10, x-11, x-12, x-13, x-14, or x-15. Preferred values of y are 1, 2, 3, 4 and 5. The y amino acids are typically substituted by A, C, D, E, F, G, H, I, K, L, M, N, P, Q, R, S, T, V, W, or Y. Each of the y substitutions may be the same or different as the others. The substitution is preferably by G or, more preferably, by A [32, 33]. The substituting amino acid may be an L- or a D- amino acid but, where the other x amino acids all share a single stereo-configuration (i.e. all D- or all L-), it preferably has that stereo-configuration (although, of course, G has no stereoisomers).

Where the fragment of x amino acids includes a C, the value of y is preferably at least 1 such that the C is substituted for another amino acid, such as S. Removal of C in this way improves resistance to oxidation.

The fragment of at least x amino acids preferably includes at least z amino acids from a CDR within the antibody. The value of z is preferably at least 1 (e.g. 2, 3, 4, 5, 6, 7, 8, 9 or 10 or more).

The polypeptide may comprise more than one (e.g. 2, 3, 4, 5, 6) amino acid sequence each of which is a fragment of at least x amino acids (e.g. SEQ ID 25). In such polypeptides, the value of x in each fragment may be the same or different, the value of y within each x may be the same or different, and the value of z within each x may be the same or different. The fragments may be joined by linker peptides such as glycine-rich linker sequences (e.g. SEQ ID 30).

The invention also provides a polypeptide having formula NH₂—A—B—C—COOH, wherein: A is a polypeptide sequence consisting of a amino acids; C is a polypeptide sequence consisting of c amino acids; B is a polypeptide sequence which is, as defined above, a fragment of at least x amino acids from the amino acid sequence of a variable region of an antibody of the invention, optionally with y amino acids within said x amino acids being substituted by different amino acid(s). The polypeptide preferably has microbicidal and/or antiviral activity.

The value of a is generally at least 1 (e.g. at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 150, 200, 250, 300, 350, 400, 450, 500 etc.). The value of c is generally at least 1 (e.g. at least 2, 3, 4, 5, 6, 7, 8, 9, 10, 11,12, 13,14,15, 16, 17, 18, 19, 20, 21, 22, 23, 24, 25, 26, 27, 28, 29, 30, 35, 40, 45, 50, 60, 70, 80, 90, 100, 150, 200, 250, 300, 350, 400, 450, 500 etc.). The value of a+c is at least 1 (e.g. at least 2, 3,4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 150, 200, 250, 300, 350, 400, 450, 500 etc.). It is preferred that the value of a+c is at most 1000 (e.g. at most 900, 800, 700, 600, 500, 450, 400, 350, 300, 250, 200, 190, 180, 170, 160, 150, 140, 130, 120, 110, 100, 90, 80, 70, 60, 50, 40, 30, 25, 20, 19, 18, 17, 16, 15, 14, 13, 12, 11, 10, 9, 8, 7, 6, 5, 4, 3, 2).

The amino acid sequence of —A— typically shares less than m% sequence identity to the a amino acids which are N-terminal of sequence —B— in a variable region of an antibody of the invention (e.g. in SEQ ID 2), and the amino acid sequence of —C— typically shares less than n% sequence identity to the c amino acids which are C-terminal of sequence —B— in a variable region of an antibody of the invention (e.g. in SEQ ID 2). In general, the values of m and n are both 60 or less (e.g. 50, 40, 30, 20, 10 or less). The values of m and n may be the same as or different from each other.

The polypeptide may comprise a mimotope of a yeast killer toxin.

Preferred polypeptides comprise sequence $AA_1$-$AA_2$$AA_3$-$AA_4$-$AA_5$-$AA_6$-$AA_7$-$AA_8$-$AA_9$-$AA_{10}$, wherein: each of $AA_1 \ldots AA_{10}$ is independently a D- or L- amino acid; $AA_1$ is E, A or G; $AA_2$ is K, A or G; $AA_3$ is V, A or G; $AA_4$ is T, A or G; $AA_5$ is M, A or G; $AA_7$ is T, A or G; $AA_7$ is C, S, A or G; $AA_8$ is S, A or G; $AA_9$ is A or G; and $AA_{10}$ is S, A or G; provided that no more than p of $AA_1$, $AA_2$, $AA_3$, $AA_4$, $AA_5$, $AA_6$, $AA_7$, $AA_8$, $AA_9$, and $AA_{10}$ are A; and provided that no more than q of $AA_1$, $AA_2$, $AA_3$, $AA_4$, $AA_5$, $AA_6$, $AA_7$, $AA_8$, $AA_9$, and $AA_{10}$ are G. The value of p is 1, 2, 3 or 4, and is preferably 1 or 2. The value of q is 0, 1 or 2 and is preferably 0 (i.e. no glycine residues) or 1.

Particularly preferred polypeptides comprise or consist of amino acid sequences SEQ IDs : 3, 4, 5, 6, 7, 8, 9, 10, 11, 12, 14, 15, 16, 17, 18, 19, 20, 23, 24, 25, 26, 27, 32, 33, 34, 35, 36, 37, 38, 39, 40, 41, 42, 43, 44, 45, 46, 47, 48, 49, 50, 51, 52, 53, 54, 55, 56, 57, 58, 60, 61, 62, 63, 64, 65, 66, 67, 68, 69, 70 & 71, with constituent amino acids in the D- and/or L- configuration. SEQ IDs 3, 4, 23, 27 and 33 are most preferred.

For reference, the values of x, y and z for various of these polypeptide sequences are as follows:

| SEQ ID | x | y | z |
|---|---|---|---|
| 3 | 10 | 0 | 3 |
| 4 | 10 | 1 | 3 |
| 5 | 10 | 1 | 3 |
| 6 | 10 | 1 | 3 |
| 7 | 10 | 1 | 3 |
| 8 | 10 | 1 | 3 |
| 9 | 10 | 1 | 3 |
| 10 | 10 | 1 | 3 |
| 11 | 10 | 1 | 3 |
| 12 | 10 | 1 | 3 |
| 14 | 9 | 1 | 2 |
| 15 | 8 | 1 | 1 |
| 16 | 7 | 1 | 0 |

-continued

| SEQ ID | x | y | z |
|---|---|---|---|
| 17 | 6 | 1 | 0 |
| 18 | 5 | 1 | 0 |
| 19 | 4 | 1 | 0 |
| 20 | 3 | 1 | 0 |
| 23 | 10 | 2 | 3 |
| 24 | 10 | 0 | 3 |
| 26 | 15 | 0 | 8 |
| 27 | 9 | 0 | 8 |
| 32 | 10 | 2 | 3 |
| 33 | 10 | 2 | 3 |

Further microbicidal and/or antiviral fragments can be identified by screening panels of overlapping peptide fragments once the sequence of an anti-idiotypic antibody (e.g. H6, H20, K20) is known e.g. by using the PepScan method [34]. Overlapping fragments of 4mers, 5mers, 6mers, 7mers, 8mers, 9mers, 10 mers, 11 mers, 12mers, 13mers etc. can be tested for microbicidal ability without difficulty e.g. using the in vitro assays disclosed in the examples herein.

Polypeptides of the invention may be linear, branched or cyclic [35] but they are preferably linear chains of amino acids. Where cysteine residues are present, polypeptides of the invention may be linked to other polypeptides via disulfide bridges (and, in particular, linked to other polypeptides of the invention to form homodimers or heterodimers). Polypeptides of the invention may comprise L-amino acids and/or D-amino acids. The inclusion of D-amino acids is preferred in order to confer resistance to mammalian proteases.

Polypeptide Production

Polypeptides of the invention may be produced by various means.

A preferred method for production involves in vitro chemical synthesis [36, 37]. Solid-phase peptide synthesis is particularly preferred, such as methods based on t-Boc or Fmoc [38] chemistry. Enzymatic synthesis [39] may also be used in part or in full.

As an alternative to chemical synthesis, biological synthesis may be used e.g. the polypeptides may be produced by translation. This may be carried out in vitro or in vivo. Biological methods are in general restricted to the production of polypeptides based on L-amino acids, but manipulation of translation machinery (e.g. of aminoacyl-tRNA molecules) can be used to allow the introduction of D-amino acids (or of other non-natural amino acids, such as iodotyrosine or methylphenylalanine, azidohomoalanine, etc.) [40]. Where D-amino acids are included in the polypeptides of the invention, however, it is preferred to use chemical synthesis. Further details on polypeptide expression are given below.

To facilitate biological peptide synthesis, the invention provides nucleic acid that encodes a polypeptide of the invention. The invention also provides nucleic acid that encodes an antibody of the invention.

The nucleic acid may be DNA or RNA (or hybrids thereof), or their analogues, such as those containing modified backbones (e.g. phosphorothioates) or peptide nucleic acids (PNA). It may be single-stranded (e.g. mRNA) or double-stranded, and the invention includes both individual strands of a double-stranded nucleic acid (e.g. for antisense, priming or probing purposes). It may be linear or circular. It may be labelled. It may be attached to a solid support.

Nucleic acid according to the invention can, of course, be prepared in many ways e.g. by chemical synthesis (e.g. phosphoramidite synthesis of DNA) in whole or in part, by nuclease digestion of longer molecules, by ligation of shorter molecules, from genomic or cDNA libraries, by use of polymerases etc.

The invention provides vectors (e.g. plasmids) comprising nucleic acid of the invention (e.g. expression vectors and cloning vectors) and host cells (prokaryotic or eukaryotic) transformed with such vectors.

These vectors can also be used for nucleic acid immunisation [e.g. refs. 41, 42, 43, 44, 45 etc.]. Peptides can be expressed in vivo in this way, as can therapeutic antibodies. It is also possible to express idiotypes (e.g. the KT4 idiotope) to elicit anti-idiotypic antibodies of the invention in a patient in vivo.

Host cells which contain nucleic acid of the invention and which express polypeptide or antibody of the invention may be used as delivery vehicles e.g. commensal bacteria [46]. This is particularly useful for delivery to mucosal surfaces.

The Yeast Killer Toxin

Killer toxins were originally identified in *Saccharomyces cerevisiae* [47] and have since been identified in other genera of yeasts including *Pichia* (such as *P.anomala*, *P.kluyveri* and *P.farinosa*), *Hanseniaspora* (such as *H.uvarum*), *Williopsis* (such as *W.mrakii*), *Candida* (such as *C.maltosa*), *Debaryomyces* (such as *D.hansenii*), *Schwanniomyces* (such as *S.occidentalis*), *Cryptococcus* (such as *C.humicola*), *Torulopsis* (such as *T.glabrata*), *Ustilago* (such as *U.maydis*), *Zygosaccharomyces* (such as *Z.bailii*) and *Kluyveromyces* (such as *K.lactis* and *K.phaffii*).

Any of these various toxins can be used with the present invention. Preferred toxins are (a) those with a broad range of microbicidal activity and (b) those from *Pichia*. A particularly preferred toxin is the killer toxin from *Pichia anomala* ('PaKT').

Microbicidal Activity

The polypeptide or antibody of the invention preferably has microbicidal activity.

Preferably, it has anti-mycotic activity and/or anti-bacterial activity. Anti-bacterial activity may be against a Gram-negative or Gram-positive bacterium.

More preferably, it has activity against a microbe which has a glucan-based cell wall.

Microbes which are susceptible to polypeptides and antibodies of the invention include bacteria, fungi and protozoa, and include, but are not limited to: *Candida* species, such as *C.albicans*; *Cryptococcus* species, such as *C.neoformans*; *Enterococcus* species, such as *E.faecalis*; *Streptococcus* species, such as *S.pneumoniae*, *S.mutans*, *S.agalactiae* and *S.pyogenes*; *Leishmania* species, such as *L.major* and *L.infantum*; *Acanthamoeba* species, such as *A.castellani*; *Aspergillus* species, such as *A.fumigatus*; *Pneumocystis* species, such as *P.carinii*; *Mycobacterium* species, such as *M.tuberculosis*; *Pseudomonas* species, such as *P.aeruginosa*; *Staphylococcus* species, such as *S.aureus*; *Salmonella* species, such as *S.typhimurium*; and *Escherichia* species, such as *E. coli*.

Antiviral Activity

The polypeptide or antibody of the invention preferably has antiviral activity.

Preferably, it has antiviral activity against a human virus, such as a myxovirus (e.g. an orthomyxovirus) or a retrovirus (e.g. a lentivirus).

Viruses which are susceptible to polypeptides and antibodies of the invention include, but are not limited to: influenza virus (A or B), human immunodeficiency virus (HIV-1, HIV-2, HIV-O), respiratory syncytial virus (RSV), yellow fever virus, etc.

Drug Design and Peptidomimetics

Polypeptides of the invention are useful microbicides and antivirals in their own right. However, they may be refined to improve microbicidal and/or antiviral activity (either general or specific) or to improve pharmacologically important features such as bio-availability, toxicology, metabolism, pharmacokinetics etc. The polypeptides may therefore be used as lead compounds for further research and refinement.

Polypeptides of the invention can be used for designing peptidomimetic molecules [e.g. refs. 48 to 53] with microbicidal and/or antiviral activity. These will typically be isosteric with respect to the polypeptides of the invention but will lack one or more of their peptide bonds. For example, the peptide backbone may be replaced by a non-peptide backbone while retaining important amino acid side chains.

The peptidomimetic molecule may comprise sugar amino acids [54]. Peptoids may be used.

To assist in the design of peptidomimetic molecules, a pharmacophore (i.e. a collection of chemical features and 3D constraints that expresses specific characteristics responsible for activity) can be defined for the KM peptides. The pharmacophore preferably includes surface-accessible features, more preferably including hydrogen bond donors and acceptors, charged/ionisable groups, and/or hydrophobic patches. These may be weighted depending on their relative importance in conferring activity [55].

Pharmacophores can be determined using software such as CATALYST (including HypoGen or HipHop) [56], CERIUS$^2$, or constructed by hand from a known conformation of a polypeptide of the invention. The pharmacophore can be used to screen structural libraries, using a program such as CATALYST. The CLIX program [57] can also be used, which searches for orientations of candidate molecules in structural databases that yield maximum spatial coincidence with chemical groups which interact with the receptor.

The binding surface or pharmacophore can be used to map favourable interaction positions for functional groups (e.g. protons, hydroxyl groups, amine groups, hydrophobic groups) or small molecule fragments. Compounds can then be designed de novo in which the relevant functional groups are located in substantially the same spatial relationship as in polypeptides of the invention.

Functional groups can be linked in a single compound using either bridging fragments with the correct size and geometry or frameworks which can support the functional groups at favourable orientations, thereby providing a peptidomimetic compound according to the invention. Whilst linking of functional groups in this way can be done manually, perhaps with the help of software such as QUANTA or SYBYL, automated or semi-automated de novo design approaches are also available, such as:

MCSS/HOOK [58, 59, 56], which links multiple functional groups with molecular templates taken from a database.

LUDI [60, 56], which computes the points of interaction that would ideally be fulfilled by a ligand, places fragments in the binding site based on their ability to interact with the receptor, and then connects them to produce a ligand.

MCDLNG [61], which fills a receptor binding site with a close-packed array of generic atoms and uses a Monte Carlo procedure to randomly vary atom types, positions, bonding arrangements and other properties.

GROW [62], which starts with an initial 'seed' fragment (placed manually or automatically) and grows the ligand outwards.

SPROUT [63], suite which includes modules to: identify favourable hydrogen bonding and hydrophobic regions within a binding pocket (HIPPO module); select functional groups and position them at target sites to form starting fragments for structure generation (EleFAnT); generate skeletons that satisfy the steric constraints of the binding pocket by growing spacer fragments onto the start fragments and then connecting the resulting part skeletons (SPIDeR); substitute hetero atoms into the skeletons to generate molecules with the electrostatic properties that are complementary to those of the receptor site (MARABOU). The solutions can be clustered and scored using the ALLigaTOR module.

CAVEAT [64], which designs linking units to constrain acyclic molecules.

LEAPFROG [65], which evaluates ligands by making small stepwise structural changes and rapidly evaluating the binding energy of the new compound. Changes are kept or discarded based on the altered binding energy, and structures evolve to increase the interaction energy with the receptor.

GROUPBUILD [66], which uses a library of common organic templates and a complete empirical force field description of the non-bonding interactions between a ligand and receptor to construct ligands that have chemically reasonable structure and have steric and electrostatic properties complimentary to the receptor binding site.

RASSE [67]

These methods identify microbicidal compounds. These compounds may be designed de novo, may be known compounds, or may be based on known compounds. The compounds may be useful microbicides and/or antivirals themselves, or they may be prototypes which can be used for further pharmaceutical refinement (i.e. lead compounds) in order to improve binding affinity or other pharmacologically important features (e.g. bio-availability, toxicology, metabolism, pharmacokinetics etc.).

The invention thus provides: (i) a compound identified using these drug design methods; (ii) a compound identified using these drug design methods, for use as a pharmaceutical; (iii) the use of a compound identified using these drug design methods in the manufacture of a microbicide and/or an antiviral; and (iv) a method of treating a patient with a microbial or viral infection, comprising administering an effective amount of a compound identified using these drug design methods.

As well as being useful compounds individually, ligands identified in silico by the structure-based design techniques can also be used to suggest libraries of compounds for 'traditional' in vitro or in vivo screening methods. Important pharmaceutical motifs in the ligands can be identified and mimicked in compound libraries (e.g. combinatorial libraries) for screening for microbicidal and/or antiviral activity.

Pharmaceutical Compositions

The invention provides a pharmaceutical composition comprising (a) polypeptide, peptidomimetic, nucleic acid and/or antibody of the invention and (b) a pharmaceutical carrier.

Component (a) is the active ingredient in the composition, and this is present at a therapeutically effective amount i.e. an amount sufficient to inhibit microbial/viral growth and/or survival in a patient, and preferably an amount sufficient to eliminate microbial infection. The precise effective amount for a given patient will depend upon their size and health, the nature and extent of infection, and the composition or combination of compositions selected for administration. The effective amount can be determined by routine experimentation and is within the judgment of the clinician. For purposes of the present invention, an effective dose will generally be from about 0.01 mg/kg to about 5 mg/kg, or about 0.01 mg/ kg to about 50 mg/kg or about 0.05 mg/kg to about 10 mg/kg. Pharmaceutical compositions based on polypeptides, antibodies and nucleic acids are well known in the art. Polypeptides may be included in the composition in the form of salts and/or esters.

Carrier (b) can be any substance that does not itself induce the production of antibodies harmful to the patient receiving the composition, and which can be administered without undue toxicity. Suitable carriers can be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art. Pharmaceutically acceptable carriers can include liquids such as water, saline, glycerol and ethanol. Auxiliary substances, such as wetting or emulsifying agents, pH buffering substances, and the like, can also be present in such vehicles. Liposomes are suitable carriers. A thorough discussion of pharmaceutical carriers is available in ref. 68.

Viral and microbial infections affect various areas of the body and so the compositions of the invention may be prepared in various forms. For example, the compositions may be prepared as injectables, either as liquid solutions or suspensions. Solid forms suitable for solution in, or suspension in, liquid vehicles prior to injection can also be prepared. The composition may be prepared for topical administration e.g. as an ointment, cream or powder. The composition be prepared for oral administration e.g. as a tablet or capsule, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops, as a spray, or as a powder [e.g. 69]. The composition may be included in a mouthwash. The composition may be lyophilised.

The pharmaceutical composition is preferably sterile. It is preferably pyrogen-free. It is preferably buffered e.g. at between pH 6 and pH 8, generally around pH 7.

The invention also provides a delivery device containing a pharmaceutical composition of the invention. The device may be, for example, a syringe or an inhaler.

Compositions of the invention may be used in conjunction with known anti-fungals. Suitable anti-fungals include, but are not limited to, azoles (e.g. fluconazole, itraconazole), polyenes (e.g. amphotericin B), flucytosine, and squalene epoxidase inhibitors (e.g. terbinafine) [see also ref. 70]. Compositions may also be used in conjunction with known antivirals e.g. HIV protease inhibitors, a 2',3'-dideoxynucleoside (e.g. DDC, DDI), 3'-azido-2',3'-dideoxynucleosides (AZT), 3'-fluoro-2',3'-dideoxynucleosides (FLT), 2',3'-didehydro-2', 3'-dideoxynucleosides (e.g. D4C, D4T) and carbocyclic derivatives thereof (e.g. carbovir), 2'-fluoro-ara-2',3'-dideoxynucleosides, 1,3-dioxolane derivatives (e.g. 2',3'-dideoxyl-3'-thiacytidine), oxetanocin analogues and carbocyclic derivatives thereof (e.g. cyclobut-G) and the 9-(2-phosphonylmethoxyethyl)adenine (PMEA) and 9-(3-fluoro-2-phosphonylmethoxypropyl)adenine (FPMPA) derivatives, tetrahydro-imidazo[4,5,1 -jk][1,4]-benzodiazepin-2(1H)one (TIBO), 1-[(2-hydroxyethoxy)-methyl]-6-(phenylthio) thymine (HEPT), dipyrido[3,2-b:2',3'-e]-[1,4]diazepin-6-one (nevirapine) and pyridin-2(1H)one derivatives, 3TC, etc.

Medical Treatments and Uses

The invention provides antibody, polypeptide, peptidomimetic or nucleic acid of the invention for use as a medicament. The invention also provides a method for treating a patient suffering from a microbial and/or viral infection, comprising administering to the patient a pharmaceutical composition of the invention. The invention also provides the use of antibody, polypeptide, peptidomimetic or nucleic acid of the invention in the manufacture of a medicament for treating a patient.

The patient is preferably a human. The human may be an adult or, preferably, a child. The human may be immunocompromised.

These uses and methods are particularly useful for treating infections of: *Candida* species, such as *C.albicans*; *Cryptococcus* species, such as *C.neoformans*; *Enterococcus* species, such as *E.faecalis*; *Streptococcus* species, such as *S.pneumoniae*, *S.mutans*, *S.agalactiae* and *S.pyogenes*; *Leishmania* species, such as *L.major* and *L.infantum*; *Acanthamoeba* species, such as *A.castellani*; *Aspergillus* species, such as *A.fumigatus* and *A.flavus*; *Pneumocystis* species, such as *P.carinii*; *Mycobacterium* species, such as *M.tuberculosis*; *Pseudomonas* species, such as *P.aeruginosa*; *Staphylococcus* species, such as *S.aureus*; *Salmonella* species, such as *S.typhimurium*; *Coccidioides* species such as *C.immitis*; *Trichophyton* species such as *T.verrucosum*; *Blastomyces* species such as *B.dermatidis*; *Histoplasma* species such as *H.capsulatum*; *Paracoccidioides* species such as *P.brasiliensis*; *Pythiumn* species such as *P.insidiosum*; and *Escherichia* species, such as *E.coli*. They are also useful for treating infections of: influenza viruses and HIV.

The uses and methods are particularly useful for treating diseases including, but not limited to: candidosis, aspergillosis, cryptococcosis, dermatomycoses, sporothrychosis and other subcutaneous mycoses, blastomycosis, histoplasmosis, coccidiomycosis, paracoccidiomycosis, pneumocystosis, thrush, tuberculosis, mycobacteriosis, respiratory infections, scarlet fever, pneumonia, impetigo, rheumatic fever, sepsis, septicaemia, cutaneous and visceral leishmaniasis, corneal acanthamoebiasis, keratitis, cystic fibrosis, typhoid fever, gastroenteritis and hemolytic-uremic syndrome, flu and AIDS. Anti-*C.albicans* activity is particularly useful for treating infections in AIDS patients.

Efficacy of treatment can be tested by monitoring microbial/viral infection after administration of the pharmaceutical composition of the invention.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, ocular, nasal, aural, or pulmonary administration. Injection or intranasal administration is preferred.

Dosage treatment can be a single dose schedule or a multiple dose schedule.

Pharmaceutical compositions of the invention may also be used prophylactically e.g. in a situation where contact with microbes is expected and where establishment of infection is to be prevented. For instance, the composition may be administered prior to surgery.

Polypeptide Expression and Other General Techniques

The practice of the present invention will employ, unless otherwise indicated, conventional techniques of molecular biology, microbiology, recombinant DNA, and immunology, which are within the skill of the art. Such techniques are explained fully in the literature e.g. *Sambrook Molecular Cloning; A Laboratory Manual, Second Edition* (1989); *DNA Cloning, Volumes I and ii* (D. N Glover ed. 1985); *Oligonucleolide Synthesis* (M. J. Gait ed, 1984); *Nucleic Acid Hybridization* (B. D. Hames & S. J. Higgins eds. 1984); *Transcription and Translation* (B. D. Hames & S. J. Higgins eds. 1984); *Animal Cell Culture (R. I. Freshney ed.* 1986); *Immobilized Cells and Enzymes* (IRL Press, 1986); B. Perbal, *A Practical Guide to Molecular Cloning (*1984); the *Methods in Enzymology* series (Academic Press, Inc.), especially volumes 154 & 155; *Gene Transfer Vectors for Mammalian Cells* (J. H. Miller and M. P. Calos eds. 1987, Cold Spring Harbor Laboratory); Mayer and Walker, eds. (1987), *Immunochemical Methods in Cell and Molecular Biology* (Academic Press, London); Scopes, (1987) *Protein Purification: Principles and Practice, Second Edition* (Springer-Verlag, N.Y.), and *Handbook of Experimental Immunology, Volumes I-IV* (Weir& Blackwell eds 1986).

Standard abbreviations for nucleotides and amino acids are used in this specification:

| Nucleotides | | | | | | | |
|---|---|---|---|---|---|---|---|
| A | Adenine | C | Cytosine | G | Guanine | T | Thymine |
| U | Uracil | | | | | | |

| Degenerate nucleotide codes in addition to the five above codes: | | | | | | | |
|---|---|---|---|---|---|---|---|
| N | any (A/C/G/T) | R | puRine (G/A) | Y | pYrimidine (T/C) | K | Keto (G/T) |
| M | aMino (A/C) | S | Strong (G/C) | W | Weak (A/T) | B | not A (C/G/T) |
| D | not C (A/G/T) | H | not G (A/C/T) | V | not T (A/C/G) | | |

| Amino acids | | | | | | | |
|---|---|---|---|---|---|---|---|
| A | Alanine | C | Cysteine | D | Aspartate | E | Glutamate |
| F | Phenyl-alanine | G | Glycine | H | Histidine | I | Isoleucine |
| | | L | Leucine | M | Methionine | N | Asparagine |
| K | Lysine | Q | Glutamine | R | Arginine | S | Serine |
| P | Proline | V | Valine | W | Tryptophan | Y | Tyrosine |
| T | Threonine | | | | | | |

The invention provides a polypeptide or nucleic acid comprising or consisting of any one of amino acid or nucleotide sequences given in the sequence listing.

Definitions

The term "comprising" means "including" as well as "consisting" e.g. a composition "comprising" X may consist exclusively of X or may include something additional to X, such as X+Y.

A composition containing X is "substantially free of" Y when at least 85% by weight of the total X+Y in the composition is X. Preferably, X comprises at least about 90% by weight of the total of X+Y in the composition, more preferably at least about 95% or even 99% by weight. The term "heterologous" refers to two biological components that are not found together in nature. The components may be host cells, genes, or regulatory regions, such as promoters.

Although the heterologous components are not found together in nature, they can function together, as when a promoter heterologous to a gene is operably linked to the gene. Another example is where an influenza sequence is heterologous to a mouse host cell. Further examples would be two epitopes from the same or different proteins which have been assembled in a single protein in an arrangement not found in nature.

An "origin of replication" is a polynucleotide sequence that initiates and regulates replication of polynucleotides, such as an expression vector. The origin of replication behaves as an autonomous unit of polynucleotide replication within a cell, capable of replication under its own control. An origin of replication may be needed for a vector to replicate in a particular host cell. With certain origins of replication, an expression vector can be reproduced at a high copy number in the presence of the appropriate proteins within the cell. Examples of origins are the autonomously replicating sequences, which are effective in yeast; and the viral T-antigen, effective in COS-7 cells. A "mutant" sequence is defined as DNA, RNA or amino acid sequence differing from but having sequence identity with the native or disclosed sequence. Depending on the particular sequence, the degree of sequence identity between the native or disclosed sequence and the mutant sequence is preferably greater than 50% (e.g. 60%, 70%, 80%, 90%, 95%, 99% or more, calculated using the Smith-Waterman algorithm as described above). As used herein, an "allelic variant" of a nucleic acid molecule, or region, for which nucleic acid sequence is provided herein is a nucleic acid molecule, or region, that occurs essentially at the same locus in the genome of another or second isolate, and that, due to natural variation caused by, for example, mutation or recombination, has a similar but not identical nucleic acid sequence. A coding region allelic variant typically encodes a protein having similar activity to that of the protein encoded by the gene to which it is being compared. An allelic variant can also comprise an alteration in the 5' or 3' untranslated regions of the gene, such as in regulatory control regions (e.g. see U.S. Pat. No. 5,753,235).

Polypeptide Expression

Nucleotide sequences can be expressed in a variety of different expression systems; for example those used with mammalian cells, baculoviruses, plants, bacteria, and yeast.

Generally, any system or vector that is suitable to maintain, propagate or express nucleic acid molecules to produce a polypeptide in the required host may be used. The appropriate nucleotide sequence may be inserted into an expression system by any of a variety of well-known and routine techniques, such as, for example, those described in Sambrook et. al. Generally, the encoding gene can be placed under the control of a control element such as a promoter, ribosome binding site (for bacterial expression) and, optionally, an operator, so that the DNA sequence encoding the desired polypeptide is transcribed into RNA in the transformed host cell.

Examples of suitable expression systems include, for example, chromosomal, episomal and virus-derived systems, including, for example, vectors derived from: bacterial plasmids, bacteriophage, transposons, yeast episomes, insertion elements, yeast chromosomal elements, viruses such as baculoviruses, papova viruses such as SV40, vaccinia viruses, adenoviruses, fowl pox viruses, pseudorabies viruses and retroviruses, or combinations thereof, such as those derived from plasmid and bacteriophage genetic elements, including cosmids and phagemids. Human artificial chromosomes (HACs) may also be employed to deliver larger fragments of DNA than can be contained and expressed in a plasmid.

Particularly suitable expression systems include microorganisms such as bacteria transformed with recombinant bacteriophage, plasmid or cosmid DNA expression vectors; yeast transformed with yeast expression vectors; insect cell systems infected with virus expression vectors (for example, baculovirus); plant cell systems transformed with virus expression vectors (for example, cauliflower mosaic virus, CaMV; tobacco mosaic virus, TMV) or with bacterial expression vectors (for example, Ti or pBR322 plasmids); or animal cell systems. Cell-free translation systems can also be employed to produce the polypeptides of the invention.

Introduction of nucleic acid molecules encoding a polypeptide of the present invention into host cells can be effected by methods described in many standard laboratory manuals, such as Davis et al., Basic Methods in . Molecular Biology (1986) and Sambrook et al., (supra). Particularly suitable methods include calcium phosphate transfection, DEAE-dextran mediated transfection, transvection, microinjection, cationic lipid-mediated transfection, electroporation, transduction, scrape loading, ballistic introduction or infection (see Sambrook et al., 1989 [supra]; "Current Protocols in Molecular Biology", Ausubel et al. (eds). Greene Publishing Association and John Wiley lnterscience, New York, 1989, 1992; Spector, Goldman & Leinwald, 1998). In eukaryotic cells, expression systems may either be transient (for example, episomal) or permanent (chromosomal integration) according to the needs of the system.

For long-term, high-yield production of a recombinant polypeptide, stable expression is preferred. For example, cell lines which stably express the polypeptide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells that successfully express the introduced sequences. Resistant clones of stably transformed cells may be proliferated using tissue culture techniques appropriate to the cell type.

i. Mammalian Systems

Mammalian expression systems are known in the art. A mammalian promoter is any DNA sequence capable of binding mammalian RNA polymerase and initiating the downstream (3') transcription of a coding sequence (e.g. structural gene) into mRNA. A promoter will have a transcription initiating region, which is usually placed proximal to the 5' end of the coding sequence, and a TATA box, usually located 25-30 base pairs (bp) upstream of the transcription initiation site. The TATA box is thought to direct RNA polymerase II to begin RNA synthesis at the correct site. A mammalian promoter will also contain an upstream promoter element, usually located within 100 to 200 bp upstream of the TATA box. An upstream promoter element determines the rate at which transcription is initiated and can act in either orientation [Sambrook et al. (1989) "Expression of Cloned Genes in Mammalian Cells." In *Molecular Cloning: A Laboratory Manual, 2nd ed.]*.

Mammalian viral genes are often highly expressed and have a broad host range; therefore sequences encoding mammalian viral genes provide particularly useful promoter sequences. Examples include the SV40 early promoter, mouse mammary tumor virus LTR promoter, adenovirus major late promoter (Ad MLP), and herpes simplex virus promoter. In addition, sequences derived from non-viral genes, such as the murine metallotheionein gene, also provide useful promoter sequences. Expression may be either constitutive or regulated (inducible), depending on the promoter can be induced with glucocorticoid in hormone-responsive cells.

The presence of an enhancer element (enhancer), combined with the promoter elements described above, will usually increase expression levels. An enhancer is a regulatory DNA sequence that can stimulate transcription up to 1000-fold when linked to homologous or heterologous promoters, with synthesis beginning at the normal RNA start site. Enhancers are also active when they are placed upstream or downstream from the transcription initiation site, in either normal or flipped orientation, or at a distance of more than 1000 nucleotides from the promoter [Maniatis et al. (1987) *Science* 236:1237; Alberts et al. (1989) *Molecular Biology of the Cell, 2nd ed.*]. Enhancer elements derived from viruses may be particularly useful, because they usually have a broader host range. Examples include the SV40 early gene enhancer [Dijkema et al (1985) *EMBO J.* 4:761 ] and the enhancer/promoters derived from the long terminal repeat (LTR) of the Rous Sarcoma Virus [Gorman et al. (1982b) *PNAS USA* 79:6777] and from human cytomegalovirus [Boshart et al. (1985) *Cell* 41:521]. Additionally, some enhancers are regulatable and become active only in the presence of an inducer, such as a hormone or metal ion [Sassone-Corsi and Borelli (1986) *Trends Genel.* 2:215; Maniatis et al. (1987) *Science* 236:1237].

A DNA molecule may be expressed intracellularly in mammalian cells. A promoter sequence may be directly linked with the DNA molecule, in which case the first amino acid at the N-terminus of the recombinant protein will always be a methionine, which is encoded by the ATG start codon. If desired, the N-terminus may be cleaved by in vitro incubation with cyanogen bromide.

Alternatively, foreign proteins can also be secreted from the cell into the growth media by creating chimeric DNA molecules that encode a fusion protein comprised of a leader sequence fragment that provides for secretion of the foreign protein in mammalian cells. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell. The adenovirus triparite leader is an example of a leader sequence that provides for secretion of a foreign protein in mammalian cells.

Usually, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-transcriptional cleavage and polyadenylation [Birnstiel et al. (1985) Cell 41:349; Proudfoot and Whitelaw (1988) "Termination and 3' end processing of eukaryotic RNA. In *Transcription and splicing* (ed. B. D. Hames and D. M. Glover); Proudfoot (1989) *Trends Biochem. Sci.* 14:105]. These sequences direct the transcription of an mRNA which can be translated into the polypeptide encoded by the DNA. Examples of transcription terminater/polyadenylation signals include those derived from SV40 [Sambrook et al (1989) "Expression of cloned genes in cultured mammalian cells." In *Molecular Cloning: A Laboratory Manual]*.

Usually, the above described components, comprising a promoter, polyadenylation signal, and transcription termination sequence are put together into expression constructs. Enhancers, introns with functional splice donor and acceptor sites, and leader sequences may also be included in an expression construct, if desired. Expression constructs are often maintained in a replicon, such as an extrachromosomal element (e.g. plasmids) capable of stable maintenance in a host, such as mammalian cells or bacteria. Mammalian replication systems include those derived from animal viruses, which require trans-acting factors to replicate. For example, plasmids containing the replication systems of papovaviruses, such as SV40 [Gluzman (1981) *Cell* 23:175] or polyomavirus, replicate to extremely high copy number in the presence of the appropriate viral T antigen. Additional examples of mammalian replicons include those derived from bovine papillomavirus and Epstein-Barr virus. Additionally, the replicon may have two replicaton systems, thus allowing it to be maintained, for example, in mammalian cells for expression and in a prokaryotic host for cloning and amplification. Examples of such mammalian-bacteria shuttle vectors include pMT2 [Kaufman et al. (1989) *Mol. Cell. Biol.* 9:946] and pHEBO [Shimizu et al. (1986) *Mol Cell. Biol.* 6:1074].

The transformation procedure used depends upon the host to be transformed. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are known in the art and include many immortalised cell lines available from the American Type Culture Collection (ATCC) including, but not limited to, Chinese hamster ovary (CHO), HeLa, baby hamster kidney (BHK), monkey kidney (COS), C127, 3T3, BHK, HEK 293, Bowes melanoma and human hepatocellular carcinoma (for example Hep G2) cells and a number of other cell lines.

ii. Baculovirus Systems

The polynucleotide encoding the protein can also be inserted into a suitable insect expression vector, and is operably linked to the control elements within that vector. Vector construction employs techniques which are known in the art. Generally, the components of the expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene in to the baculovirus genome); and appropriate insect host cells and growth media.

After inserting the DNA sequence encoding the protein into the transfer vector, the vector and the wild type viral genome are transfected into an insect host cell where the vector and viral genome are allowed to recombine. The packaged recombinant virus is expressed and recombinant plaques are identified and purified. Materials and methods for baculovirus/insect cell expression systems are commercially available in kit form e.g. from Invitrogen, San Diego Calif. ("MaxBac" kit). These techniques are generally known to those skilled in the art and fully described in Summers & Smith, *Texas Agricultural Experiment Station Bulletin No. 1555* (1987) (hereinafter "Summers & Smith").

Prior to inserting the DNA sequence encoding the protein into the baculovirus genome, the above described components, comprising a promoter, leader (if desired), coding sequence of interest, and transcription termination sequence, are usually assembled into an intermediate transplacement construct (transfer vector). This construct may contain a single gene and operably linked regulatory elements; multiple genes, each with its owned set of operably linked regulatory elements; or multiple genes, regulated by the same set of regulatory elements. Intermediate transplacement constructs are often maintained in a replicon, such as an extrachromosomal element (e.g. plasmids) capable of stable maintenance in a host, such as a bacterium. The replicon will have a replication system, thus allowing it to be maintained in a suitable host for cloning and amplification.

Currently, the most commonly used transfer vector for introducing foreign genes into AcNPV is pAc373.Many other vectors, known to those of skill in the art, have also been designed. These include, for example, pVL985 (which alters the polyhedrin start codon from ATG to ATT, and which introduces a BamHI cloning site 32 basepairs downstream from the ATT; see Luckow and Summers, Virology (1989) 17:31.

The plasmid usually also contains a polyhedrin polyadenylation signal (Miller (1988) *Ann. Rev. Microbiol.* 42:177) and a prokaryotic ampicillin-resistance (amp) gene and origin of replication for selection and propagation in *E.coli*.

Baculovirus transfer vectors usually contain a baculovirus promoter. A baculovirus promoter is any DNA sequence capable of binding a baculovirus RNA polymerase and initiating the downstream (5' to 3') transcription of a coding sequence (e.g. structural gene) into mRNA. A promoter will have a transcription initiation region which is usually placed proximal to the 5' end of the coding sequence. This transcription initiation region usually includes an RNA polymerase binding site and a transcription initiation site. A baculovirus transfer vector may also have a second domain called an enhancer, which, if present, is usually distal to the structural gene. Expression may be either regulated or constitutive.

Structural genes, abundantly transcribed at late times in a viral infection cycle, provide particularly useful promoter sequences. Examples include sequences derived from the gene encoding the viral polyhedron protein, Friesen et al., (1986) "The Regulation of Baculovirus Gene Expression," in *The Molecular Biology of Baculoviruses* (ed. Walter Doerfler); EP-127839 & EP-155476; and the gene encoding the p10 protein, Vlak et al. (1988), *J Gen. Virol.* 69:765.

DNA encoding suitable signal sequences can be derived from genes for secreted insect or baculovirus proteins, such as the baculovirus polyhedrin gene (Carbonell et al. (1988) *Gene,* 73:409). Alternatively, since the signals for mammalian cell posttranslational modifications (such as signal peptide cleavage, proteolytic cleavage, and phosphorylation) appear to be recognized by insect cells, and the signals required for secretion and nuclear accumulation also appear to be conserved between the invertebrate cells and vertebrate cells, leaders of non-insect origin, such as those derived from genes encoding human □-inteferon, Maeda et al., (1985), *Nature* 315:592; human gastrin-releasing peptide, Lebacq-Verheyden et al., (1988), *Molec. Cell Biol.* 8:3129; human IL-2, Smith et al., (1985) *Proc. Nat'l Acad Sci. USA,* 82:8404; mouse IL-3, (Miyajima et al., (1987) Gene 58:273; and human glucocerebrosidase, Martin et al. (1988) *DNA,* 7:99, can also be used to provide for secretion in insects.

A recombinant polypeptide or polyprotein may be expressed intracellularly or, if it is expressed with the proper regulatory sequences, it can be secreted. Good intracellular expression of nonfused foreign proteins usually requires heterologous genes that ideally have a short leader sequence containing suitable translation initiation signals preceding an ATG start signal. If desired, methionine at the N-terminus may be cleaved from the mature protein by in vitro incubation with cyanogen bromide.

Alternatively, recombinant polyproteins or proteins which are not naturally secreted can be secreted from the insect cell by creating chimeric DNA molecules that encode a fusion protein comprised of a leader sequence fragment that provides for secretion of the foreign protein in insects. The leader sequence fragment usually encodes a signal peptide comprised of hydrophobic amino acids which direct the translocation of the protein into the endoplasmic reticulum.

After insertion of the DNA sequence and/or the gene encoding the expression product precursor of the protein, an insect cell host is co-transformed with the heterologous DNA of the transfer vector and the genomic DNA of wild type baculovirus—usually by co-transfection. The promoter and transcription termination sequence of the construct will usually comprise a 2-5kb section of the baculovirus genome. Methods for introducing heterologous DNA into the desired site in the baculovirus virus are known in the art. (See Summers & Smith supra; Ju et al. (1987); Smith et al., *Mol. Cell Biol.* (1983) 3:2156; and Luckow and Summers (1989)). For example, the insertion can be into a gene such as the polyhedrin gene, by homologous double crossover recombination; insertion can also be into a restriction enzyme site engineered into the desired baculovirus gene. Miller et al., (1989), *Bioessoys* 4:91.The DNA sequence, when cloned in place of the polyhedrin gene in the expression vector, is flanked both 5' and 3' by polyhedrin-specific sequences and is positioned downstream of the polyhedrin promoter.

The newly formed baculovirus expression vector is subsequently packaged into an infectious recombinant baculovirus. Homologous recombination occurs at low frequency (between about 1% and about 5%); thus, the majority of the virus produced after cotransfection is still wild-type virus. Therefore, a method is necessary to identify recombinant viruses. An advantage of the expression system is a visual screen allowing recombinant viruses to be distinguished. The polyhedrin protein, which is produced by the native virus, is produced at very high levels in the nuclei of infected cells at late times after viral infection. Accumulated polyhedrin protein forms occlusion bodies that also contain embedded particles. These occlusion bodies, up to 15 □m in size, are highly refractile, giving them a bright shiny appearance that is readily visualized under the light microscope. Cells infected with recombinant viruses lack occlusion bodies. To distinguish recombinant virus from wild-type virus, the transfection supernatant is plaqued onto a monolayer of insect cells by techniques known to those skilled in the art. Namely, the plaques are screened under the light microscope for the presence (indicative of wild-type virus) or absence (indicative of recombinant virus) of occlusion bodies. *Current Protocols in Microbiology Vol.* 2 (Ausubel et al. eds) at 16.8 (Supp. 10,1990); Summers & Smith, supra; Miller et al. (1989). Recombinant baculovirus expression vectors have been developed for infection into several insect cells. For example, recombinant baculoviruses have been developed for, inter alia: *Aedes aegypli, Aulographa californica, Bombyx mori, Drosophila melanogaster, Spodoplera frugiperda, and Trichoplusia ni (WO* 89/046699; Carbonell et al., (1985) J Virol. 56:153; Wright (1986) *Nature* 321:718; Smith et al., (1983) *Mol. Cell Biol* 3:2156; and see generally, Fraser, et al. (1989) *In Vitro Cell. Dev. Biol.* 25:225).

Cells and cell culture media are commercially available for both direct and fusion expression of heterologous polypeptides in a baculovirus/expression system; cell culture technology is generally known to those skilled in the art. See, e.g. Summers & Smith supra.

The modified insect cells may then be grown in an appropriate nutrient medium, which allows for stable maintenance of the plasmid(s) present in the modified insect host. Where the expression product gene is under inducible control, the host may be grown to high density, and expression induced. Alternatively, where expression is constitutive, the product will be continuously expressed into the medium and the nutrient medium must be continuously circulated, while removing the product of interest and augmenting depleted nutrients. The product may be purified by such techniques as chromatography, e.g. HPLC, affinity chromatography, ion exchange chromatography, etc.; electrophoresis; density gradient centrifugation; solvent extraction, or the like. As appropriate, the product may be further purified, as required, so as to remove substantially any insect proteins which are also secreted in the medium or result from lysis of insect cells, so as to provide a product which is at least substantially free of host debris, e.g. proteins, lipids and polysaccharides.

In order to obtain protein expression, recombinant host cells derived from the transformants are incubated under conditions which allow expression of the recombinant protein encoding sequence. These conditions will vary, dependent upon the host cell selected. However, the conditions are readily ascertainable to those of ordinary skill in the art, based upon what is known in the art.

iii. Plant Systems

There are many plant cell culture and whole plant genetic expression systems known in the art. Exemplary plant cellular genetic expression systems include those described in patents, such as: U.S. Pat. No. 5,693,506; U.S. Pat. No. 5,659,122; and U.S. Pat. No. 5,608,143. Additional examples of genetic expression in plant cell culture has been described by Zenk, *Phylochemistry* 30:3861-3863 (1991). Descriptions of plant protein signal peptides may be found in addition to the references described above in Vaulcombe et al., *Mol. Gen. Genel.* 209:33-40 (1987); Chandler et al., *Plant Molecular Biology* 3:407-418 (1984); Rogers, *J Biol. Chem.* 260:3731-3738 (1985); Rothstein et al., Gene 55:353-356 (1987); Whittier et al., Nucleic Acids Research 15:2515-2535 (1987); Wirsel et al., *Molecular Microbiology* 3:3-14 (1989); Yu et al., Gene 122:247-253 (1992). A description of the regulation of plant gene expression by the phytohormone, gibberellic acid and secreted enzymes induced by gibberellic acid can be found in R. L. Jones and J. MacMillin, Gibberellins: in: *Advanced Plant Physiology*, Malcolm B. Wilkins, ed., 1984 Pitman Publishing Limited, London, pp. 21-52. References that describe other metabolically-regulated genes: Sheen, *Plant Cell,* 2:1027-1038(1990); Maas et al., *EMBO J.* 9:3447-3452 (1990); Benkel & Hickey, *PNAS USA* 84:1337-1339 (1987) Typically, using techniques known in the art, a desired polynucleotide sequence is inserted into an expression cassette comprising genetic regulatory elements designed for operation in plants. The expression cassette is inserted into a desired expression vector with companion sequences upstream and downstream from the expression cassette suitable for expression in a plant host. The companion sequences will be of plasmid or viral origin and provide necessary characteristics to the vector to permit the vectors to move DNA from an original cloning host, such as bacteria, to the desired plant host. The basic bacterial/plant vector construct will preferably provide a broad host range prokaryote replication origin; a prokaryote selectable marker, and, for Agrobacterium transformations, T DNA sequences for Agrobacterium-mediated transfer to plant chromosomes. Where the heterologous gene is not readily amenable to detection, the construct will preferably also have a selectable marker gene suitable for determining if a plant cell has been transformed. A general review of suitable markers, e.g. for the members of the grass family, is found in Wilmink & Dons, 1993, *Plant Mol. Biol. Reptr,* 11(2):165-185.

Sequences suitable for permitting integration of the heterologous sequence into the plant genome are also recommended. These might include transposon sequences and the like for homologous recombination as well as Ti sequences which permit random insertion of a heterologous expression cassette into a plant genome. Suitable prokaryote selectable markers include resistance toward antibiotics such as ampicillin or tetracycline. Other DNA sequences encoding additional functions may also be present in the vector, as is known in the art.

The nucleic acid molecules of the subject invention may be included into an expression cassette for expression of the protein(s) of interest. Usually, there will be only one expression cassette, although two or more are feasible. The recombinant expression cassette will contain in addition to the heterologous protein encoding sequence the following elements, a promoter region, plant 5' untranslated sequences, initiation codon depending upon whether or not the structural gene comes equipped with one, and a transcription and translation termination sequence. Unique restriction enzyme sites at the 5' and 3' ends of the cassette allow for easy insertion into a pre-existing vector.

A heterologous coding sequence may be for any protein relating to the present invention. The sequence encoding the protein of interest will encode a signal peptide which allows processing and translocation of the protein, as appropriate, and will usually lack any sequence which might result in the binding of the desired protein of the invention to a membrane. Since, for the most part, the transcriptional initiation region will be for a gene which is expressed and translocated during germination, by employing the signal peptide which provides for translocation, one may also provide for translocation of the protein of interest. In this way, the protein(s) of interest will be translocated from the cells in which they are expressed and may be efficiently harvested. Typically secretion in seeds are across the aleurone or scutellar epithelium layer into the endosperm of the seed. While it is not required that the protein be secreted from the cells in which the protein is produced, this facilitates the isolation and purification of the recombinant protein.

Since the ultimate expression of the desired gene product will be in a eucaryotic cell it is desirable to determine whether any portion of the cloned gene contains sequences which will be processed out as introns by the host's splicosome machinery. If so, site-directed mutagenesis of the "intron" region may be conducted to prevent losing a portion of the genetic message as a false intron code, Reed and Maniatis, *Cell* 41:95-105, 1985.

The vector can be microinjected directly into plant cells by use of micropipettes to mechanically transfer the recombinant DNA. Crossway, *Mol. Gen Genet,* 202:179-185, 1985. The genetic material may also be transferred into the plant cell by using polyethylene glycol, Krens, et al., *Nature,* 296, 72-74, 1982. Another method of introduction of nucleic acid segments is high velocity ballistic penetration by small particles with the nucleic acid either within the matrix of small beads or particles, or on the surface, Klein, et al., *Nature,* 327, 70-73, 1987 and Knudsen and Muller, 1991, *Planta,* 185:330-336 teaching particle bombardment of barley endosperm to create transgenic barley. Yet another method of introduction would be fusion of protoplasts with other entities, either minicells, cells, lysosomes or other fusible lipid-surfaced bodies, Fraley, et al., *PNAS USA,* 79, 1859-1863, 1982.

The vector may also be introduced into the plant cells by electroporation. (Fromm et al., *PNAS USA* 82:5824, 1985). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus.

All plants from which protoplasts can be isolated and cultured to give whole regenerated plants can be transformed by the present invention so that whole plants are recovered which contain the transferred gene. It is known that practically all plants can be regenerated from cultured cells or tissues, including but not limited to all major species of sugarcane, sugar beet, cotton, fruit and other trees, legumes and vegetables. Some suitable plants include, for example, species from the genera *Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Dalura, Hyoscyamus, Lycopersion, Nicotiana, Solanum, Petunia, Digitalis, Majorana, Cichorium, Helianthus, Lactuca, Bromus, Asparagus, Antirrhinum, Hererocallis, Nemesia, Pelargonium, Panicum, Pennisetum, Ranunculus, Senecio, Solpiglossis, Cucumis, Browaalia, Glycine, Lolium, Zea, Triticum, Sorghum, and Datura.*

Means for regeneration vary from species to species of plants, but generally a suspension of transformed protoplasts containing copies of the heterologous gene is first provided. Callus tissue is formed and shoots may be induced from callus and subsequently rooted. Alternatively, embryo formation can be induced from the protoplast suspension. These embryos germinate as natural embryos to form plants. The culture media will generally contain various amino acids and hormones, such as auxin and cytokinins. It is also advantageous to add glutamic acid and proline to the medium, especially for such species as corn and alfalfa. Shoots and roots normally develop simultaneously. Efficient regeneration will depend on the medium, on the genotype, and on the history of the culture. If these three variables are controlled, then regeneration is fully reproducible and repeatable.

In some plant cell culture systems, the desired protein of the invention may be excreted or alternatively, the protein may be extracted from the whole plant. Where the desired protein of the invention is secreted into the medium, it may be collected. Alternatively, the embryos and embryoless-half seeds or other plant tissue may be mechanically disrupted to release any secreted protein between cells and tissues. The mixture may be suspended in a buffer solution to retrieve soluble proteins. Conventional protein isolation and purification methods will be then used to purify the recombinant protein. Parameters of time, temperature pH, oxygen, and volumes will be adjusted through routine methods to optimize expression and recovery of heterologous protein.

iv. Bacterial Systems

Bacterial expression techniques are known in the art. A bacterial promoter is any DNA sequence capable of binding bacterial RNA polymerase and initiating the downstream (3') transcription of a coding sequence (e.g. structural gene) into mRNA. A promoter will have a transcription initiation region which is usually placed proximal to the 5' end of the coding sequence. This transcription initiation region usually includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *E.coli* [Raibaud et al. (1984) *Annu. Rev. Genel.* 18:173]. Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) [Chang et al. (1977) *Nature* 198:1056], and maltose. Additional examples include promoter sequences derived from biosynthetic enzymes such as tryptophan (trp) [Goeddel et al. (1980) *Nuc. Acids Res.* 8:4057; Yelverton et al. (1981) *Nucl Acids Res.* 9:731; U.S. Pat. No. 4,738,921; EP-A-0036776 and EP-A-0121775]. The g-lactamase (bla) promoter system [Weissmann (1981) "The cloning of interferon and other mistakes." In *Interferon* 3 (ed. I. Gresser)], bacteriophage lambda PL [Shimatake et al. (1981) *Nature* 292:128] and T5 [U.S. Pat. No. 4,689,406] promoter systems also provide useful promoter sequences.

In addition, synthetic promoters which do not occur in nature also function as bacterial promoters. For example, transcription activation sequences of a bacterial or bacteriophage promoter may be joined with the operon sequences of another bacterial or bacteriophage promoter, creating a synthetic hybrid promoter [U.S. Pat. No. 4,551,433]. For example, the tac promoter is a hybrid trp-lac promoter comprised of both trp promoter and lac operon sequences that is regulated by the lac repressor [Amann et al. (1983) *Gene* 25:167; de Boer el al. (1983) *PNAS USA* 80:21]. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system [Studier et al. (1986) *J.Mol.Biol.* 189:113; Tabor et al. (1985) *PNAS USA* 82:1074]. In addition, a hybrid promoter can also be comprised of a bacteriophage promoter and an *E.coli* operator region (EP-A-0267851).

In addition to a functioning promoter sequence, an efficient ribosome binding site is also useful for the expression of foreign genes in prokaryotes. In *E.coli* the ribosome binding site is called the Shine-Dalgamo (SD) sequence and includes an initiation codon (ATG) and a sequence 3-9 nucleotides in length located 3-11 nucleotides upstream of the initiation codon [Shine et al. (1975) *Nature* 254:34]. The SD sequence is thought to promote binding of mRNA to the ribosome by base-pairing between the SD sequence and the 3' end of 16S rRNA [Steitz et al. (1979) "Genetic signals and nucleotide sequences in messenger RNA." In Biological Regulation and Development: Gene Expression (ed. R.F. Goldberger)]. To express eukaryotic genes and prokaryotic genes with weak ribosome-binding site [Sambrook et a. (1989) "Expression of cloned genes in Escherichia coli." In *Molecular Cloning: A Laboratory Manual].*

A DNA molecule may be expressed intracellularly. A promoter sequence may be directly linked with the DNA molecule, in which case the first amino acid at the N-terminus will always be a methionine, which is encoded by the ATG start codon. If desired, methionine at the N-terminus may be cleaved from the protein by in vitro incubation with cyanogen bromide or by either in vivo on in vitro incubation with a bacterial methionine N-terminal peptidase (EPO-A-0 219 237).

Fusion proteins provide an alternative to direct expression. Usually, a DNA sequence encoding the N-terminal portion of an endogenous bacterial protein, or other stable protein, is fused to the 5' end of heterologous coding sequences. Upon expression, this construct will provide a fusion of the two amino acid sequences. For example, the bacteriophage lambda cell gene can be linked at the 5'terminus of a foreign gene and expressed in bacteria. The resulting fusion protein preferably retains a site for a processing enzyme (factor Xa) to cleave the bacteriophage protein from the foreign gene [Nagai et al. (1984) *Nature* 309:810]. Fusion proteins can also be made with sequences from the lacZ [Jia et al. (1987) *Gene* 60:197], trpE [Allen et al. (1987) *J. Biotechnol.* 5:93; Makoffet et al. (1989) *J. Gen Microbiol.* 135:11], and *Chey* [EP-A-0 324 647] genes. The DNA sequence at the junction of the two amino acid sequences may or may not encode a cleavable site. Another example is a ubiquitin fusion protein. Such a fusion protein is made with the ubiquitin region that preferably retains a site for a processing enzyme (e.g. ubiquitin specific processing-protease) to cleave the ubiquitin from the foreign protein. Through this method, native foreign protein can be isolated [Miller et al. (1989) *Bio/Technology* 7:698].

Alternatively, foreign proteins can also be secreted from the cell by creating chimeric DNA molecules that encode a fusion protein comprised of a signal peptide sequence fragment that provides for secretion of the foreign protein in bacteria [U.S. Pat. No. 4,336,336]. The signal sequence fragment usually encodes a signal peptide comprised of hydrophobic amino acids which direct the secretion of the protein from the cell. The protein is either secreted into the growth media (gram-positive bacteria) or into the periplasmic space, located between the inner and outer membrane of the cell (gram-negative bacteria). Preferably there are processing sites, which can be cleaved either in vivo or in vitro encoded between the signal peptide fragment and the foreign gene.

DNA encoding suitable signal sequences can be derived from genes for secreted bacterial proteins, such as *E.coli* outer membrane protein gene (ompA) [Masui et al. (1983) in: *Experimental Manipulation of Gene Expression*; Ghrayeb et al. (1984) *EMBO J* 3:2437] and the *E.coli* alkaline phosphatase signal sequence (phoA) [Oka et al. (1985) PNAS USA 82:7212]. As a further example, signal sequence of the alpha-amylase gene from various Bacillus strains can be used to secrete heterologous proteins from *B.subtilis* [Palva et al. (1982) PNAS USA 79:5582; EP-A-02440421].

Usually, transcription termination sequences recognized by bacteria are regulatory regions located 3' to the translation stop codon, and thus together with the promoter flank the coding sequence. These sequences direct the transcription of an mRNA which can be translated into the polypeptide encoded by the DNA. Transcription termination sequences frequently include DNA sequences of about 50 nucleotides capable of forming stem loop structures that aid in terminating transcription. Examples include transcription termination sequences derived from genes with strong promoters, such as the trp gene in *E.coli* as well as other biosynthetic genes.

Usually, the above described components, comprising a promoter, signal sequence (if desired), coding sequence of interest, and transcription termination sequence, are put together into expression constructs. Expression constructs are often maintained in a replicon, such as an extrachromosomal element (e.g. plasmids) capable of stable maintenance in a host, such as bacteria. The replicon will have a replication system, thus allowing it to be maintained in a prokaryotic host either for expression or for cloning and amplification. In addition, a replicon may be either a high or low copy number plasmid. A high copy number plasmid will generally have a copy number ranging from ~5 to ~200, and usually ~10 to ~150.A host containing a high copy number plasmid will preferably contain at least ~10, and more preferably at least ~20 plasmids. Either a high or low copy number vector may be selected, depending upon the effect of the vector and the foreign protein on the host.

Alternatively, the expression constructs can be integrated into the bacterial genome with an integrating vector. Integrating vectors usually contain at least one sequence homologous to the bacterial chromosome that allows the vector to integrate. Integrations appear to result from recombinations between homologous DNA in the vector and the bacterial chromosome. For example, integrating vectors constructed with DNA from various Bacillus strains integrate into the Bacillus chromosome (EP-A-01 27328). Integrating vectors may also be comprised of bacteriophage or transposon sequences.

Usually, extrachromosomal and integrating expression constructs may contain selectable markers to allow for the selection of bacterial strains that have been transformed. Selectable markers can be expressed in the bacterial host and may include genes which render bacteria resistant to drugs such as ampicillin, chloramphenicol, erythromycin, kanamycin (neomycin), and tetracycline [Davies et al. (1978) *Annu. Rev. Microbiol.* 32:469]. Selectable markers may also include biosynthetic genes, such as those in the histidine, tryptophan, and leucine biosynthetic pathways.

Alternatively, some of the above described components can be put together in transformation vectors. Transformation vectors are usually comprised of a selectable market that is either maintained in a replicon or developed into an integrating vector, as described above.

Expression and transformation vectors, either extra-chromosomal replicons or integrating vectors, have been developed for transformation into many bacteria. For example, expression vectors have been developed for, inter alia, the following bacteria: Bacillus subtilis [Palva et. al. (1982) *PNAS USA* 79:5582; EP-A-0 036 259 and EP-A-0 063 953; WO 84/04541], Escherichia coli [Shimatake et al. (1981) *Nature* 292:128; Amann el al. (1985) Gene 40:183; Studier et al. (1986) *J. Mol. Biol.* 189:113; EP-A-0 036 776,EP-A-0 136 829 and EP-A-0 136 907], Streptococcus cremoris [Powell et al. (1988) *Appl. Environ. Microbial.* 54:655]; Streptococcus lividans [Powell el al. (1988) *Appl. Environ Microbial.* 54:655], Streptomyces lividans [U.S. Pat. No. 4,745,056].

Methods of introducing exogenous DNA into bacterial hosts are well-known in the art, and usually include either the transformation of bacteria treated with $CaCl_2$ or other agents, such as divalent cations and DMSO. DNA can also be introduced into bacterial cells by electroporation. Transformation procedures usually vary with the bacterial species to be transformed. See e.g. [Masson et al. (1989) *FEMS Microbiol. Lett.* 60:273; Palva et al. (1982) *PNAS USA* 79:5582; EP-A-0 036 259 and EP-A-0 063 953; WO 84/04541, Bacillus], [Miller et al. (1988) *PNAS USA* 85:856; Wang el al. (1990) *J. Bacteriol.* 172:949, Campylobacter], [Cohen et al. (1973) *PNAS USA* 69:2110; Dower et al. (1988) *Nucleic Acids Res.* 16:6127; Kushner (1978) "An improved method for transformation of

*Escherichia coli* with ColE1-derived plasmids. In *Genetic Engineering: Proceedings of the International Symposium on Genetic Engineering* (eds. H.W. Boyer and S. Nicosia); Mandel et al. (1970)*J. Mol. Biol.* 53:159; Taketo (1988) *Biochim. Biophys. Acta* 949:318; Escherichia], [Chassy el al. (1987) *FEMS Microbiol. Lett.* 44:173 Lactobacillus]; [Fiedler et. al. (1988) *AnaL Biochem* 170:38, Pseudomonas]; [Augustin et al. (1990) *FEMS Microbiol. Lett.* 66:203, Staphylococcus], [Barany et al. (1980) *J. Bacteriol.* 144:698; Hariander (1987) "Transformation of Streptococcus lactis by electroporation, in: *Streptococcal Genetics* (ed. J. Ferretti and R. Curtiss III); Perry et al. (1981) *Infect. Immun* 32:1295; Powellet et al. (1988) *Appl. Environ. Microbiol.* 54:655; Somkutiet al. (1987) *Proc.* 4th *Evr. Cong. Biotechnology* 1:412, Streptococcus].

General guidance on expression in *E.coli* and its optimisation can be found in Baneyx (1999) *Curr.Opin.Biolech.* 10:411421 and Hannig & Makrides (1998) *TIBTECH* 16:54-60.

v. Yeast Expression

Yeast expression systems are also known to one of ordinary skill in the art. A yeast promoter is any DNA sequence capable of binding yeast RNA polymerase and initiating the downstream (3') transcription of a coding sequence (e.g. structural gene) into mRNA. A promoter will have a transcription initiation region which is usually placed proximal to the 5' end of the coding sequence. This transcription initiation region usually includes an RNA polymerase binding site (the "TATA Box") and a transcription initiation site. A yeast promoter may also have a second domain called an upstream activator sequence (UAS), which, if present, is usually distal to the structural gene. The UAS permits regulated (inducible) expression. Constitutive expression occurs in the absence of a UAS. Regulated expression may be either positive or negative, thereby either enhancing or reducing transcription.

Yeast is a fermenting organism with an active metabolic pathway, therefore sequences encoding enzymes in the metabolic pathway provide particularly useful promoter sequences. Examples include alcohol dehydrogenase (ADH) (EP-A-0284044), glucose-6-phosphate isomerase, glyceraldehyde-3-phosphate-dehydrogenase (GAP or GAPDH), hexokinase, phosphofructokinase, 3-phosphoglycerate mutase, enolase, glucokinase, and pyruvate kinase (PyK) (EPO-A-0329203). The yeast PHO5 gene, encoding acid phosphatase, also provides useful promoter sequences [Myanohara et al. (1983) *PNAS USA* 80:1].

In addition, synthetic promoters which do not occur in nature also function as yeast promoters. For example, UAS sequences of one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876, 197 and 4,880,734). Other examples of hybrid promoters include promoters which consist of the regulatory sequences of either the ADH2, GAL4, GAL10, OR PHO5 genes, combined with the transcriptional activation region of a glycolytic enzyme gene such as GAP or PyK (EP-A-0 164 556). Furthermore, a yeast promoter can include naturally occurring promoters of non-yeast origin that have the ability to bind yeast RNA polymerase and initiate transcription. Examples of such promoters include, inter alia, [Cohen et al. (1980) *PNAS USA* 77:1078; Henikoff et al. (1981) *Nature* 283:835; Hollenberg et al. (1981) *Curr. Topics Microbiol. Immunol.* 96:119; Hollenberg et al. (1979) "The Expression of Bacterial Antibiotic Resistance Genes in the Yeast Saccharomyces cerevisiae," in: *Plasmids of Medical, Environmental and Commercial Importance* (eds. K.N. Timmis and A. Puhler); Mercerau-Puigalon et al. (1980) Gene 11:163; Panthier et al. (1980) Curr. Genel 2:109;].

A DNA molecule may be expressed intracellularly in yeast. A promoter sequence may be directly linked with the DNA molecule, in which case the first amino acid at the N-terminus of the recombinant protein will always be a methionine, which is encoded by the ATG start codon. If desired, methionine at the N-terminus may be cleaved from the protein by in vitro incubation with cyanogen bromide.

Fusion proteins provide an alternative for yeast expression systems, as well as in mammalian, baculovirus, and bacterial expression systems. Usually, a DNA sequence encoding the N-terminal portion of an endogenous yeast protein, or other stable protein, is fused to the 5' end of heterologous coding sequences. Upon expression, this construct will provide a fusion of the two amino acid sequences. For example, the yeast or human superoxide dismutase (SOD) gene, can be linked at the 5' terminus of a foreign gene and expressed in yeast. The DNA sequence at the junction of the two amino acid sequences may or may not encode a cleavable site. See e.g. EP-A-0 196 056.Another example is a ubiquitin fusion protein. Such a fusion protein is made with the ubiquitin region that preferably retains a site for a processing enzyme (e.g. ubiquitin-specific processing protease) to cleave the ubiquitin from the foreign protein. Through this method, therefore, native foreign protein can be isolated (e.g. WO88/024066).

Alternatively, foreign proteins can also be secreted from the cell into the growth media by creating chimeric DNA molecules that encode a fusion protein comprised of a leader sequence fragment that provide for secretion in yeast of the foreign protein. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell.

DNA encoding suitable signal sequences can be derived from genes for secreted yeast proteins, such as the invertase gene (EP-A-0 012 873; JPO. 62,096,086) and the A-factor gene (U.S. Pat. No. 4,588,684). Alternatively, leaders of non-yeast origin, such as an interferon leader, exist that also provide for secretion in yeast (EP-A-0 060 057).

A preferred class of secretion leaders are those that employ a fragment of the yeast alpha-factor gene, which contains both a "pre" signal sequence, and a "pro" region. The types of alpha-factor fragments that can be employed include the full-length pre-pro alpha factor leader (about 83 aa residues) as well as truncated alpha-factor leaders (usually about 25 to about 50 amino acid residues) (U.S. Pat. No. 4,546,083 and 4,870,008; EP-A-0 324 274). Additional leaders employing an alpha-factor leader fragment that provides for secretion include hybrid alpha-factor leaders made with a presequence of a first yeast, but a pro-region from a second yeast alphafactor. (e.g. see WO 89/02463.)

Usually, transcription termination sequences recognized by yeast are regulatory regions located 3' to the translation stop codon, and thus together with the promoter flank the coding sequence. These sequences direct the transcription of an mRNA which can be translated into the polypeptide encoded by the DNA. Examples of transcription terminator sequence and other yeast-recognized termination sequences, such as those coding for glycolytic enzymes.

Usually, these components, comprising a promoter, leader (if desired), coding sequence of interest, and transcription termination sequence, are put together into expression constructs. Expression constructs are often maintained in a replicon, such as an extrachromosomal element (e.g. plasmids) capable of stable maintenance in a host, such as yeast or bacteria. The replicon may have two replication systems, thus allowing it to be maintained, for example, in yeast for expression and in a prokaryotic host for cloning and amplification. Examples of such yeast-bacteria shuttle vectors include YEp24 [Botsteinet et al. (1979) Gene 8:17-24], pCl/l [Brake et al. (1984) PNAS USA 81:4642-4646], and YRp17 [Stinchcomb et al. (1982) J. Mol. Biol. 158:157). In addition, a replicon may be either a high or low copy number plasmid. A high copy number plasmid will generally have a copy number ranging from ~5 to ~200, and usually ~10 to ~150.A host containing a high copy number plasmid will preferably have at least ~10, and more preferably at least ~20.Either a high or low copy number vector may be selected, depending upon the effect of the vector and the foreign protein on the host. See e.g. Brakeet et al., supra.

Alternatively, the expression constructs can be integrated into the yeast genome with an integrating vector. Integrating vectors usually contain at least one sequence homologous to a yeast chromosome that allows the vector to integrate, and preferably contain two homologous sequences flanking the expression construct. Integrations appear to result from recombinations between homologous DNA in the vector and the yeast chromosome [Orr-Weaver et al. (1983) Methods in Enzymol. 101:228-245]. An integrating vector may be directed to a specific locus in yeast by selecting the appropriate homologous sequence for inclusion in the vector. See Orr-Weaver et al., supra. One or more expression construct may integrate, possibly affecting levels of recombinant protein produced [Rine et al. (1983) PNAS USA 80:6750]. The chromosomal sequences included in the vector can occur either as a single segment in the vector, which results in the integration of the entire vector, or two segments homologous to adjacent segments in the chromosome and flanking the expression construct in the vector, which can result in the stable integration of only the expression construct.

Usually, extrachromosomal and integrating expression constructs may contain selectable markers to allow for the selection of yeast strains that have been transformed. Selectable markers may include biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a suitable selectable marker may also provide yeast with the ability to grow in the presence of toxic compounds, such as metal. For example, the presence of CUP1 allows yeast to grow in the presence of copper ions [Butt et al. (1987) Microbiol, Rev. 51:351].

Alternatively, some of the above described components can be put together into transformation vectors. Such vectors usually comprise a selectable marker that is either maintained in a replicon or developed into an integrating vector as described above. Expression and transformation vectors, either extrachromosomal replicons or integrating vectors, have been developed for transfomnation into many yeasts. For example, expression vectors have been developed for, inter alia, the following yeasts:Candida albicans [Kurtz, et al. (1986) Mol. Cell. Biol. 6:142], Candida maltosa [Kunze, et al. (1985) J. Basic Microbiol. 25:141]. Hansenula polymorpha [Gleeson, et al. (1986) J. Gen Microbiol. 132:3459; Roggenkamp et al. (1986) Mol. Gen. Genet. 202:302], Kluyveromyces fragilis [Das, et al. (1984) J. Bacteriol. 158:1165], Kluyveromyces lactis [De Louvencourt et al. (1983) J. Bacteriol. 154:737; Van den Berg et al. (1990) Bio/Technology 8:135], Pichia guillerimondii [Kunze et al. (1985) J. Basic Microbiol. 25:141], Pichia pastoris [Cregg, et al. (1985) Mol. Cell. Biol. 5:3376; U.S. Pat. Nos. 4,837,148 and 4,929,555,], Saccharomyces cerevisiae [Hinnen et al. (1978) PNAS USA 75:1929; Ito et al. (1983) J. Bacteriol. 153:163], Schizosaccharomyces pombe [Beach and Nurse (1981) Nature 300:706], and Yarrowia lipolytica [Davidow, et al. (1985) Curr. Genet. 10:380471 Gaillardin, et al. (1985) Curr. Genet. 10:49].

Methods of introducing exogenous DNA into yeast hosts are well-known in the art, and usually include either the transformation of spheroplasts or of intact yeast cells treated with alkali cations. Transformation procedures usually vary with the yeast species to be transformed. See e.g. [Kurtz et al. (1986) Mol. Cell. Biol. 6:142; Kunze et al. (1985) J. Basic Microbiol. 25:141; Candida]; [Gleeson et al. (1986) J. Gen Microbiol. 132:3459; Roggenkamp et al. (1986) Mol. Gen Genet. 202:302; Hansenula]; [Das et al. (1984) J. Bacteriol. 158:1165; De Louvencourt et al. (1983) J. Bacteriol. 154: 1165; Van den Berg et al. (1990) Bio/Technology 8:135; Kluyveromyces]; [Cregg et al. (1985) Mol. Cell. Biol. 5:3376; Kunze et al. (1985) J. Basic Microbiol. 25:141; U.S. Pat. Nos. 4,837,148 and 4,929,555; Pichia]; [Hinnen et al. (1978) PNAS USA 75;1929; Ito et al. (1983)J. Bacteriol. 153:163 Saccharomyces]; [Beach and Nurse (1981) Nature 300:706; Schizosaccharomyces]; [Davidow et al. (1985) Curr. Genet. 10:39; Gaillardin et al. (1985) Curr. Genet. 10:49; Yarrowia].

BRIEF DESCRIPTION OF DRAWINGS

FIG. 2 shows in vitro microbicidal activity by CFU assay of mAb K10 and mAb K20 in comparison with an irrelevant isotype-matched mAb (all at 100 μg/ml dose) against Candida albicans UP10S.

FIG. 3 shows in vitro microbicidal activity of scFv antibodies H6 and H20 (100 μg/ml dose).

FIG. 14 shows the effect of KM peptide (14A & 14B) on A.castellani growth, compared to the effect of SP peptide (14C & 14D). Growth was at either 37° C. (14A & 14C) or 25° C. (14B & 14D). The graphs show the number of trophozoites per well.

FIG. 15 shows the effect of KM peptide on *A.castellani* cell viability. SP peptide is set as 100%.

FIG. 20 shows the toxicity of KM (FIG. 20A) and SP (FIG. 20B) peptides. Cell viability was expressed as %T/C where T represents the mean absorbance of the treated cells and C the mean absorbance of the controls.

BRIEF DESCRIPTION OF THE SEQUENCE LISTING

Figure 1:
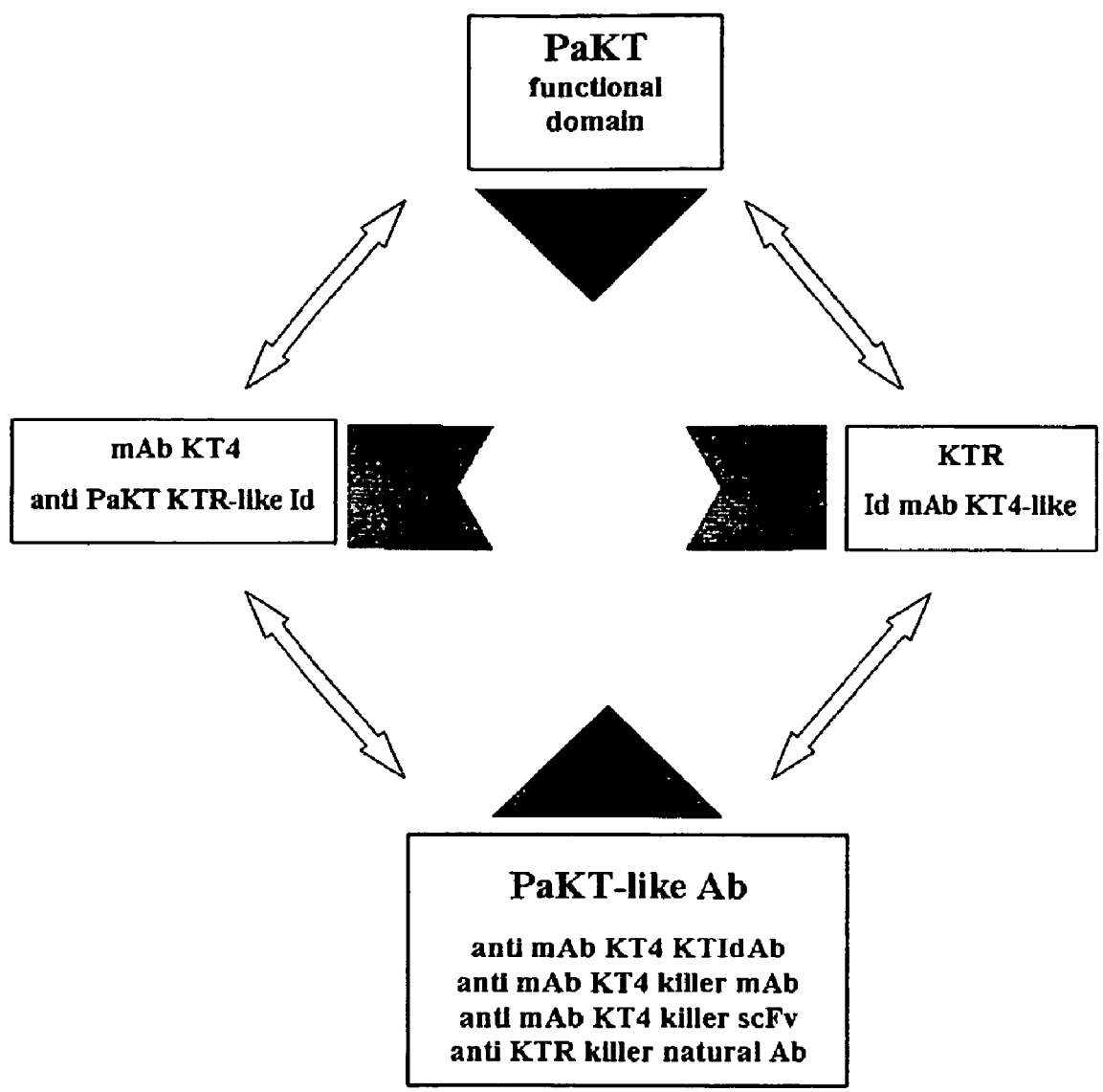
FIG. 1 shows structural and functional relationships of Pichia anomala killer toxin (PaKT), PaKT-neutralizing monoclonal antibody (mAb KT4), killer toxin receptor (KTR), and PaKT-like killer antibodies and derivative killer mimotopes (KM).

| SEQ ID | Description |
|---|---|
| 1 | Nucleotide sequence of H6 scFv |
| 2 | Amino acid sequence of H6 scFv |
| 3 | KM0 (fragment of SEQ ID 2) |
| 4 | KM (=SEQ ID 3 with Glu→Ala mutation at position 1) |
| 5-12 | Alanine-scanning variants of SEQ ID 3 |
| 13 | SP0 scramble peptide |
| 14-20 | Shortened derivatives of KM (9mer, 8mer, 7mer, 6mer, 5mer, 4mer, 3mer from SEQ ID 3) |
| 21 | Nucleotide sequence of H20 scFv |
| 22 | Amino acid sequence of H20 scFv |
| 23 | KM1 (=SEQ ID 3 with Cys→Ser mutation at position 7) |
| 24 | KM2 |
| 25 | KM3 |
| 26 | KM4 |
| 27 | KM5 |
| 28 | Irrelevant peptide IP |
| 29 | SP |
| 30 | Linker (used to join KM0 and KM2 to give KM3) |
| 31 | Peptide control |
| 32 | KM1 derivative (=SEQ ID 4 with Cys→Xaa mutation at position 7) |
| 33 | SEQ ID 32 with Cys→Ser mutation at position 7 |
| 34-38 | KM0, KM1, KM2, KM4 & KM5 equivalents from H20 |
| 39 | KM equivalent from H20 |
| 40-47 | Alanine-scanning variants of SEQ ID 24 |
| 48 | KM2 (SEQ ID 24) with Cys→Ser mutation at position 7 |
| 49-57 | Alanine-scanning variants of SEQ ID 27 |
| 58 | KM4 (SEQ ID 26) with Cys→Ser mutation at position 7 |
| 59 | C-terminus 'E-tag' from scFv system |
| 60-65 | CDRs from H6 antibody (fragments of SEQ ID 2) |
| 66-71 | CDRs from H20 antibody (fragments of SEQ ID 22) |

NB: the inclusion of a polypeptide sequence in the sequence listing does not imply any particular D- or L-configuration to its constituent amino acids.

MODES FOR CARRYING OUT THE INVENTION

H6 Single-chain Fv Antibody

H6 is a single-chain Fv raised against the idiotope of the KT4 monoclonal antibody. It is an anti-idiotypic antibody raised with the purpose of mimicking the activity of the *Pichia anomala* killer toxin (PaKT).

The existence of scFv H6 has previously been reported [e.g. ref. 13], but a method for its manufacture has not previously been disclosed, nor has its amino acid sequence. The sequence of H6 is now disclosed (SEQ IDs 1 and 2). Within SEQ ID 2, amino acids 107-132 (GT . . . IE) are a linker and the final 13 amino acids (GA . . . PR; SEQ ID 59) are the 'E-tag' inserted by the *Recombinant Phage Antibody System* (Pharmacia Biotech™) used to create the scFv.

The CDRs within H6 are as follows:

| CDR | aa | SEQ ID |
|---|---|---|
| H1 | 33-37 | 60 |
| H2 | 52-65 | 61 |
| H3 | 98-101 | 62 |
| L1 | 153-162 | 63 |
| L2 | 178-184 | 64 |
| L3 | 217-224 | 65 |

The H6 scFv has strong microbicidal effects in vitro against important pathogenic microorganisms including: *C.albicans; C.krusei* and *C. glabrata* (including fluconazole-resistant strains); *Cryptococcus neoformans; A. fumigatus; M.tuberculosis; S.aureus, Enterococcus faecalis, E.faecium,* and *Streptococcus pneumoniae* (including methicillin-, vancomycin- and penicillin-resistant strains); *S.mutans, Leishmania major, L.infantum* and *Achantamoeba castellani*. Furthermore, it shows specific therapeutic activity in an in vivo model of rat vaginal candidiasis by intravaginal administration.

K20 Monoclonal Antibody and scFv Derivative H20

K10 is an anti-idiotypic rat monoclonal antibody raised against KT4. Like the H6 scFv, it shows good in vitro microbicidal activity. In addition, it has been shown to be therapeutic against *P.carinii* pneumonia in rats infected by aerosol administration [16], and in mice transplanted with T cell depleted bone marrow against aspergillosis caused by nasal instillation [14].

Anti-idiotypic antibodies were raised in mice against K10 (i.e. anti-anti-anti-idiotypic with respect to PaKT). One of the resulting hybridoma-produced antibodies was designated 'K20'.

K20 was tested in a conventional in vitro colony forming unit (CFU) assay to evaluate killer activity. Approximately 250 viable PaKT-susceptible germinating *C.albicans* UP10 cells, suspended in 10 µl PBS, were added to 90 µl K20 to obtain a final concentration of 100 µg/ml and incubated for 6 h at 37° C. After incubation with the respective reagents, the fungal cells were dispensed and streaked on the surface of Sabouraud dextrose agar plates, which were therefore incubated at 30° C. and their colony forming units (CFU) enumerated after 48 hours. Each experiment was performed in triplicate. An irrelevant mAb was used as a control.

As shown in FIG. 2, K20 shows slightly better anti-candida activity than K10.

K20 was converted into a scFv antibody using the *Recombinant Phage Antibody System* (Pharmacia Biotech™). The scFv was designated 'H20' and its sequence is given as SEQ IDs 21 and 22. The H20 CDRs are as follows:

| CDR | aa | SEQ ID |
|---|---|---|
| H1 | 33-37 | 66 |
| H2 | 52-66 | 67 |
| H3 | 99-115 | 68 |
| L1 | 167-176 | 69 |
| L2 | 192-198 | 70 |
| L3 | 231-238 | 71 |

H20 was tested in the CFU assay (FIG. 3) and shows a candidacidal activity comparable to H6.

Active Fragments of H6

Short peptide fragments of H6 were synthesised, with emphasis on the CDR sequences.

Solid phase synthesis was carried out with a MultiSynTech Syro automatic peptide synthesizer (Witten, Germany) employing Fmoc chemistry with HOBt activation and Rink amide MBHA resin as solid support. Peptides were cleaved from the resins and deprotected by treatment with trifluoroacetic acid containing ethandithiol, water, triisobutylsilane and anisole (93/2.5/2/1.5/1). After precipitation by ethylic ether, peptides were purified by a Vydac C18 column (25 cm ×1cm) and characterized by amino acid analysis and mass spectrometry. The following peptides were synthesised:

| # | Name | SEQ ID | H6 residues | Based on CDR |
|---|------|--------|-------------|--------------|
| 1 | KM0  | 3      | 146-155     | L1           |
| 2 | KM2  | 24     | 91-100      | H3           |
| 3 | KM4  | 26     | 146-160     | L1           |
| 4 | KM5  | 27     | 155-163     | L1           |

These peptides were tested in the CFU assay to evaluate killer activity.

As a control, a 'scramble' peptide (SEQ ID 13; SP0') was synthesised in which the amino acids of KM0 were re-ordered to have the same overall peptide composition but different sequence. This was used in the above assay at the same concentration as the test KM peptides as a control for KM0 and KM4. For KM2, the control was SEQ ID 28 ('IP' or 'irrelevant peptide' ). For KM5, the control was SEQ ID 31.

Results with KM0 were as follows, expressed as % growth in comparison to the control:

| Peptide     | 100 µg/ml    | 25 µg/ml      | 6.25 µg/ml    |
|-------------|--------------|---------------|---------------|
| SP0 Control | 100          | 100           | 100           |
| KM0         | 5.69 ± 0.20  | 29.84 ± 10.63 | 67.13 ± 13.81 |

Figure 4:
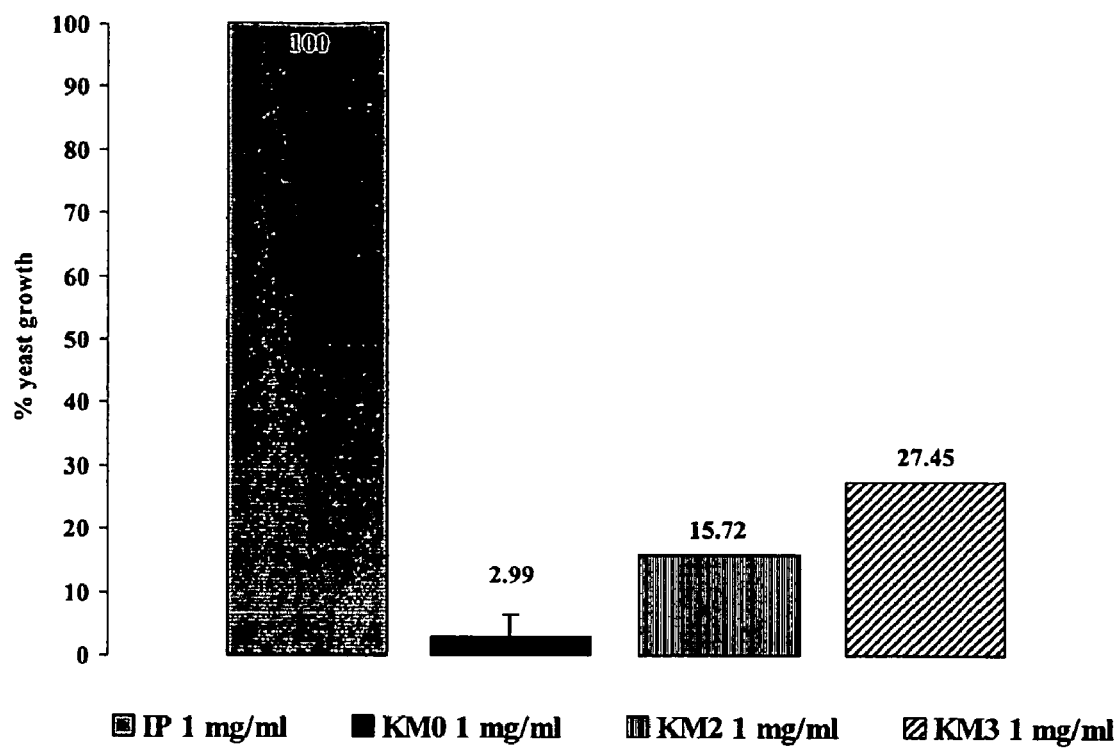
FIG. 4 shows in vitro microbicidal activity of peptides KM2 and KM3 compared to KM0 and IP controls (1 mg/ml dose).
Figure 5:
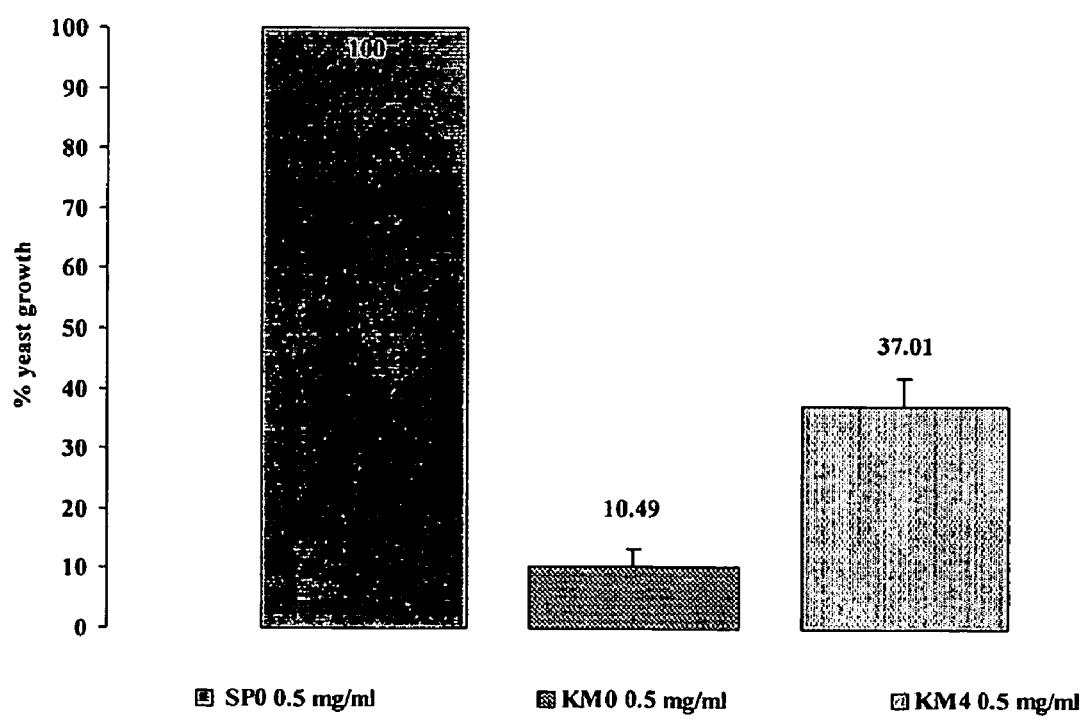
FIG. 5 shows in vitro microbicidal activity of KM4 (0.5 mg/ml dose).
Figure 6:
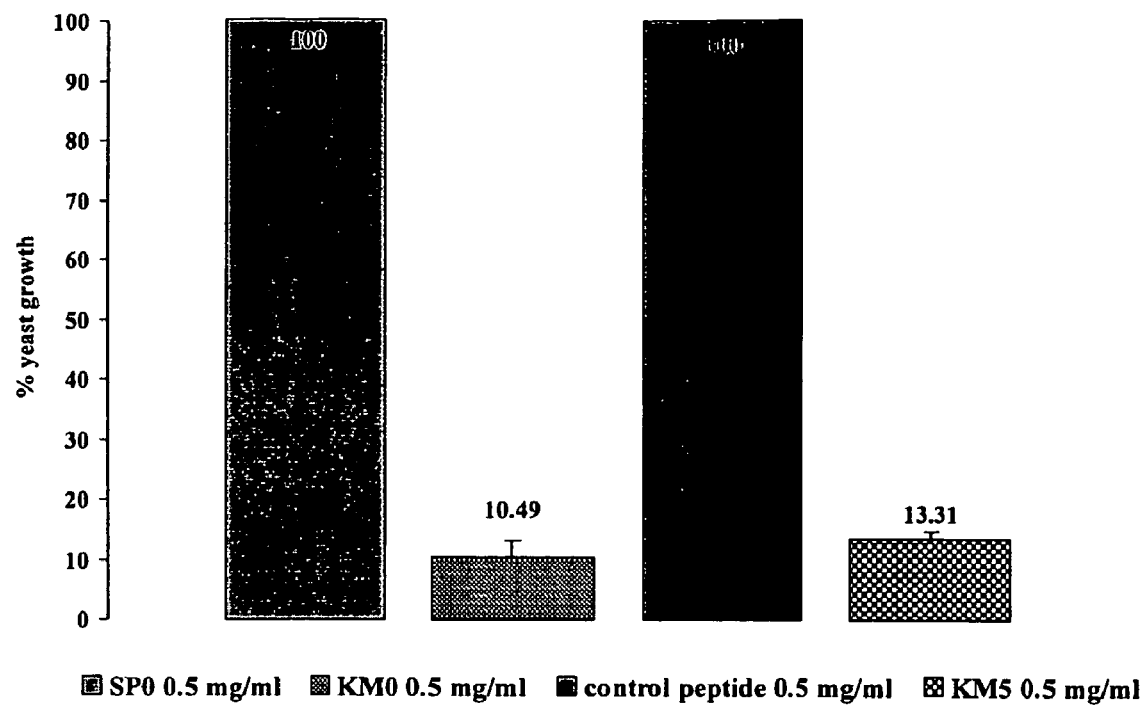
FIG. 6 shows in vitro microbicidal activity of KM5 (1 mg/ml dose).

Results with KM0, KM2, KM4 and KM5 at various concentrations are shown in FIGS. 4 to 6. KM0 & KM5 are thus extremely effective anti-candidal peptides. KM2 is also effective, and KM4 is moderately effective.

The CDRs of H6 were also prepared in isolated form (SEQ IDs 60-65) and tested for microbicidal activity in the *C.albicans* CFU assay. Each CDR peptide was tested at scalar dilutions to establish the $IC_{50}$. Assays were performed in triplicate and the $IC_{50}$ of each peptide was calculated by non-linear regression analysis of curves obtained by plotting the number of CFU versus Log peptide concentration. Results were as follows:

| Peptide      | $IC_{50}$ (mol/l)     | SEQ ID |
|--------------|-----------------------|--------|
| Heavy chain  |                       |        |
| CDR-1        | $2.67 \times 10^{-7}$ | 60     |
| CDR-2        | $1.17 \times 10^{-7}$ | 61     |
| CDR-3        | $1.09 \times 10^{-7}$ | 62     |
| Light chain  |                       |        |
| CDR-1        | $6.92 \times 10^{-7}$ | 63     |
| CDR-2        | $2.34 \times 10^{-7}$ | 64     |
| CDR-3        | $2.00 \times 10^{-7}$ | 65     |

The CDRs of H6 antibody therefore show significant anti-candida activity, with CDR-3 from the heavy chain (SEQ ID 62) showing the best activity.

Fragments of the H6 scFv are therefore able to act as microbicides even though they would not be expected to hold in the same tertiary conformation as in the intact antibody.

Polypeptides Comprising More Than One Fragment of H6

KM0 is derived from a H6 light chain CDR and KM2 is derived from a H6 heavy chain CDR. The two decapeptides, each of which has microbididal activity on its own, were linked by a glycine-rich sequence (SEQ ID 30) to give KM3 (SEQ ID 25).

In comparison to IP in the CFU assay, KM3 showed candidacidal activity, but this was weaker than either KM0 and KM2 alone (FIG. 4).

Substitution Within KM0-cysteine Replacement

Figure 7:
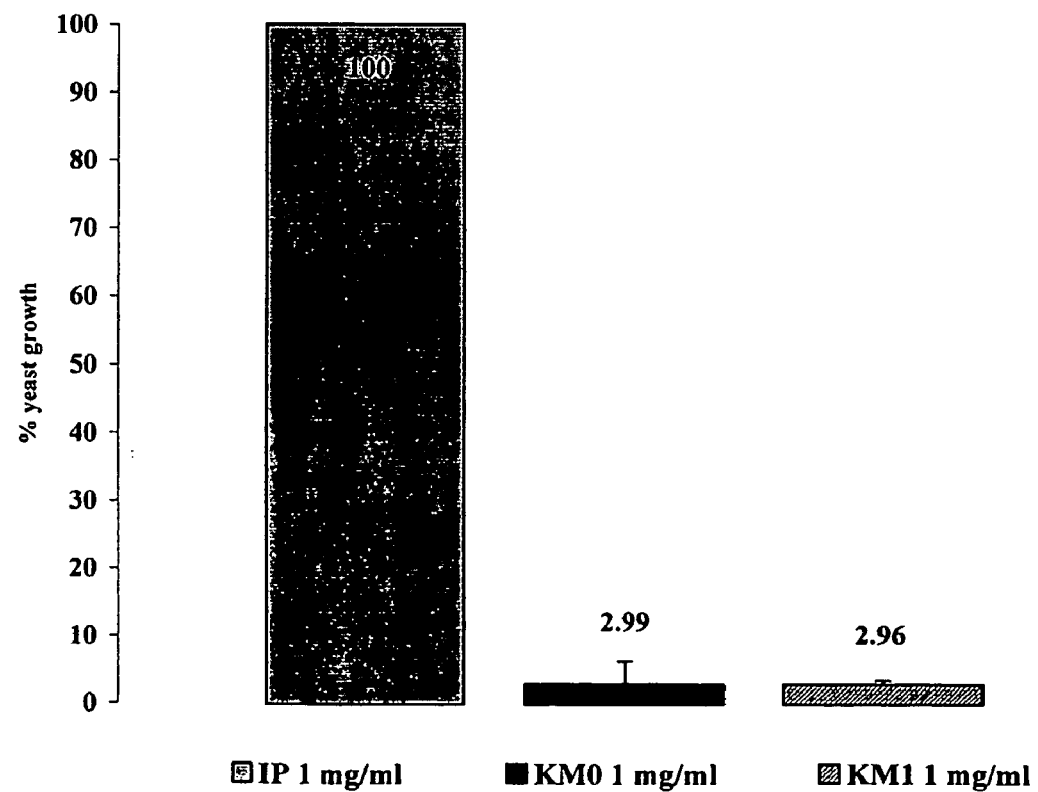
FIG. 7 shows in vitro microbicidal activity of KM1 (1 mg/ml dose).

The cysteine residue in decapeptide KM0 was substituted with serine to give KM1 (SEQ ID 23), with a view to reducing oxidation and polymerization processes. KM1 showed similar activity to KM0 in the CFU assay (FIG. 7) in comparison to the IP control. The substitution of cysteine with serine thus gave no apparent alteration of the antibiotic effect of KM0, but offers increased resistance to oxidation and thus increased in vivo half life.

SEQ ID 48 is a C→S substitution form of KM2. SEQ ID 58 is a C→S substitution form of KM4.

Substitution Within KM0-alanine Scanning

Decapeptide KM0 was analysed by alanine scanning [32] in order to identify the functional contributional of individual residues to its microbicidal activity. Each of the ten constituent amino acids was replaced with A (except for residue 9, which is already A) and activity in the in vitro CFU assay was assessed. Results were as follows, with values being % growth in comparison to the SP0 control:

| SEQ ID | 100 µg/ml      | 25 µg/ml      | 6.25 µg/ml    |
|--------|----------------|---------------|---------------|
| 3      | 5.69 ± 0.20    | 29.84 ± 10.63 | 67.13 ± 13.81 |
| 4      | 0              | 0             | 0             |
| 5      | 9.91 ± 3.28    | 42.67 ± 2.04  | 53.40 ± 6.99  |
| 6      | 9.27 ± 2.45    | 19.72 ± 2.91  | 60.06 ± 5.24  |
| 7      | 9.18 ± 4.13    | 26.56 ± 4.24  | 63.24 ± 4.77  |
| 8      | 0.10 ± 0.10    | 10.12 ± 2.96  | 40.42 ± 16.01 |
| 9      | 52.89 ± 3.90   | 55.52 ± 3.7   | 58.14 ± 8.15  |
| 10     | 55.71 ± 10.20  | 59.73 ± 4.77  | 64.25 ± 6.72  |
| 11     | 2.60 ± 0.50    | 23.12 ± 3.59  | 72.95 ± 7.42  |
| 12     | 11.90 ± 0.64   | 32.90 ± 0.79  | 70.33 ± 9.14  |
| 13     | 100            | 100           | 100           |

The most active peptide is SEQ ID 4 ('KM'), in which the first amino acid E is substituted by A. SEQ ID 8, in which C was substituted by A, also shows good activity relative to both the SP0 control and to the starting KM0 decapeptide. The CFU reduction for these two decapeptides compared to the control was statistically significant at all three doses (p<0.005 by two-tailed Student's t test).

On the basis of KM0 and KM sequences, scramble peptides (SP0, SEQ ID 13; SP, SEQ ID 29) were also synthesised. Neither of these two scramble peptides showed in vitro candidacidal activity.

Alanine-scanning of KM2 is shown in SEQ IDs 40 to 47.
Alanine-scanning of KM5 is shown in SEQ IDs 49 to 57.

C-terminal Truncation of KM

SEQ ID 4 ('KM') was reduced by C-terminal deletions down to three residues to establish the ability to retain in vitro candidacidal activity relative to the SP control. Scalar dilutions (100-0.8 µg/ml) were tested to establish the minimal fungicidal concentration corresponding to the killing of 100% of C. albicans cells. KM and its truncation derivatives were also tested at scalar dilutions to establish the peptide concentration (mol/l) corresponding to the 50% inhibitory concentration (IC50). Assays were performed in triplicate and the IC50 of each peptide was calculated by nonlinear regression analysis of curves obtained by plotting the number of CFU versus Log peptide concentration using the GraphPad Prism 3.02 software. Results were as follows:

| SEQ ID | IC50 (mol/l) |
|---|---|
| 4 | $5.6 \times 10^{-8}$ |
| 14 | $5 \times 10^{-5}$ |
| 15 | $2.3 \times 10^{-5}$ |
| 16 | $6 \times 10^{-7}$ |
| 17 | $7.3 \times 10^{-4}$ |
| 18 | $2.5 \times 10^{-5}$ |
| 19 | $7.1 \times 10^{-4}$ |
| 20 | $1 \times 10^{-5}$ |

There is a drop of candidacidal activity of about three orders of magnitude with deletion of the C-terminus serine from KM. However, the heptamer formed by deletion of the 3 C-terminal residues shows activity only one order of magnitude lower than that of KM.

KM Oligomers

Experiments on the stability of the killer peptide KM after lyophilisation were carried out using the CFU assay. KM proved to be very stable in the lyophilised form.

After solubilisation in non-reducing conditions, the free cysteine in KM can lead to the formation of a disulfide bridge, to give a KM dimer. The candidacidal activity of the dimer was assessed by comparison to dimerised SP peptide. The disulfide-bonded KM dimer retains candidacidal activity. Moreover, this activity was maintained unaltered over a long period under different storage conditions (4° C. room temperature, 37° C.).

In Vivo Activity of KM in Vaginal Infection Model

KM was tested using a well-established experimental model [71] of vaginal C. albicans infection in oophorectomized estrogen-treated rats. Estrogen-conditioned rats (5 animals per group) were inoculated intravaginally with $10^7$ cells of fluconazole-sensitive (SA-40) or fluconazole-resistant (AIDS 68) C.albicans.Both Candida strains were originally isolated from human vaginal infection, and maintained in stock in the Department of Bacteriology and Medical Mycology of the Instituto Superiore di Sanità (ISS), Rome (Italy). Different doses (10, 25, 50 and 100 µg) of KM were administered intravaginally at 1, 24 and 48 hours post challenge and vaginal C.albicans burden was quantitated by CFU enumeration from the vaginal fluid taken each day by a special calibrated loop. Vaginal smears were also stained by PAS-van Gieson method. Any benefit of KM treatment was assessed in terms of microscopic reduction of the hyphal growth in the vagina. Negative controls were untreated rats and rats treated with SP. As a positive control, rats received 50 or 100 µg/ml fluconazole (Pfizer) in PBS (0.1 ml ) at 1, 24 and 48 hours after the yeast challenge.

A dose-response therapeutic effect was observed at 50 and 100 µg doses.

In subsequent experiments, 50 µg of KM was used in the established three dose administration schedule to determine acceleration of fungal CFU clearance over a period of 28 days. Rats (five per groups) were given $10^7$ cells in 0.1 ml of physiological solution on day 0 and were sampled for initial intravaginal CFU. Treatments were administered 1, 24 and 48 hours after the challenge.

Figure 8:
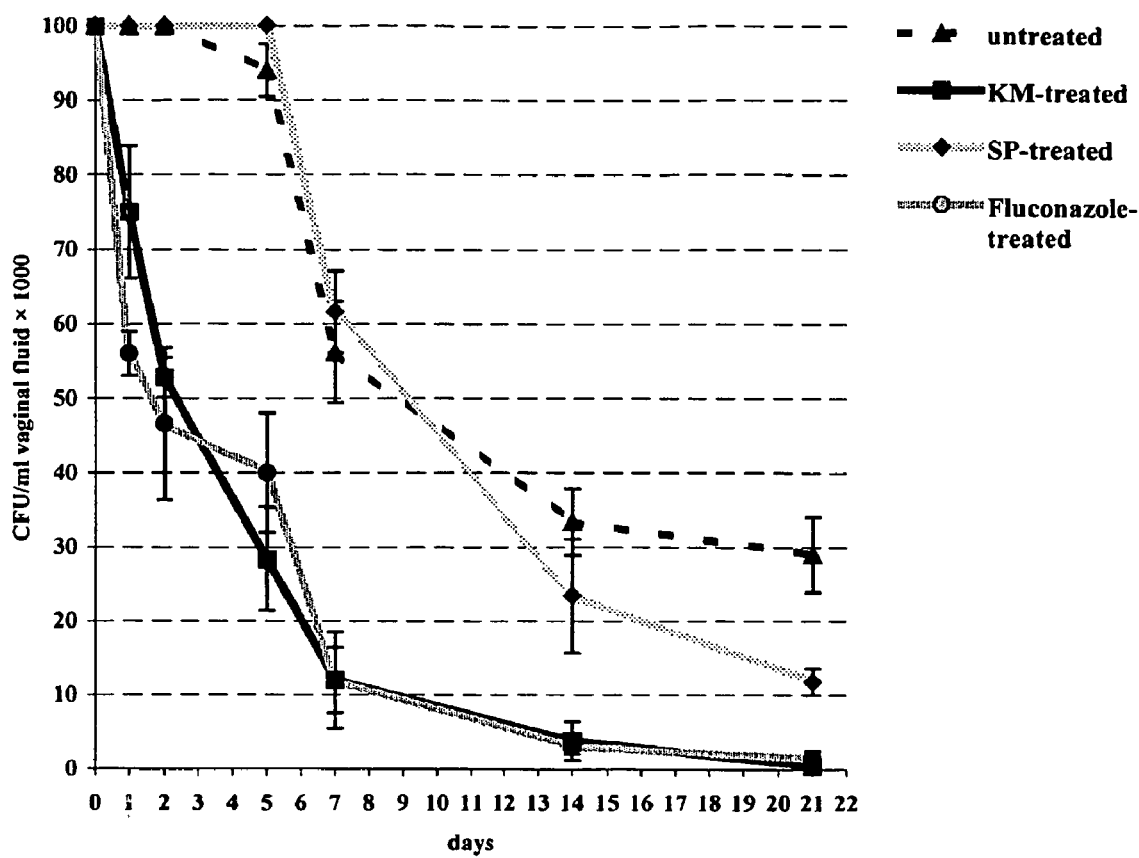
FIG. 8 shows clearance of vaginal candidiasis in rats intravaginally administered with KM.

FIG. 8 shows the results of a typical experiment with strain SA-40.At each time point there was a statistically-significant difference (p<0.05 by two-tailed Student's t test) in vaginal CFU counts between (a) untreated or SP-treated rats, and (b) KM-treated or fluconazole-treated rats. There was no significant difference between untreated and SP-treated rats, and there was no significant difference between KM-treated and fluconazole-treated rats.

KM significantly accelerates the early rate of clearance (1-5 days) of the fungus from rat vagina, also providing a substantial resolution of the infection (less than $10^3$ CFU/ml of vaginal fluid) within three weeks from challenge, when the untreated controls still had from 2 to $4 \times 10^4$ Candida CFU/ml of vaginal fluid. No acceleration of the fungal clearance and no effect on resolution of infection was provided by SP administration. The therapeutic benefit of KM was substantially comparable with that of fluconazole.

Results for both test strains over 28 days were as follows:

| | C. albicans vaginal CFU ($\times 10^3$) (±SD) on days: | | | |
|---|---|---|---|---|
| Experimental group | 0 | 7 | 14 | 28 |
| 1. C. albicans SA-40, no treatment | >100 | 98 ± 12 | 42 ± 7 | 38 ± 6 |
| 2. C. albicans SA-40 + 50 µg fluconazole | >100 | 13 ± 4 | 2 ± 1 | <1 |
| 3. C. albicans SA-40 + KM | >100 | 12 ± 7 | 1 ± 1 | <1 |
| 4. C. albicans AIDS 68, no treatment | >100 | 70 ± 10 | 55 ± 8 | 18 ± 3 |
| 5. C. albicans AIDS 68 + 100 µg fluconazole | >100 | 64 ± 6 | 48 ± 3 | 12 ± 4 |
| 6. C. albicans AIDS 68 + KM | >100 | 40 ± 5 | 18 ± 2 | <1 |

On day 7, 14 and 28, differences in CFU vaginal counts were statistically significant (p<0.05, two-tailed Student's t test) between:
group 1 and group 2
group 1 and group 3
group 4 and group 6
group 1 and group 5
group 1 and group 6
group 5 and group 6

There was no statistically significant difference between:
group 2 and group 3
group 4 and group 5

In contrast to treatment with 100 µg fluconazole, KM had a therapeutic effect also in rat vaginal infection caused by the fluconazole-resistant C.albicans strain.

In Vivo Anti-Candida Activity of KM in Systemic Infection Model

KM was tested using a well-established rapidly-lethal systemic mouse model [72] of C. albicans infection. Groups of 8 Balb/C female mice (weight 18-21 g) were challenged with 5 $LD_{50}$ ($10^7$ cells of SA-40) by the intravenous route. 50 µg KM were administered intraperitoneally for three days starting on day 0 (i.e. 1 hour after the fungal challenge) and at 24 and 48 hours thereafter. Controls were untreated animals or animals treated with peptide SP (same dosage and treatment schedule as those treated with KM). The animals were then followed for mortality and internal organ invasion for 60 days. Any beneficial effect was established in term of prolongation of the median survival time (in days) and reduction of total mortality. Assessment by necroscopy showed that the death of the animals was due to the fungus, and assessment of internal organs showed invasion by C.albicans.

In parallel experiments, SCID mice were used instead of immunocompetent mice in order to verify whether the curative effect of KM required the participation of host adaptive immunity. These experiments used the same challenging fungal burden, schedule of KM and SP treatments, and C. albicans-caused mortality end-points as described above.

Figure 9:
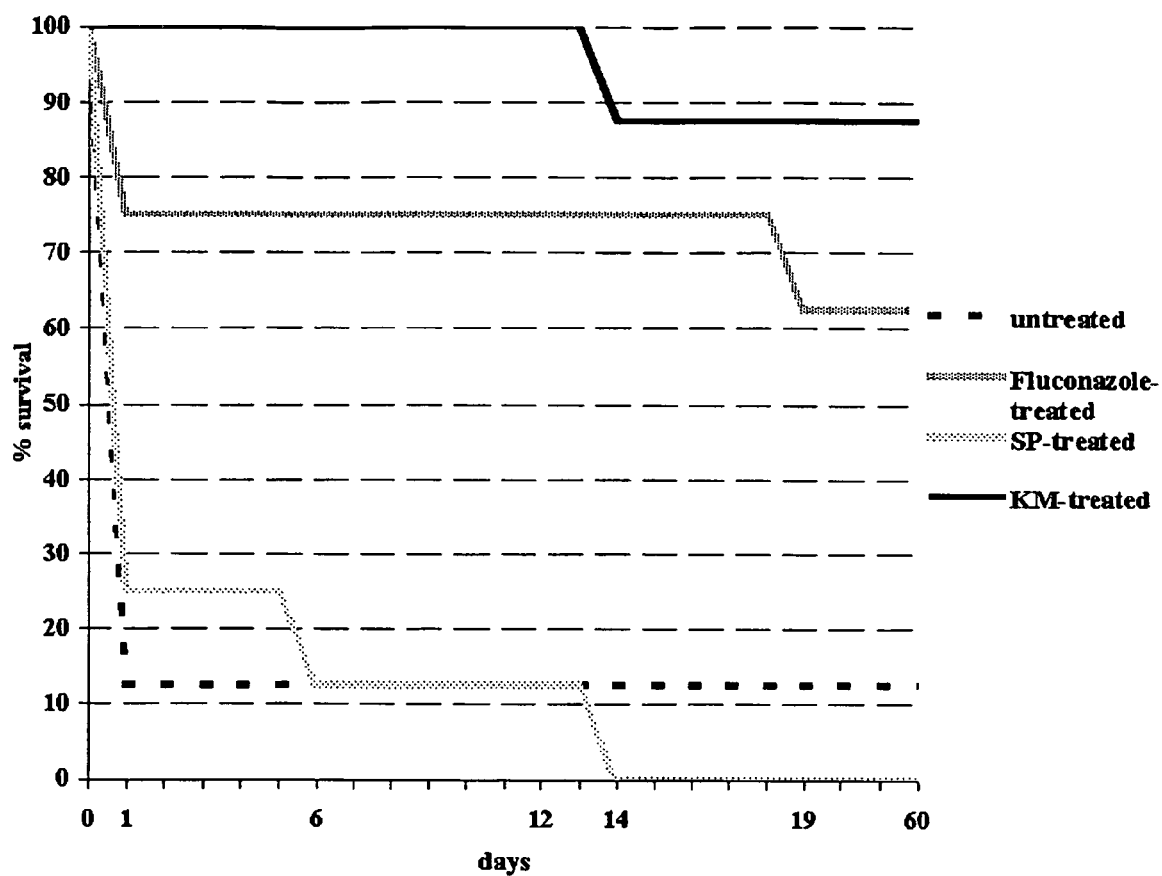
FIG. 9 shows a Kaplan-Meyer survival curve of SCID mice challenged with 5 LD50 of C. albicans and treated with KM.

In all experiments, KM exerted a similar beneficial therapeutic effect in terms of mortality delay and animal cure (60 days). As a typical example, FIG. 9 shows the Kaplan-Meyer survival curve of SCID mice challenged with 5×LD50 of C.albicans and treated with 50 µg of either KM, fluconazole or SP, or left untreated. KM was seen to increase the median survival time from 1 day of the untreated control to >60 days. In addition, only ⅛ KM-treated animals died as compared to ⅝ deaths in untreated mice or those treated with SP. In all cases, death was attributable to C.albicans challenge as shown by fungus burden in the kidneys. FIG. 9 shows that KM out-performed fluconazole.

Blocking of KM Activity by Glucans

As shown above, KM shows anti-candida activity. As KM is distantly-related to the KT antibody, which interacts with cell surface β-glucans, the possible involvement of glucans in KM's activity was investigated.

The binding of the KT mAb to germinating cells of C.albicans was assessed by immunofluorescence [12]. KM completely inhibited the binding of KT to the cells, whereas SP did not.

In further experiments, the CFU assay was performed as before, using 25µg/ml KM or SP, except that various concentrations (between 12.5µg/ml and 100 µg/ml) of either laminarin (β-1,3-glucan, from Sigma) or pustulan (β-1,6-glucan, from Calbiochem) were included. Results were as follows:

| Glucan | Conc$^n$ (µg/ml) | CFU with KM | CFU with SP |
|---|---|---|---|
| None | — | 0 | 2822.00 ± 122.00 |
| Laminarin | 12.5 | 0 | 2525.33 ± 92.72 |
| Laminarin | 25 | 1.33 ± 0.58 | 2780.00 ± 264.21 |
| Laminarin | 50 | 115.33 ± 12.58 | 2742.66 ± 105.09 |
| Laminarin | 100 | 2766.66 ± 63.54 | 2740.00 ± 282.13 |
| Pustulan | 12.5 | 0 | 2380.00 ± 148.04 |
| Pustulan | 25 | 0 | 2500.00 ± 52.00 |
| Pustulan | 50 | 0 | 2666.00 ± 306.49 |
| Pustulan | 100 | 0 | 2824.00 ± 119.82 |

Thus the candidacidal activity of KM was strongly and dose-dependently inhibited by laminarin, but not by pustulan.

These data suggest that the candidacidal KM decapeptide competes for the binding site of KT-IdAb on fungal cell wall, and the receptor seems to contain β-1-3 glucans.

Anti-A.Castellani Activity

In addition to their anti-candida activity, the KM peptide and the K20 monoclonal antibody were tested for activity against trophozoites (the infectious form) of the eukaryotic free-living soil amoeba Acanthamoeba castellanii —a cause of encephalomyelitis and keratitis which can cause severe ocular inflammation and visual loss.

A.castellani was grown in PYG medium at 37° C. or 25° C., in the presence of either SP or KM peptides at 1 µg/ml, 10 µg/ml or 100 µg/ml (or, as a control, with no peptide). The effect on growth over six days, in terms of the number of trophozoites, is shown in FIG. 14. As seen in FIGS. 14C & 14D, the scramble peptide SP has no antimicrobial activity at either 37° C. or 25° C., whereas KM (FIGS. 14A & 14b) shows good antimicrobial activity.

FIG. 15 shows the in vitro activity of KM at 190 µg/ml on cell viability of A.castellanii evaluated at 25° C. in comparison with SP. FIG. 15A shows a reduction in cell viability ($p<0.05$) after six hours of co-incubation. FIG. 15B shows a similar reduction ($p<0.05$) after six hours co-incubation followed by 18 hours incubation in fresh PYG medium.

Figure 16:
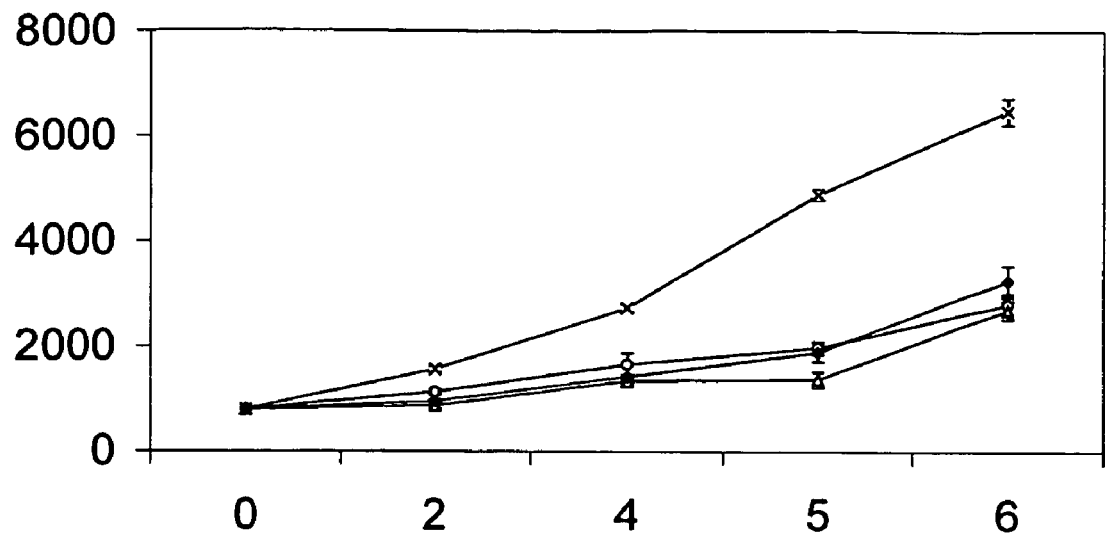
FIG. 16 shows the effect of the K20 mAb on *A.castellani* growth.
Figure 17:
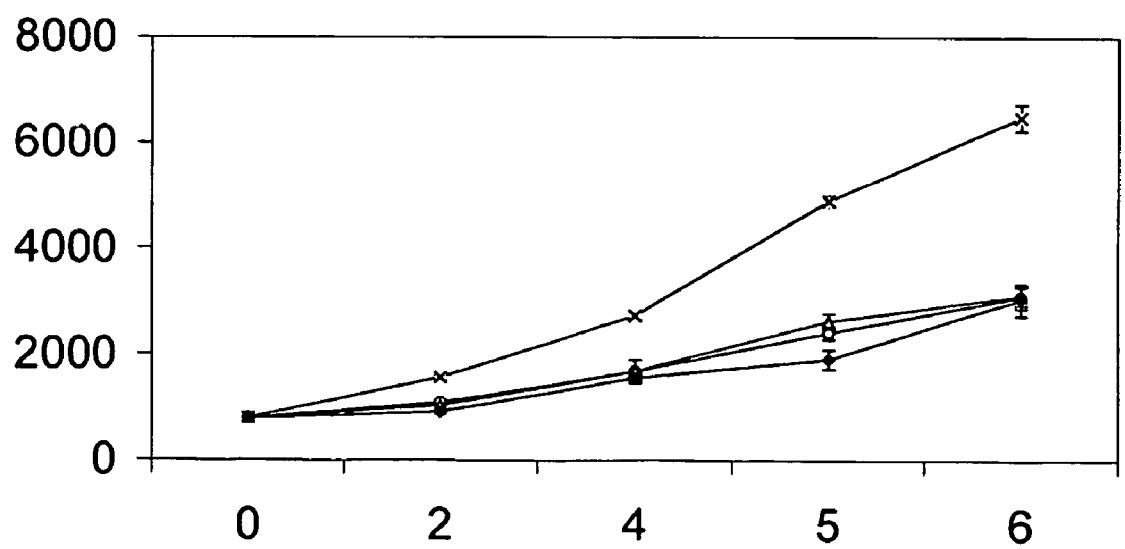
FIG. 17 shows the effect of K10 mAb. Values are the number of trophozoites per well. Amoebal growth in medium alone is shown as crosses. Antibodies were used at 12.5 µg/ml (♦), 25µg/ml (Δ) or 50 µg/ml (○).

The inhibitory effect of monoclonal antiidiotypic antibody K20, tested over 6 days at 370° C. in the same way as described for KM, is shown in FIG. 16. The effect can be compared to that of the rat monoclonal K10 (FIG. 17). After 6 days of incubation, the number of trophozoites per well using K20 was lower than when using K10 at 25 µg (2700 vs. 3100) and 50 µg (2800 vs. 3080).

Range of KM Activity

Figure 10:
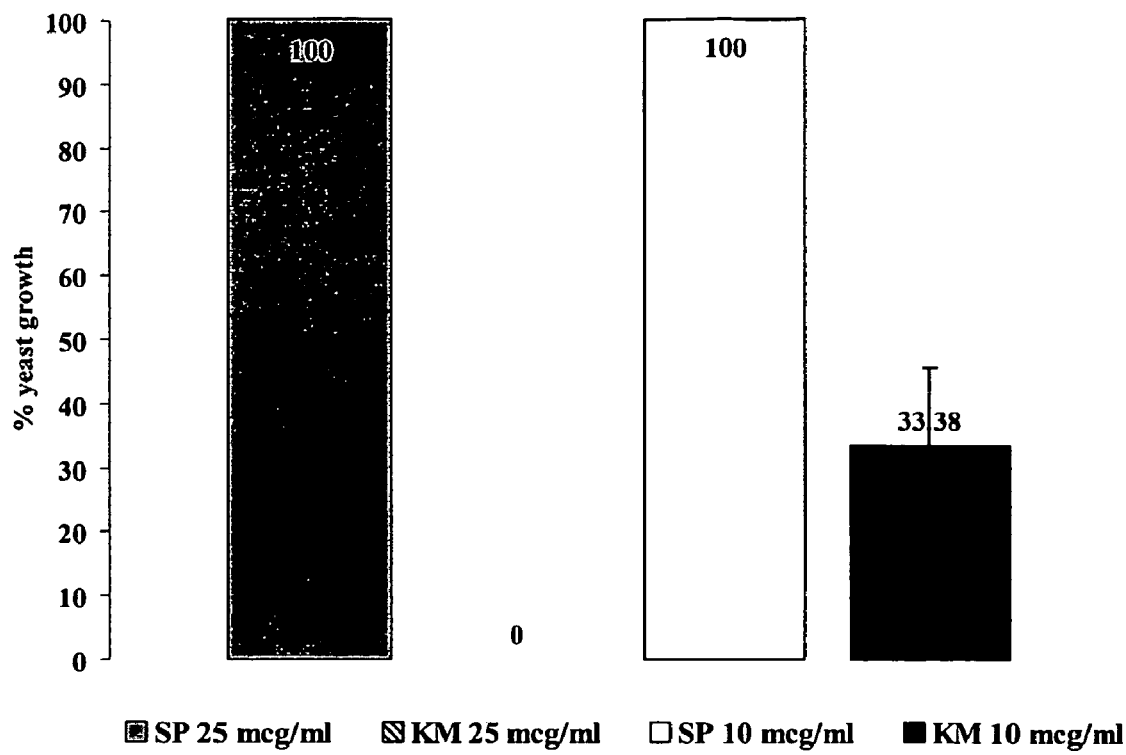
FIG. 10 shows microbicidal activity of KM (25 & 10 μg/ml doses) against C.neoformans UP25.
Figure 11:
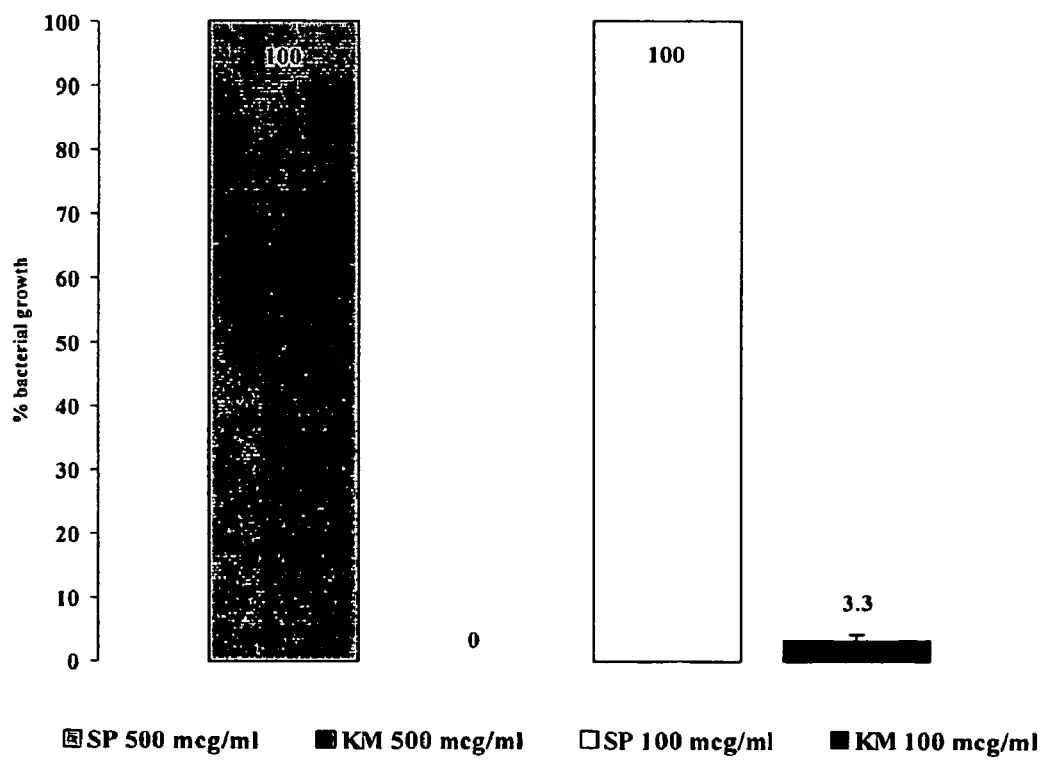
FIG. 11 shows microbicidal activity of KM (500 μg/ml & 100 μg/ml doses) against S.aureus a38.

KM shows potent anti-C.albicans and anti-A.castellani activity. KM was also found to be effective against other microorganisms which are very important from an epidemiological point of view, such as multidrug resistant strains of Candida spp.and Mycobacterium tuberculosis, Cryptococcus neoformans (FIG. 10) and Aspergillus fumigatus, but also against methicillin-resistant strains of Staphylococcus aureus (FIG. 11), and penicillin-resistant strains of Streptococcus pneumoniae.

Surprisingly, KM was also found to have anti-viral activity against influenza A virus and HIV-1.

Influenza A Virus

The effect of KM on influenza virus replication was compared to the scramble peptide SP control. As a further control, replication in maintenance medium alone was tested.

Two different strains of type A influenza virus (Ulster/73/H7N1, avian; NWS/33/H1N1, human neurovirulent) have been previously demonstrated to efficiently replicate in LLC-MK2 (Rhesus monkey kidney), MDCK (Madin Darby Canine Kidney) and AGMK-37RC (African Green Monkey Kidney) cell cultures. Confluent monolayers of the different cell lines were infected with the virus (moi=20 pfu, higher than a normal in vivo infection) in pre-warmed PBS (pH 7.4). After a 40 minute adsorption period, maintenance medium (MM) containing either KM or SP was added to the cell cultures and virus titre was determined after 24, 36, 48 or 72 hours of infection by haemagglutinin (HA) titration in triplicate samples on cell supernatant, after centrifugation at 2,000×g to remove cellular debris.

Figure 18:
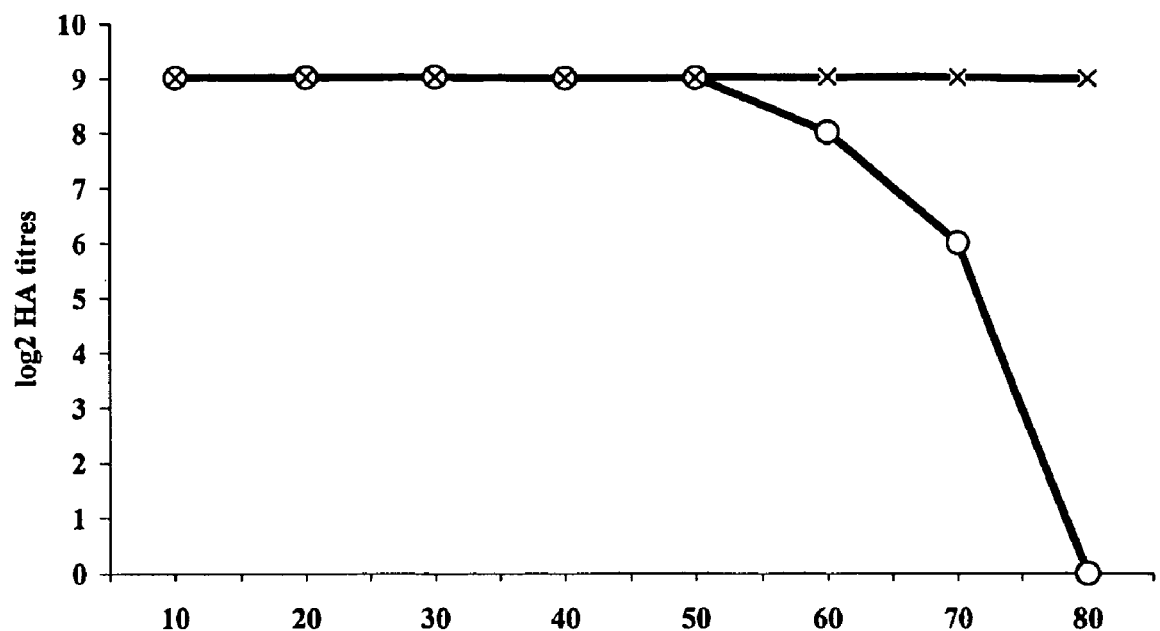
FIG. 18 shows the effect of KM (circles) and SP (crosses) peptides on influenza virus replication at up to 80 µg/ml concentration. Values are $\log_2$ HA titres.

The effect of KM and SP on HA titres 24 hours after infection of LLC-MK2 cells by Ulster/73 is shown in FIG. 18. At 50µg/ml or below, KM and SP had little or no effect on viral growth. Above 60µg/ml, however, KM peptide interferes with viral growth, with complete blocking at 80 µg/ml. Similar effects were seen for the other virus, with the other cell lines, and at the other time points. Thus KM can suppress viral replication in a dose-dependent manner.

In a different set of experiments, fresh MM containing either KM or SP was added to the cells at time 0 and then substituted with the same peptide/medium mixture every 12 hours starting at 24 hours and ending at 72 hours. KM at 80 µg/ml was able to completely block viral production at all time points tested. Using SP, viral titres were similar to those obtained by growth in MM only.

The effect of KM on influenza virus replication was also tested using haemadsorption assays. HA is synthesised during replication and inserted into the cell membrane before viral budding. Haemadsorption of red blood cells to infected cells correlates with the integrity of the glycosylated HA as well as with its correct insertion into the cell membrane.

Cell cultures were infected, treated with 80 µg/ml of either KM or SP, as described above, and haemadsorption assays were carried out after 48 hours. A significant reduction of $OD_{420nm}$ was observed in infected cells treated with KM, demonstrating a significant reduction of viral HA molecules on the plasma membrane of those cells. Neither KM nor SP interferes with virus-specific receptors on red blood cells (RBC).

Finally, the effect of laminarin (β-1,3-glucan) on anti-influenza activity was determined. As shown above, Laminarin interferes with KM's candidacidal activity. KM or SP (80 µg/ml) was mixed with laminarin (320 µg/ml) and the mixture was added to infected cells at time 0, without preincubation or after 10 minutes of preincubation. Similar HA titres were obtained after 24 hours using KM/laminarin and SP/laminarin, suggesting that laminarin abolishes the antiviral activity of KM. This effect was not seen with pustulan.

HIV-1

The effect of KM on HIV-1 replication was compared to the scramble peptide SP control. HIV-1 can replicate in peripheral blood mononuclear cell (PBMC) cultures in the presence of exogenous IL-2 [73]. To test KM activity, PBMC cultures were obtained from patients in acute infection phase in whom HIV-1 proviral load was known.

PBMCs were cultured in 48-well plates at the concentration of $10^6$ cells/ml in RPMI 1640 medium supplemented with 10% FCS in the presence of 50 U/ml of rIL-2. Half of the culture medium was added at day 8. Supernatants and cells were harvested for analysis of HIV RNA and proviral contents, respectively. Exogenous rIL-2 was added every 3 to 4 days, KM- or SP-peptide was added every 7 days. HIV-1 expression was determined using HIV RNA branched kit (b-DNA, Bayer™), whereas HIV-1 proviral load was determined using gene-detective HIV-1 gag EOA kit (ZeptoMetrix™). For phenotype determination, cells were analysed by flow cytometry after staining with mAbs directed to CD antigens.

After PBMC isolation, the majority of PBMC of HIV cultures were T-lymphocytes, as shown by the expression of CD3 Ag (CD4+=41%; CD8+=36%). All primary PBMC cultures remained viable apparently for at least 20 days. In the presence of exogenous IL-2, all CD3+T-cells expressed CD25 and HLA-DR cell surface activation markers after 7 days of culture.

Primary cultures were established from the patient's cryopreserved PBMC in the presence of 1× and 10× concentration of KM peptide (1 µg and 10 µg, respectively). As controls, SP peptide was used at the same concentrations. Other control cultures (untreated cells) received medium only.

Figure 19:
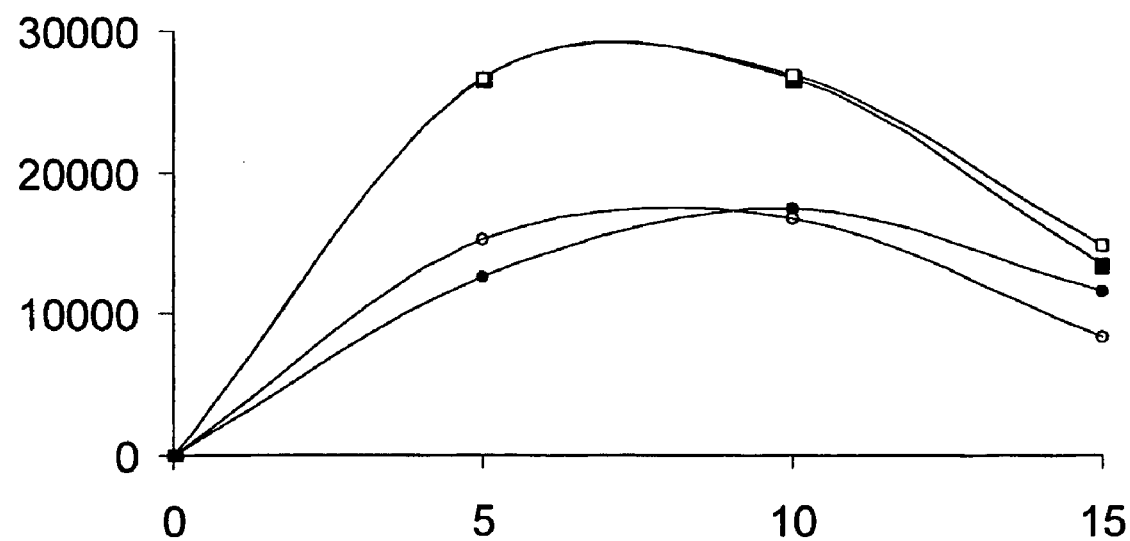
FIG. 19 shows the effect of KM (circles) and SP (squares) peptides on HIV-1 replication. Peptides were used at either 1 µg/ml (closed) or 10 µg/ml (open). Values are copies/ml over 15 days of culture.

The kinetics of HIV RNA production at different time points of PBMC cultures are shown in FIG. 19. The cultures showed early peaks of viral copies within 5 to 10 days of culture which then decreased in correspondence to the HIV-1-induced loss of CD4+ cells. HIV replication in these PBMC cultures was considerably lower in the presence of KM (<44%, mean), with both concentrations of KM having similar effects on the levels and kinetics of HIV RNA production.

SP-treated cells showed the same levels and kinetics of HIV RNA production as untreated controls.

D-amino Acid Derivatives of KM and KM0

KM0 and KM were synthesised using the same amino acids residues, but in the D- rather than L-conformation (KM6 and KM7). Scramble peptide controls SP0 and SP were also synthesised using D-amino acids.

Figure 12:
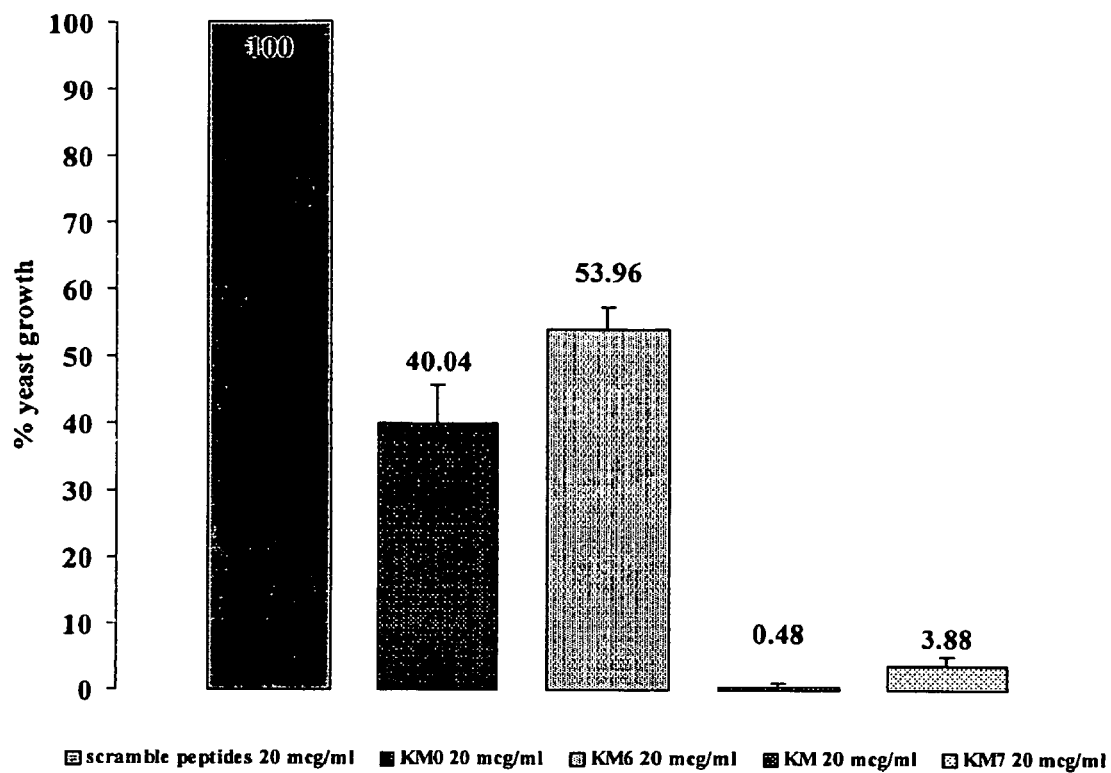
FIG. 12 shows in vitro microbicidal activity of KM0, KM6, KM and KM7 at 20 μg/ml dose.
Figure 13:
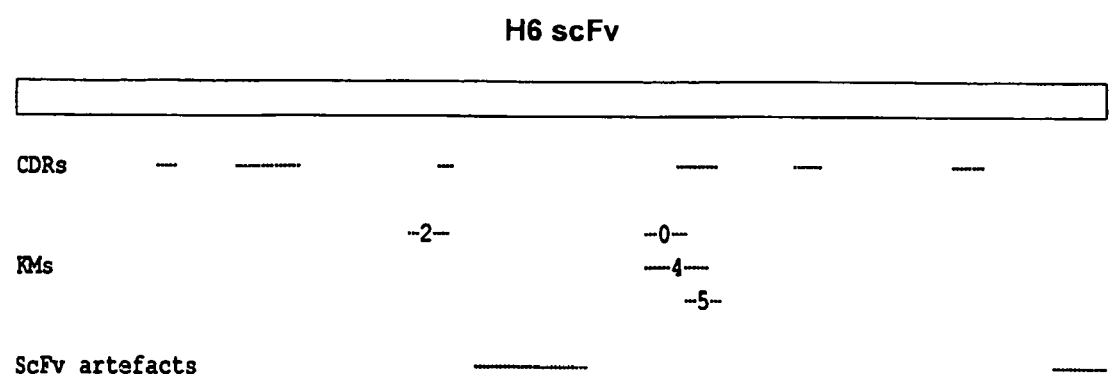
FIG. 13 is an illustration of features within the H6 scFv (SEQ ID 2).

KM6 and KM7 each showed candidacidal activity in the CFU assay (FIG. 12). Activity was slightly lower than the L-amino acid polypeptides, but this in vitro reduction does not take into account the in vivo increase in half life which would be expected.

A D-amino acid polypeptide with both the Glu→Ala and Cys→Ser substitutions (SEQ ID 33) is useful.

Toxicity

Toxicity of KM was assessed by in vitro incubation with LLC-MK2 rhesus monkey kidney cells. The cells were maintained in Eagle's Minimum essential Medium (MEM) supplemented with 10% fetal bovine serum, 100 U/ml penicillin and 100 µg/ml streptomycin at 37° C. in a humidified atmosphere containing 5% $CO_2$. The cells were plated in triplicate in 6-well dishes at $4\times10^4$ cells per well and cultured for 24 hours. Serial dilutions of peptides (final concentrations between 0 and 500 µg/ml) in medium containing 10% fetal bovine serum were then added to cells and incubated for 24 hours at 37° C. Cells were subsequently treated with MTT (50 µg per well) and incubated for another 2 hours. After solubilisation of the formazan dye in DMSO, the absorbance of each well was measured at 550 and 620 nm. Peptide SP was also tested.

Cell viability as T/C % where T represents the mean absorbance of the treated cells of the controls (FIG. 20).

The peptide displayed no toxic effects, even at 500 µg/ml.

Equivalent Peptides From Within H20

An alignment of H6 and H20 sequences is given below, with CDRs in bold:

```
         10        20        30        40        50        60        70
         |         |         |         |         |         |         |
H6   MAQVKLQESGPGLVAPSQSLSITCTVSGFSLTGYGVNWVRQPPGKGLEWLGMIWGD-GSTDYNSALKSRL
     ****:**:**.  **  .. *:.:;**.***.:...* ::**:* * :****:* *   : *.*:*  .::.:
H20  MAQVQLQQSGAKLVRSGASVKLSCTTSGFNIKDYYMHWVKQRPEQGLEWIGWIDPENGDTEYAPKFQGKT 80        90        100       110       120       130       140
         |         |         |         |         |         |         |
```

```
                                              -continued
H6   SISKDNSKSQVFLKMNSLQTDDTARYYC------------LYAMDYWGQGTTVTCSSGGGGSGGGGSGG
     : :: *.*..  .:*::.**  :.*** ***            ***************************
H20  TLTADTSSNTAYLQLSSLTSEDTAVYYCNAWVYDGYSGDFYYYAMDYWGQGTTVTCSSGGGGSGGGGSGG 150       160       170       180       190       200       210
             |         |         |         |         |         |         |
H6   GGSDIELTQSPALMSASPGEKVTMTCSASSSVSYMYWYQQKPRSSPKPWIYLTSNLASGVPARFSGSGSG
     ************: :*********.************.*.****  .*** *** *****************
H20  GGSDIELTQSPAIVSASPGEKVTITCSASSSVSYMHWFQQKPGTSPKLWIYSTSNLASGVPARFSGSGSG 220       230       240       250       260
             |         |         |         |         |
H6   TSYSLTISSMEAEDAATYYCQQWSSNPYTFGGGTKLEIKRAAAGAPVPYPDPLEPR
     ******** ************* **  * *** ***********************
H20  TSYSLTISRMEAEDAATYYCQQRSSYPLTFGAGTKLEIKRAAAGAPVPYPDPLEPR
```

H20 peptide sequences corresponding to H6 peptides KM, KM0, KM1, KM2, KM4 and KM5 are:

| H6        | KM0 | KM1 | KM2 | KM4 | KM5 | KM |
|-----------|-----|-----|-----|-----|-----|----|
| H6 SEQ ID | 3   | 23  | 24  | 26  | 27  | 4  |
| H20 SEQ ID| 34  | 35  | 36  | 37  | 38  | 39 |

It will be understood that the invention has been described by way of example only and modifications may be made whilst remaining within the scope and spirit of the invention.

REFERENCES (the contents of which are hereby incorporated in full)

[1] Magliani et al. Clin. Microbiol. Rev., 10:369-400, 1997
[2] Polonelli et al. J. Clin. Microbiol., 24:866-869, 1986
[3] Aliouat et al. Serodiagn. Immunother. Infect. Dis., 5:102-106, 1993
[4] Conti et al. J. Infect. Dis., 177:807-811, 1998
[5] Polonelli & Morace J. Clin. Microbiol., 25:460-462, 1987
[6] Polonelli & Morace J. Clin. Microbiol., 26, 602-604, 1988
[7] Polonelli et al. Scan. J. Immunol., 37:105-110, 1993
[8] Polonelli et al. J. Immunol., 152:3175-3182, 1994
[9] Séguy et al., FEMS Immunol. Med. Microbiol., 22:145-149, 1998
[10] Polonelli et al., J. Immunol. 156:1880-1885, 1996
[11] Séguy et al. Mol. Med., 3:544-552, 1997
[12] Polonelli et al., Clin. Diagn. Lab. Immunol., 4:142-146, 1997
[13] Magliani et al., Nature Biotechnol., 15:155-158, 1997
[14] Cenci et al. Infect Immun 2002 May; 70(5):2375-2382
[15] Conti et al., Mol. Med., 6/7:613-619, 2000
[16] Séguy et al., J.Euk. Microbiol., 44:37S, 1997
[17] Breedveld (2000) Lancet 355(9205):735-740.
[18] Gorman & Clark (1990) Semin. Immunol. 2:457-466
[19] Jones et al. Nature 321:522-525 (1986)
[20] Morrison et al., Proc. Natl. Acad. Sci, U.S.A., 81:6851-6855 (1984)
[21] Morrison & Oi, Adv. Immunol., 44:65-92 (1988)
[22] Verhoeyer et al., Science 239:1534-1536 (1988)
[23] Padlan, Molec. Immun. 28:489-498 (1991)
[24] Padlan, Molec. Immunol. 31(3):169-217 (1994).
[25] Kettleborough et al., Protein Eng. 4(7):773-83 (1991).
[26] WO 98/24893
[27] WO 91/10741
[28] WO 96/30498
[29] WO 94/02602
[30] U.S. Pat. No. 5,939,598.
[31] Goletz et al. J Mol Biol 2002 Feb 1;315(5): 1087-97
[32] Morrison & Weiss (2001) Curr. Opin. Chem. Biol. 5:302-207.
[33] Weiss et al. (2000) PNAS USA 97:8950-8954.
[34] Carter (1994) Methods Mol Biol 36:207-223.
[35] Li & Roller (2002) Curr Top Med Chem 2:325-341.
[36] Bodanszky (1993) Principles of Peptide Synthesis (ISBN: 0387564314).
[37] Fields et al. (1997) Methods in Enzymology 289:Solid-Phase Peptide Synthesis. ISBN: 0121821900
[38] Chan & White (2000) Fmoc Solid Phase Peptide Synthesis ISBN: 0199637245.
[39] Kullmann (1987) Enzymatic Peptide Synthesis. ISBN: 0849368413.
[40] Ibba (1996) Biotechnol Genet Eng Rev 13:197-216.
[41] Strugnell et al. (1997) Immunol Cell Biol 75(4):364-369.
[42] Robinson & Torres (1997) Seminars in Immunol 9:271-283.
[43] Donnelly et al. (1997) Annu Rev Immunol 15:617-648.
[44] Brunham et al. (2000) J Infect Dis 181 Suppl 3:S538-43.
[45] Svanholm et al. (2000) Scand J Immunol 51(4):345-53.
[46] Beninati et al. (2000) Nature Biotechnology 18:1060-1064.
[47] Bevan & Makower (1963) pages 202-203 of Geerts (ed.), Genetics today, XIth International Congress on Genetics vol. 1.Pergamon Press, Oxford, England.
[48] Kazmierski (1999) Peptidomimetics Protocols. ISBN: 0896035174.
[49] Abell (1999) Advances in Amino Acid Mimetics and Peptidomimetics.ISBN: 0762306149.
[50] U.S. Pat. No. 5,331,573 (Balaji).
[51] Goodman et al. (2001) Biopolymers 60:229-245.
[52] Hruby & Balse (2000) Curr Med Chem 7:945-970.
[53] Ribka & Rich (1998) Curr Opin Chem Biol 2:441-452.
[54] Chakraborty et al. (2002) Curr Med Chem 9:421-435.
[55] Computer-Assisted Lead Finding and Optimization (eds. Testra & Folkers, 1997).
[56] Available from Molecular Simulations Inc (http://www.msi.com/).
[57] Davic & Lawrence (1992) Proteins 12:31-41.
[58] Caflish et al. (1993) J Med. Chem. 36:2142-67
[59] Eisen et al. (1994) Proteins: Str. Funct. Genet. 19:199-221.
[60] Böhm (1992) J Comp. Aided Molec. Design 6:61-78.
[61] Gehlhaar et al. (1995) J Med. Chem. 38:466-72.
[62] Moon & Howe (1991) Proteins: Str. Funct. Genet. 11:314-328.
[63] Available from http://chem.leeds.ac.uk/ICAMS/SPROUT.html.
[64] Lauri & Bartlett (1994) Comp. Aided Mol. Design 8:51-66.
[65] Available from Tripos Inc (http://www.tripos.com).

[66] Rotstein et al. (1993) *J. Med Chem.* 36:1700.
[67] Lai (1996) *J Chem. Inf. Comput. Sci.* 36:1187-1194.
[68] Gennaro (2000) *Remington: The Science and Practice of Pharmacy.* 20th ed., ISBN: 0683306472
[69] Almeida & Alpar (1996) J Drug Targeting 3:455-467.
[70] Wills et al. (2000) Emerging Therapeutic Targets 4:1-32.
[71] De Bernardis et al., in *Handbook of animal models of infection* (eds. Zak, O. & Sande, M.A.) 735-740, Academic Press, New York, 1999
[72] Mencacci et al., Infect. Immun., 62:5353-5360, 1994
[73] Casoli et al. (2000) *Blood* 95: 2760-2769.

---

The invention claimed is:

1. An isolated polypeptide consisting of amino acid sequence SEQ ID NO. 3, 4, 5, 6, 7, 8, 9, 10, 11 or 12, with constituent amino acids in the D- and/or L-configuration.

2. An isolated polypeptide consisting of amino acid sequence SEQ ID NO. 14, 15, 16, 17, 18, 19, 20, 23, 24 or 25, with constituent amino acids in the D- and/or L-configuration.

3. The polypeptide of claim 1, wherein the polypeptide has miczrobicidal activity.

4. The polypeptide of claim 2, wherein the polypeptide has microbicidal activity.

5. A pharmaceutical composition comprising (a) the polypeptide of claim 3 and (b) a pharmaceutical carrier.

6. A pharmaceutical composition comprising (a) the polypeptide of claim 4 and (b) a pharmaceutical carrier.

* * * * *

UNITED STATES PATENT AND TRADEMARK OFFICE
CERTIFICATE OF CORRECTION

PATENT NO. : 7,722,876 B2
APPLICATION NO. : 10/514781
DATED : May 25, 2010
INVENTOR(S) : Polonelli et al.

It is certified that error appears in the above-identified patent and that said Letters Patent is hereby corrected as shown below:

In page 1, column 1, section (73) Assignee, "Istituto Superiore di Sanita, Rome (IT)" should be- Istituto Superiore di Sanita, Rome (IT), Luciano Polonelli, Parma (IT), Universita' degli Studi di Siena, Siena (IT).

Signed and Sealed this
First Day of May, 2012

David J. Kappos
*Director of the United States Patent and Trademark Office*

SEQUENCE LISTING

<160> NUMBER OF SEQ ID NOS: 71

<210> SEQ ID NO 1
<211> LENGTH: 756
<212> TYPE: DNA
<213> ORGANISM: Artificial Sequence
<220> FEATURE:
<223> OTHER INFORMATION: recombinant phage single chain Fv H6 antibody nucleotide sequence

<400> SEQUENCE: 1

```
atggcccagg tgaagctgca ggagtctgga cctggcctgg tggcgccctc acagagcctg      60
tccatcacat gcaccgtctc agggttctca ttaaccggct atggtgtaaa ctgggttcgc     120
cagcctccag gaaagggtct ggagtggctg gaatgatat ggggtgatgg aagcacagac     180
tataattcag ctctcaaatc cagactgagc atcagcaagg acaactccaa gagccaagtt     240
ttcttaaaaa tgaacagtct gcaaactgat gacacagcca ggtactactg tctctatgct     300
atggactact ggggccaagg gaccacggtc accttctcct caggtggagg cggttcaggc     360
ggaggtggct ctggcggtgg cggatcggac atcgagctca ctcagtctcc agcactcatg     420
tctgcatctc caggggagaa ggtcaccatg acctgcagtg ccagctcaag tgtaagttac     480
atgtactggt accagcagaa gccaagatcc tcccccaaac cctggattta tctcacatcc     540
aacctggctt ctggagtccc tgctcgcttc agtggcagtg gtctgggac ctcttactct     600 ctcacaatca gcagcatgga ggctgaagat gctgccactt attactgcca gcagtggagt     660
agtaacccat acacgttcgg aggggcacc aagctggaaa tcaaacgtgc ggccgcaggt     720
gcgccggtgc cgtatccgga tccgctggaa ccgcgt                              756
```

<210> SEQ ID NO 2
<211> LENGTH: 252
<212> TYPE: PRT
<213> ORGANISM: Artificial Sequence
<220> FEATURE:
<223> OTHER INFORMATION: recombinant phage single chain Fv H6 antibody amino acid sequence

<400> SEQUENCE: 2

```
Met Ala Gln Val Lys Leu Gln Glu Ser Gly Pro Gly Leu Val Ala Pro
1               5                   10                  15

Ser Gln Ser Leu Ser Ile Thr Cys Thr Val Ser Gly Phe Ser Leu Thr
            20                  25                  30

Gly Tyr Gly Val Asn Trp Val Arg Gln Pro Pro Gly Lys Gly Leu Glu
        35                  40                  45

Trp Leu Gly Met Ile Trp Gly Asp Gly Ser Thr Asp Tyr Asn Ser Ala
    50                  55                  60

Leu Lys Ser Arg Leu Ser Ile Ser Lys Asp Asn Ser Lys Ser Gln Val
65                  70                  75                  80

Phe Leu Lys Met Asn Ser Leu Gln Thr Asp Asp Thr Ala Arg Tyr Tyr
            85                  90                  95
```

-continued

```
Cys Leu Tyr Ala Met Asp Tyr Trp Gly Gln Gly Thr Val Thr Cys
            100                 105                 110
Ser Ser Gly Gly Gly Ser Gly Gly Gly Ser Gly Gly Gly Gly
        115                 120                 125
Ser Asp Ile Glu Leu Thr Gln Ser Pro Ala Leu Met Ser Ala Ser Pro
    130                 135                 140
Gly Glu Lys Val Thr Met Thr Cys Ser Ala Ser Ser Val Ser Tyr
145                 150                 155                 160
Met Tyr Trp Tyr Gln Gln Lys Pro Arg Ser Ser Pro Lys Pro Trp Ile
                165                 170                 175
Tyr Leu Thr Ser Asn Leu Ala Ser Gly Val Pro Ala Arg Phe Ser Gly
            180                 185                 190
Ser Gly Ser Gly Thr Ser Tyr Ser Leu Thr Ile Ser Ser Met Glu Ala
        195                 200                 205
Glu Asp Ala Ala Thr Tyr Tyr Cys Gln Gln Trp Ser Ser Asn Pro Tyr
    210                 215                 220
Thr Phe Gly Gly Gly Thr Lys Leu Glu Ile Lys Arg Ala Ala Ala Gly
225                 230                 235                 240
Ala Pro Val Pro Tyr Pro Asp Pro Leu Glu Pro Arg
                245                 250

<210> SEQ ID NO 3
<211> LENGTH: 10
<212> TYPE: PRT
<213> ORGANISM: Artificial Sequence
<220> FEATURE:
<223> OTHER INFORMATION: synthetic H6 KM0, residues 146-155 of scFv H6
      (seq ID 2)

<400> SEQUENCE: 3

Glu Lys Val Thr Met Thr Cys Ser Ala Ser
1               5                   10

<210> SEQ ID NO 4
<211> LENGTH: 10
<212> TYPE: PRT
<213> ORGANISM: Artificial Sequence
<220> FEATURE:
<223> OTHER INFORMATION: synthetic H6 KM, Glu-Ala mutation of H6 KM0
      (seq ID 3)

<400> SEQUENCE: 4

Ala Lys Val Thr Met Thr Cys Ser Ala Ser
1               5                   10

<210> SEQ ID NO 5
<211> LENGTH: 10
<212> TYPE: PRT
<213> ORGANISM: Artificial Sequence
<220> FEATURE:
<223> OTHER INFORMATION: synthetic alanine-scanning variant of H6 KM0
      (seq ID 3)

<400> SEQUENCE: 5

Glu Ala Val Thr Met Thr Cys Ser Ala Ser
1               5                   10

<210> SEQ ID NO 6
<211> LENGTH: 10
<212> TYPE: PRT
<213> ORGANISM: Artificial Sequence
<220> FEATURE:
<223> OTHER INFORMATION: synthetic alanine-scanning variant of H6 KM0
```

-continued (seq ID 3)

<400> SEQUENCE: 6

Glu Lys Ala Thr Met Thr Cys Ser Ala Ser
1 5 10

<210> SEQ ID NO 7
<211> LENGTH: 10
<212> TYPE: PRT
<213> ORGANISM: Artificial Sequence
<220> FEATURE:
<223> OTHER INFORMATION: synthetic alanine-scanning variant of H6 KM0
(seq ID 3)

<400> SEQUENCE: 7

Glu Lys Val Ala Met Thr Cys Ser Ala Ser
1 5 10

<210> SEQ ID NO 8
<211> LENGTH: 10
<212> TYPE: PRT
<213> ORGANISM: Artificial Sequence
<220> FEATURE:
<223> OTHER INFORMATION: synthetic alanine-scanning variant of H6 KM0
(seq ID 3)

<400> SEQUENCE: 8

Glu Lys Val Thr Ala Thr Cys Ser Ala Ser
1 5 10

<210> SEQ ID NO 9
<211> LENGTH: 10
<212> TYPE: PRT
<213> ORGANISM: Artificial Sequence
<220> FEATURE:
<223> OTHER INFORMATION: synthetic alanine-scanning variant of H6 KM0
(seq ID 3)

<400> SEQUENCE: 9

Glu Lys Val Thr Met Ala Cys Ser Ala Ser
1 5 10

<210> SEQ ID NO 10
<211> LENGTH: 10
<212> TYPE: PRT
<213> ORGANISM: Artificial Sequence
<220> FEATURE:
<223> OTHER INFORMATION: synthetic alanine-scanning variant of H6 KM0
(seq ID 3)

<400> SEQUENCE: 10

Glu Lys Val Thr Met Thr Ala Ser Ala Ser
1 5 10

<210> SEQ ID NO 11
<211> LENGTH: 10
<212> TYPE: PRT
<213> ORGANISM: Artificial Sequence
<220> FEATURE:
<223> OTHER INFORMATION: synthetic alanine-scanning variant of H6 KM0
(seq ID 3)

<400> SEQUENCE: 11

Glu Lys Val Thr Met Thr Cys Ala Ala Ser
1 5 10

<210> SEQ ID NO 12

```
<211> LENGTH: 10
<212> TYPE: PRT
<213> ORGANISM: Artificial Sequence
<220> FEATURE:
<223> OTHER INFORMATION: synthetic alanine-scanning variant of H6 KM0
      (seq ID 3)

<400> SEQUENCE: 12

Glu Lys Val Thr Met Thr Cys Ser Ala Ala
1               5                   10

<210> SEQ ID NO 13
<211> LENGTH: 10
<212> TYPE: PRT
<213> ORGANISM: Artificial Sequence
<220> FEATURE:
<223> OTHER INFORMATION: synthetic SP0 scramble control peptide

<400> SEQUENCE: 13

Met Ser Thr Ala Val Ser Lys Cys Glu Thr
1               5                   10

<210> SEQ ID NO 14
<211> LENGTH: 9
<212> TYPE: PRT
<213> ORGANISM: Artificial Sequence
<220> FEATURE:
<223> OTHER INFORMATION: synthetic shortened KM-derived peptide (9 mers
      of seq ID 4)

<400> SEQUENCE: 14

Ala Lys Val Thr Met Thr Cys Ser Ala
1               5

<210> SEQ ID NO 15
<211> LENGTH: 8
<212> TYPE: PRT
<213> ORGANISM: Artificial Sequence
<220> FEATURE:
<223> OTHER INFORMATION: synthetic shortened KM-derived peptide (8 mers
      of seq ID 4)

<400> SEQUENCE: 15

Ala Lys Val Thr Met Thr Cys Ser
1               5

<210> SEQ ID NO 16
<211> LENGTH: 7
<212> TYPE: PRT
<213> ORGANISM: Artificial Sequence
<220> FEATURE:
<223> OTHER INFORMATION: synthetic shortened KM-derived peptide (7 mers
      of seq ID 4)

<400> SEQUENCE: 16

Ala Lys Val Thr Met Thr Cys
1               5

<210> SEQ ID NO 17
<211> LENGTH: 6
<212> TYPE: PRT
<213> ORGANISM: Artificial Sequence
<220> FEATURE:
<223> OTHER INFORMATION: synthetic shortened KM-derived peptide (6 mers
      of seq ID 4)

<400> SEQUENCE: 17

Ala Lys Val Thr Met Thr
```

<210> SEQ ID NO 18
<211> LENGTH: 5
<212> TYPE: PRT
<213> ORGANISM: Artificial Sequence
<220> FEATURE:
<223> OTHER INFORMATION: synthetic shortened KM-derived peptide (5 mers of seq ID 4)

<400> SEQUENCE: 18

Ala Lys Val Thr Met
1               5

<210> SEQ ID NO 19
<211> LENGTH: 4
<212> TYPE: PRT
<213> ORGANISM: Artificial Sequence
<220> FEATURE:
<223> OTHER INFORMATION: synthetic shortened KM-derived peptide (4 mers of seq ID 4)

<400> SEQUENCE: 19

Ala Lys Val Thr
1

<210> SEQ ID NO 20
<211> LENGTH: 3
<212> TYPE: PRT
<213> ORGANISM: Artificial Sequence
<220> FEATURE:
<223> OTHER INFORMATION: synthetic shortened KM-derived peptide (3 mers of seq ID 4)

<400> SEQUENCE: 20

Ala Lys Val
1

<210> SEQ ID NO 21
<211> LENGTH: 798
<212> TYPE: DNA
<213> ORGANISM: Artificial Sequence
<220> FEATURE:
<223> OTHER INFORMATION: recombinant phage single chain Fv H20 antibody nucleotide sequence

<400> SEQUENCE: 21

```
atggcccagg tgcagctgca gcagtctggg gcaaagcttg tgaggtcagg ggcctcagtc      60
aagttgtcct gcacaacttc tggcttcaac attaaagact actatatgca ctgggtgaag     120
caaaggcctg aacagggcct ggagtggatt ggatggattg atcctgagaa tggtgatact     180
gaatatgccc cgaagttcca gggcaagacc actctgactg cagacacatc ctccaacaca     240
gcctacctgc agctcagcag cctgacatct gaggacactg ccgtctatta ctgtaatgca     300
tgggtctatg atggttactc gggtgatttt tattactatg ctatggacta ctggggccaa     360
gggaccacgg tcaccttctc ctcaggtgga ggcggttcag gcggaggtgg ctctggcggt     420
ggcggatcgg acatcgagct cactcagtct ccagcaatcg tgtctgcatc tccaggggag     480
aaggtcacca taacctgcag tgccagctca agtgtaagtt acatgcactg gttccagcag     540
aagccaggca cttctcccaa actctggatt tatagcacat ccaacctggc ttctggagtc     600
cctgctcgct tcagtggcag tggatctggg acctcttact ctctcacaat cagccgaatg     660
gaggctgaag atgctgccac ttattactgc cagcaaagga gtagtaccc gctcacgttc     720
```
ggtgctggca ccaagctgga atcaaacgt gcggccgcag gtgcgccggt gccgtatccg    780
gatccgctgg aaccgcgt                                                 798

<210> SEQ ID NO 22
<211> LENGTH: 266
<212> TYPE: PRT
<213> ORGANISM: Artificial Sequence
<220> FEATURE:
<223> OTHER INFORMATION: recombinant phage single chain Fv H20 antibody
      amino acid sequence

<400> SEQUENCE: 22

Met Ala Gln Val Gln Leu Gln Gln Ser Gly Ala Lys Leu Val Arg Ser
1               5                   10                  15

Gly Ala Ser Val Lys Leu Ser Cys Thr Thr Ser Gly Phe Asn Ile Lys
            20                  25                  30

Asp Tyr Tyr Met His Trp Val Lys Gln Arg Pro Glu Gln Gly Leu Glu
        35                  40                  45

Trp Ile Gly Trp Ile Asp Pro Glu Asn Gly Asp Thr Glu Tyr Ala Pro
    50                  55                  60

Lys Phe Gln Gly Lys Thr Thr Leu Thr Ala Asp Thr Ser Ser Asn Thr
65                  70                  75                  80

Ala Tyr Leu Gln Leu Ser Ser Leu Thr Ser Glu Asp Thr Ala Val Tyr
                85                  90                  95

Tyr Cys Asn Ala Trp Val Tyr Asp Gly Tyr Ser Gly Asp Phe Tyr Tyr
            100                 105                 110

Tyr Ala Met Asp Tyr Trp Gly Gln Gly Thr Thr Val Thr Cys Ser Ser
        115                 120                 125

Gly Gly Gly Gly Ser Gly Gly Gly Ser Gly Gly Gly Gly Ser Asp
    130                 135                 140

Ile Glu Leu Thr Gln Ser Pro Ala Ile Val Ser Ala Ser Pro Gly Glu
145                 150                 155                 160

Lys Val Thr Ile Thr Cys Ser Ala Ser Ser Ser Val Ser Tyr Met His
                165                 170                 175

Trp Phe Gln Gln Lys Pro Gly Thr Ser Pro Lys Leu Trp Ile Tyr Ser
            180                 185                 190

Thr Ser Asn Leu Ala Ser Gly Val Pro Ala Arg Phe Ser Gly Ser Gly
        195                 200                 205

Ser Gly Thr Ser Tyr Ser Leu Thr Ile Ser Arg Met Glu Ala Glu Asp
    210                 215                 220

Ala Ala Thr Tyr Tyr Cys Gln Gln Arg Ser Ser Tyr Pro Leu Thr Phe
225                 230                 235                 240

Gly Ala Gly Thr Lys Leu Glu Ile Lys Arg Ala Ala Ala Gly Ala Pro
                245                 250                 255

Val Pro Tyr Pro Asp Pro Leu Glu Pro Arg
            260                 265

<210> SEQ ID NO 23
<211> LENGTH: 10
<212> TYPE: PRT
<213> ORGANISM: Artificial Sequence
<220> FEATURE:
<223> OTHER INFORMATION: synthetic H6 KM1, Cys-Ser mutation of H6 KM0
      (Seq ID 3)

<400> SEQUENCE: 23

Glu Lys Val Thr Met Thr Ser Ser Ala Ser
1               5                   10

```
<210> SEQ ID NO 24
<211> LENGTH: 10
<212> TYPE: PRT
<213> ORGANISM: Artificial Sequence
<220> FEATURE:
<223> OTHER INFORMATION: synthetic H6 KM2, residues 91-100 of scFv H6
      (Seq ID 2)

<400> SEQUENCE: 24

Asp Thr Ala Arg Tyr Tyr Cys Leu Tyr Ala
1               5                   10

<210> SEQ ID NO 25
<211> LENGTH: 28
<212> TYPE: PRT
<213> ORGANISM: Artificial Sequence
<220> FEATURE:
<223> OTHER INFORMATION: synthetic H6 KM3 (H6 KM0 + linker + H6 KM2)

<400> SEQUENCE: 25

Glu Lys Val Thr Met Thr Cys Ser Ala Ser Ser Gly Gly Gly Gly
1               5                   10                  15

Gly Ser Asp Thr Ala Arg Tyr Tyr Cys Leu Tyr Ala
            20                  25

<210> SEQ ID NO 26
<211> LENGTH: 15
<212> TYPE: PRT
<213> ORGANISM: Artificial Sequence
<220> FEATURE:
<223> OTHER INFORMATION: synthetic H6 KM4, residues 146-160 of scFv H6
      (Seq ID 2)

<400> SEQUENCE: 26

Glu Lys Val Thr Met Thr Cys Ser Ala Ser Ser Ser Val Ser Tyr
1               5                   10                  15

<210> SEQ ID NO 27
<211> LENGTH: 9
<212> TYPE: PRT
<213> ORGANISM: Artificial Sequence
<220> FEATURE:
<223> OTHER INFORMATION: synthetic H6 KM5, residues 155-163 of scFv H6
      (Seq ID 2)

<400> SEQUENCE: 27

Ser Ser Ser Val Ser Tyr Met Tyr Trp
1               5

<210> SEQ ID NO 28
<211> LENGTH: 9
<212> TYPE: PRT
<213> ORGANISM: Artificial Sequence
<220> FEATURE:
<223> OTHER INFORMATION: synthetic irrelevant control peptide (IP)

<400> SEQUENCE: 28

Thr Ser Thr Thr Ser Leu Glu Leu Asp
1               5

<210> SEQ ID NO 29
<211> LENGTH: 10
<212> TYPE: PRT
<213> ORGANISM: Artificial Sequence
<220> FEATURE:
<223> OTHER INFORMATION: synthetic SP scramble control peptide
```

```
<400> SEQUENCE: 29

Met Ser Thr Ala Val Ser Lys Cys Ala Thr
1               5                   10

<210> SEQ ID NO 30
<211> LENGTH: 8
<212> TYPE: PRT
<213> ORGANISM: Artificial Sequence
<220> FEATURE:
<223> OTHER INFORMATION: synthetic Linker used to join H6 KM0 and H6
      KM2 to give H6 KM3

<400> SEQUENCE: 30

Ser Gly Gly Gly Gly Gly Gly Ser
1               5

<210> SEQ ID NO 31
<211> LENGTH: 9
<212> TYPE: PRT
<213> ORGANISM: Artificial Sequence
<220> FEATURE:
<223> OTHER INFORMATION: synthetic Peptide control

<400> SEQUENCE: 31

Tyr Met Trp Tyr Thr Trp Gly Thr Gly
1               5

<210> SEQ ID NO 32
<211> LENGTH: 10
<212> TYPE: PRT
<213> ORGANISM: Artificial Sequence
<220> FEATURE:
<223> OTHER INFORMATION: synthetic H6 KM derivative (Cys-Xaa mutation
      of Seq ID 4)
<220> FEATURE:
<222> LOCATION: 7
<223> OTHER INFORMATION: Xaa is any amino acid except Cys

<400> SEQUENCE: 32

Ala Lys Val Thr Met Thr Xaa Ser Ala Ser
1               5                   10

<210> SEQ ID NO 33
<211> LENGTH: 10
<212> TYPE: PRT
<213> ORGANISM: Artificial Sequence
<220> FEATURE:
<223> OTHER INFORMATION: synthetic H6 KM derivative (Seq ID 32 with
      Xaa = Ser)

<400> SEQUENCE: 33

Ala Lys Val Thr Met Thr Ser Ser Ala Ser
1               5                   10

<210> SEQ ID NO 34
<211> LENGTH: 10
<212> TYPE: PRT
<213> ORGANISM: Artificial Sequence
<220> FEATURE:
<223> OTHER INFORMATION: synthetic H20 KM0, residues 160-169 of H20
      (Seq ID 22)

<400> SEQUENCE: 34

Glu Lys Val Thr Ile Thr Cys Ser Ala Ser
1               5                   10
```

```
<210> SEQ ID NO 35
<211> LENGTH: 10
<212> TYPE: PRT
<213> ORGANISM: Artificial Sequence
<220> FEATURE:
<223> OTHER INFORMATION: synthetic H20 KM1, Cys-Ser mutation of H20 KM0
      (Seq ID 34)

<400> SEQUENCE: 35

Glu Lys Val Thr Ile Thr Ser Ser Ala Ser
1               5                   10

<210> SEQ ID NO 36
<211> LENGTH: 10
<212> TYPE: PRT
<213> ORGANISM: Artificial Sequence
<220> FEATURE:
<223> OTHER INFORMATION: synthetic H20 KM2, residues 91-100 of H20
      (Seq ID 22)

<400> SEQUENCE: 36

Asp Thr Ala Val Tyr Tyr Cys Asn Ala Trp
1               5                   10

<210> SEQ ID NO 37
<211> LENGTH: 15
<212> TYPE: PRT
<213> ORGANISM: Artificial Sequence
<220> FEATURE:
<223> OTHER INFORMATION: synthetic H20 KM4, residues 160-174 of H20
      (Seq ID 22)

<400> SEQUENCE: 37

Glu Lys Val Thr Ile Thr Cys Ser Ala Ser Ser Ser Val Ser Tyr
1               5                   10                  15

<210> SEQ ID NO 38
<211> LENGTH: 9
<212> TYPE: PRT
<213> ORGANISM: Artificial Sequence
<220> FEATURE:
<223> OTHER INFORMATION: synthetic H20 KM5, residues 169-177 of H20
      (Seq ID 22)

<400> SEQUENCE: 38

Ser Ser Ser Val Ser Tyr Met His Trp
1               5

<210> SEQ ID NO 39
<211> LENGTH: 10
<212> TYPE: PRT
<213> ORGANISM: Artificial Sequence
<220> FEATURE:
<223> OTHER INFORMATION: synthetic H20 KM, Glu-Ala mutation of H 20 KM0
      (Seq ID 34)

<400> SEQUENCE: 39

Ala Lys Val Thr Ile Thr Cys Ser Ala Ser
1               5                   10

<210> SEQ ID NO 40
<211> LENGTH: 10
<212> TYPE: PRT
<213> ORGANISM: Artificial Sequence
<220> FEATURE:
<223> OTHER INFORMATION: synthetic H6 KM2-derived peptide,
      alanine-scanning variant of H6 KM2 (seq ID 24)

<400> SEQUENCE: 40
```

```
Ala Thr Ala Arg Tyr Tyr Cys Leu Tyr Ala
1               5                   10

<210> SEQ ID NO 41
<211> LENGTH: 10
<212> TYPE: PRT
<213> ORGANISM: Artificial Sequence
<220> FEATURE:
<223> OTHER INFORMATION: synthetic H6 KM2-derived peptide,
      alanine-scanning variant of H6 KM2 (seq ID 24)

<400> SEQUENCE: 41

Asp Ala Ala Arg Tyr Tyr Cys Leu Tyr Ala
1               5                   10

<210> SEQ ID NO 42
<211> LENGTH: 10
<212> TYPE: PRT
<213> ORGANISM: Artificial Sequence
<220> FEATURE:
<223> OTHER INFORMATION: synthetic H6 KM2-derived peptide,
      alanine-scanning variant of H6 KM2 (seq ID 24)

<400> SEQUENCE: 42

Asp Thr Ala Ala Tyr Tyr Cys Leu Tyr Ala
1               5                   10

<210> SEQ ID NO 43
<211> LENGTH: 10
<212> TYPE: PRT
<213> ORGANISM: Artificial Sequence
<220> FEATURE:
<223> OTHER INFORMATION: synthetic H6 KM2-derived peptide,
      alanine-scanning variant of H6 KM2 (seq ID 24)

<400> SEQUENCE: 43

Asp Thr Ala Arg Ala Tyr Cys Leu Tyr Ala
1               5                   10

<210> SEQ ID NO 44
<211> LENGTH: 10
<212> TYPE: PRT
<213> ORGANISM: Artificial Sequence
<220> FEATURE:
<223> OTHER INFORMATION: synthetic H6 KM2-derived peptide,
      alanine-scanning variant of H6 KM2 (seq ID 24)

<400> SEQUENCE: 44

Asp Thr Ala Arg Tyr Ala Cys Leu Tyr Ala
1               5                   10

<210> SEQ ID NO 45
<211> LENGTH: 10
<212> TYPE: PRT
<213> ORGANISM: Artificial Sequence
<220> FEATURE:
<223> OTHER INFORMATION: synthetic H6 KM2-derived peptide,
      alanine-scanning variant of H6 KM2 (seq ID 24)

<400> SEQUENCE: 45

Asp Thr Ala Arg Tyr Tyr Ala Leu Tyr Ala
1               5                   10

<210> SEQ ID NO 46
<211> LENGTH: 10
<212> TYPE: PRT
<213> ORGANISM: Artificial Sequence
```

```
<220> FEATURE:
<223> OTHER INFORMATION: synthetic H6 KM2-derived peptide,
      alanine-scanning variant of H6 KM2 (seq ID 24)

<400> SEQUENCE: 46

Asp Thr Ala Arg Tyr Tyr Cys Ala Tyr Ala
1               5                   10

<210> SEQ ID NO 47
<211> LENGTH: 10
<212> TYPE: PRT
<213> ORGANISM: Artificial Sequence
<220> FEATURE:
<223> OTHER INFORMATION: synthetic H6 KM2-derived peptide,
      alanine-scanning variant of H6 KM2 (seq ID 24)

<400> SEQUENCE: 47

Asp Thr Ala Arg Tyr Tyr Cys Leu Ala Ala
1               5                   10

<210> SEQ ID NO 48
<211> LENGTH: 10
<212> TYPE: PRT
<213> ORGANISM: Artificial Sequence
<220> FEATURE:
<223> OTHER INFORMATION: synthetic H6 KM2-derived peptide, Cys-Ser
      mutation of H6 KM2 (seq ID 24)

<400> SEQUENCE: 48

Asp Thr Ala Arg Tyr Tyr Ser Leu Tyr Ala
1               5                   10

<210> SEQ ID NO 49
<211> LENGTH: 9
<212> TYPE: PRT
<213> ORGANISM: Artificial Sequence
<220> FEATURE:
<223> OTHER INFORMATION: synthetic H6 KM5-derived peptide,
      alanine-scanning variant of H6 KM5 (seq ID 27)

<400> SEQUENCE: 49

Ala Ser Ser Val Ser Tyr Met Tyr Trp
1               5

<210> SEQ ID NO 50
<211> LENGTH: 9
<212> TYPE: PRT
<213> ORGANISM: Artificial Sequence
<220> FEATURE:
<223> OTHER INFORMATION: synthetic H6 KM5-derived peptide,
      alanine-scanning variant of H6 KM5 (seq ID 27)

<400> SEQUENCE: 50

Ser Ala Ser Val Ser Tyr Met Tyr Trp
1               5

<210> SEQ ID NO 51
<211> LENGTH: 9
<212> TYPE: PRT
<213> ORGANISM: Artificial Sequence
<220> FEATURE:
<223> OTHER INFORMATION: synthetic H6 KM5-derived peptide,
      alanine-scanning variant of H6 KM5 (seq ID 27)

<400> SEQUENCE: 51

Ser Ser Ala Val Ser Tyr Met Tyr Trp
1               5
```

<210> SEQ ID NO 52
<211> LENGTH: 9
<212> TYPE: PRT
<213> ORGANISM: Artificial Sequence
<220> FEATURE:
<223> OTHER INFORMATION: synthetic H6 KM5-derived peptide,
      alanine-scanning variant of H6 KM5 (seq ID 27)

<400> SEQUENCE: 52

Ser Ser Ser Ala Ser Tyr Met Tyr Trp
1               5

<210> SEQ ID NO 53
<211> LENGTH: 9
<212> TYPE: PRT
<213> ORGANISM: Artificial Sequence
<220> FEATURE:
<223> OTHER INFORMATION: synthetic H6 KM5-derived peptide,
      alanine-scanning variant of H6 KM5 (seq ID 27)

<400> SEQUENCE: 53

Ser Ser Ser Val Ala Tyr Met Tyr Trp
1               5

<210> SEQ ID NO 54
<211> LENGTH: 9
<212> TYPE: PRT
<213> ORGANISM: Artificial Sequence
<220> FEATURE:
<223> OTHER INFORMATION: synthetic H6 KM5-derived peptide,
      alanine-scanning variant of H6 KM5 (seq ID 27)

<400> SEQUENCE: 54

Ser Ser Ser Val Ser Ala Met Tyr Trp
1               5

<210> SEQ ID NO 55
<211> LENGTH: 9
<212> TYPE: PRT
<213> ORGANISM: Artificial Sequence
<220> FEATURE:
<223> OTHER INFORMATION: synthetic H6 KM5-derived peptide,
      alanine-scanning variant of H6 KM5 (seq ID 27)

<400> SEQUENCE: 55

Ser Ser Ser Val Ser Tyr Ala Tyr Trp
1               5

<210> SEQ ID NO 56
<211> LENGTH: 9
<212> TYPE: PRT
<213> ORGANISM: Artificial Sequence
<220> FEATURE:
<223> OTHER INFORMATION: synthetic H6 KM5-derived peptide,
      alanine-scanning variant of H6 KM5 (seq ID 27)

<400> SEQUENCE: 56

Ser Ser Ser Val Ser Tyr Met Ala Trp
1               5

<210> SEQ ID NO 57
<211> LENGTH: 9
<212> TYPE: PRT
<213> ORGANISM: Artificial Sequence
<220> FEATURE:
<223> OTHER INFORMATION: synthetic H6 KM5-derived peptide,
      alanine-scanning variant of H6 KM5 (seq ID 27)

```
<400> SEQUENCE: 57

Ser Ser Ser Val Ser Tyr Met Tyr Ala
1               5

<210> SEQ ID NO 58
<211> LENGTH: 15
<212> TYPE: PRT
<213> ORGANISM: Artificial Sequence
<220> FEATURE:
<223> OTHER INFORMATION: synthetic H6 KM4-derived peptide, Cys-Ser
      mutation of H6 KM4 (seq ID 26)

<400> SEQUENCE: 58

Glu Lys Val Thr Met Thr Ser Ser Ala Ser Ser Ser Val Ser Tyr
1               5                   10                  15

<210> SEQ ID NO 59
<211> LENGTH: 13
<212> TYPE: PRT
<213> ORGANISM: Artificial Sequence
<220> FEATURE:
<223> OTHER INFORMATION: synthetic C-terminus E-tag system for scFv

<400> SEQUENCE: 59

Gly Ala Pro Val Pro Tyr Pro Asp Pro Leu Glu Pro Arg
1               5                   10

<210> SEQ ID NO 60
<211> LENGTH: 5
<212> TYPE: PRT
<213> ORGANISM: Artificial sequence
<220> FEATURE:
<223> OTHER INFORMATION: synthetic H6 CDR-H1, residues 33-37 of H6
      (Seq ID 2)

<400> SEQUENCE: 60

Gly Tyr Gly Val Asn
1               5

<210> SEQ ID NO 61
<211> LENGTH: 14
<212> TYPE: PRT
<213> ORGANISM: Artificial sequence
<220> FEATURE:
<223> OTHER INFORMATION: synthetic H6 CDR-H2, residues 52-65 of H6
      (Seq ID 2)

<400> SEQUENCE: 61

Met Ile Trp Gly Asp Gly Ser Thr Asp Tyr Asn Ser Ala Leu
1               5                   10

<210> SEQ ID NO 62
<211> LENGTH: 4
<212> TYPE: PRT
<213> ORGANISM: Artificial sequence
<220> FEATURE:
<223> OTHER INFORMATION: synthetic H6 CDR-H3, residues 98-101 of H6
      (Seq ID 2)

<400> SEQUENCE: 62

Leu Tyr Ala Met
1

<210> SEQ ID NO 63
<211> LENGTH: 10
<212> TYPE: PRT
<213> ORGANISM: Artificial sequence
```

```
<220> FEATURE:
<223> OTHER INFORMATION: synthetic H6 CDR-L1, residues 153-162 of H6
      (Seq ID 2)

<400> SEQUENCE: 63

Ser Ala Ser Ser Ser Val Ser Tyr Met Tyr
1               5                   10

<210> SEQ ID NO 64
<211> LENGTH: 7
<212> TYPE: PRT
<213> ORGANISM: Artificial sequence
<220> FEATURE:
<223> OTHER INFORMATION: synthetic H6 CDR-L2, residues 178-184 of H6
      (Seq ID 2)

<400> SEQUENCE: 64

Leu Thr Ser Asn Leu Ala Ser
1               5

<210> SEQ ID NO 65
<211> LENGTH: 8
<212> TYPE: PRT
<213> ORGANISM: Artificial sequence
<220> FEATURE:
<223> OTHER INFORMATION: synthetic H6 CDR-L3, residues 217-224 of H6
      (Seq ID 2)

<400> SEQUENCE: 65

Gln Gln Trp Ser Ser Asn Pro Tyr
1               5

<210> SEQ ID NO 66
<211> LENGTH: 5
<212> TYPE: PRT
<213> ORGANISM: Artificial sequence
<220> FEATURE:
<223> OTHER INFORMATION: synthetic H20 CDR-H1, residues 33-37 of H20
      (Seq ID 22)

<400> SEQUENCE: 66

Asp Tyr Tyr Met His
1               5

<210> SEQ ID NO 67
<211> LENGTH: 15
<212> TYPE: PRT
<213> ORGANISM: Artificial sequence
<220> FEATURE:
<223> OTHER INFORMATION: synthetic H20 CDR-H2, residues 52-66 of H20
      (Seq ID 22)

<400> SEQUENCE: 67

Trp Ile Asp Pro Glu Asn Gly Asp Thr Glu Tyr Ala Pro Lys Phe
1               5                   10                  15

<210> SEQ ID NO 68
<211> LENGTH: 17
<212> TYPE: PRT
<213> ORGANISM: Artificial sequence
<220> FEATURE:
<223> OTHER INFORMATION: synthetic H20 CDR-H3, residues 99-115 of H20
      (Seq ID 22)

<400> SEQUENCE: 68

Asn Ala Trp Val Tyr Asp Gly Tyr Ser Gly Asp Phe Tyr Tyr Tyr Ala
1               5                   10                  15
```

```
Met

<210> SEQ ID NO 69
<211> LENGTH: 10
<212> TYPE: PRT
<213> ORGANISM: Artificial sequence
<220> FEATURE:
<223> OTHER INFORMATION: synthetic H20 CDR-L1, residues 167-176 of H20
      (Seq ID 22)

<400> SEQUENCE: 69

Ser Ala Ser Ser Ser Val Ser Tyr Met His
1               5                   10

<210> SEQ ID NO 70
<211> LENGTH: 7
<212> TYPE: PRT
<213> ORGANISM: Artificial sequence
<220> FEATURE:
<223> OTHER INFORMATION: synthetic H20 CDR-L2, residues 192-198 of H20
      (Seq ID 22)

<400> SEQUENCE: 70

Ser Thr Ser Asn Leu Ala Ser
1               5

<210> SEQ ID NO 71
<211> LENGTH: 8
<212> TYPE: PRT
<213> ORGANISM: Artificial sequence
<220> FEATURE:
<223> OTHER INFORMATION: synthetic H20 CDR-L3, residues 231-238 of H20
      (Seq ID 22)

<400> SEQUENCE: 71

Gln Gln Arg Ser Ser Tyr Pro Leu
1               5
```